US010934557B2

(12) United States Patent
Slade et al.

(10) Patent No.: US 10,934,557 B2
(45) Date of Patent: Mar. 2, 2021

(54) WHEAT WITH INCREASED RESISTANT STARCH LEVELS

(71) Applicant: Arcadia Biosciences, Inc., Davis, CA (US)

(72) Inventors: Ann J. Slade, Bellevue, WA (US); Dayna L. Loeffler, Seattle, WA (US); Aaron M. Holm, Shoreline, WA (US); Jessica C. Mullenberg, Lynnwood, WA (US)

(73) Assignee: ARCADIA BIOSCIENCES, INC., Davis, CA (US)

( * ) Notice: Subject to any disclaimer, the term of this patent is extended or adjusted under 35 U.S.C. 154(b) by 0 days.

(21) Appl. No.: 15/914,994

(22) Filed: Mar. 7, 2018

(65) Prior Publication Data
US 2019/0085348 A1 Mar. 21, 2019

Related U.S. Application Data

(63) Continuation of application No. 14/825,369, filed on Aug. 13, 2015, which is a continuation of application No. 13/633,588, filed on Oct. 2, 2012, now Pat. No. 9,150,839.

(60) Provisional application No. 61/542,953, filed on Oct. 4, 2011.

(51) Int. Cl.
*C12N 15/00* (2006.01)
*A01H 6/46* (2018.01)
*A23L 7/10* (2016.01)
*C12N 15/82* (2006.01)
*C12N 9/10* (2006.01)

(52) U.S. Cl.
CPC ....... *C12N 15/8245* (2013.01); *A01H 6/4678* (2018.05); *C12N 9/107* (2013.01); *C12Y 204/01018* (2013.01)

(58) Field of Classification Search
None
See application file for complete search history.

(56) References Cited

U.S. PATENT DOCUMENTS

| | | | |
|---|---|---|---|
| 3,690,896 A | 9/1972 | Maxwell et al. | |
| 4,770,710 A | 9/1988 | Friedman et al. | |
| 5,051,271 A | 9/1991 | Iyengar et al. | |
| 5,994,075 A | 11/1999 | Goodfellow | |
| 6,013,861 A | 1/2000 | Bird et al. | |
| 6,303,174 B1 | 10/2001 | McNaught et al. | |
| 6,307,125 B1 | 10/2001 | Block et al. | |
| 6,376,749 B1 | 4/2002 | Broglie et al. | |
| 6,483,009 B1 | 11/2002 | Poulsen et al. | |
| 6,730,825 B1 | 5/2004 | Goldsbrough et al. | |
| 6,734,339 B2 | 5/2004 | Block et al. | |
| 6,897,354 B1 | 5/2005 | Yamamori et al. | |
| 6,903,255 B2 | 6/2005 | Yamamori et al. | |
| 6,916,976 B1 | 7/2005 | Li et al. | |
| 7,001,771 B1 | 2/2006 | Morell et al. | |
| 7,009,092 B1 | 3/2006 | Jane et al. | |
| 7,041,484 B1 | 5/2006 | Baga et al. | |
| 7,521,593 B2 | 4/2009 | Regina et al. | |
| 7,667,114 B2 | 2/2010 | Morell et al. | |
| 7,700,139 B2 | 4/2010 | Bird et al. | |
| 7,700,826 B2 | 4/2010 | Morell et al. | |
| 7,750,206 B2 | 7/2010 | Li et al. | |
| 7,790,955 B2 | 9/2010 | Li et al. | |
| 7,812,221 B2 | 10/2010 | Regina et al. | |
| 7,888,499 B2 | 2/2011 | Morell et al. | |
| 7,919,132 B2 | 4/2011 | Regina et al. | |
| 7,993,686 B2 | 8/2011 | Bird et al. | |
| 8,115,087 B2 | 2/2012 | Regina et al. | |
| 8,178,759 B2 | 5/2012 | Morell et al. | |
| 8,188,336 B2 | 5/2012 | Li et al. | |
| 8,501,262 B2 | 8/2013 | Bird et al. | |
| 8,829,315 B2 | 9/2014 | Regina et al. | |
| 9,060,533 B2 * | 6/2015 | Regina .................. | C12N 9/107 |
| 9,357,722 B2 | 6/2016 | Regina et al. | |
| 2003/0035857 A1 | 2/2003 | Sroka et al. | |
| 2004/0023236 A1 | 3/2004 | McCallum et al. | |
| 2004/0060083 A1 | 3/2004 | Morell et al. | |
| 2004/0199942 A1 | 10/2004 | Morell et al. | |
| 2004/0204579 A1 | 10/2004 | Block et al. | |
| 2005/0071896 A1* | 3/2005 | Regina ..................... | A01H 5/10 800/284 |
| 2005/0164178 A1 | 4/2005 | Morell et al. | |
| 2006/0010517 A1 | 1/2006 | Li et al. | |
| 2006/0035379 A1 | 2/2006 | Morell et al. | |
| 2006/0204597 A1 | 9/2006 | Bird et al. | |
| 2006/0286186 A1 | 12/2006 | Bird et al. | |

(Continued)

FOREIGN PATENT DOCUMENTS

| | | |
|---|---|---|
| CN | 1875105 A | 12/2006 |
| GB | 2 360 521 | 9/2001 |
| WO | WO 1997/022703 | 6/1997 |
| WO | WO 1999/014314 | 3/1999 |
| WO | WO 1999/0066050 | 12/1999 |

(Continued)

OTHER PUBLICATIONS

Office Action for U.S. Appl. No. 14/825,369 (dated Aug. 27, 2018).

(Continued)

*Primary Examiner* — Jason Deveau Rosen
(74) *Attorney, Agent, or Firm* — Troutman Pepper Hamilton Sanders LLP (Rochester)

(57) ABSTRACT

A series of independent human-induced non-transgenic mutations found at one or more of the SBEII genes of wheat; wheat plants having these mutations in one or more of their SBEII genes; and a method of creating and finding similar and/or additional mutations of SBEII by screening pooled and/or individual wheat plants. The seeds and flour from the wheat plants of the present invention exhibit an increase in amylose and resistant starch without having the inclusion of foreign nucleic acids in their genomes. Additionally, the wheat plants of the present invention exhibit altered SBEII activity without having the inclusion of foreign nucleic acids in their genomes.

10 Claims, No Drawings

Specification includes a Sequence Listing.

(56) References Cited

U.S. PATENT DOCUMENTS

| | | |
|---|---|---|
| 2007/0261136 A1* | 11/2007 | Singletary ............ C12N 9/1051 800/284 |
| 2007/0300319 A1 | 12/2007 | Li et al. |
| 2009/0226592 A1 | 9/2009 | Regina et al. |
| 2010/0330253 A1 | 12/2010 | Morell et al. |
| 2011/0010807 A1 | 1/2011 | Morell et al. |
| 2011/0045127 A1 | 2/2011 | Ral et al. |
| 2011/0059225 A1 | 3/2011 | Li et al. |
| 2011/0070352 A1 | 3/2011 | Regina et al. |
| 2011/0212916 A1 | 9/2011 | Bird et al. |
| 2011/0281818 A1 | 11/2011 | Jenkins et al. |
| 2012/0074247 A1 | 3/2012 | Regina et al. |
| 2012/0114770 A1 | 5/2012 | Regina et al. |
| 2012/0129805 A1 | 5/2012 | Li et al. |
| 2012/0266267 A1 | 10/2012 | Li et al. |
| 2013/0115362 A1 | 5/2013 | Regina et al. |
| 2013/0156924 A1 | 6/2013 | Morell et al. |
| 2014/0044826 A1 | 2/2014 | Regina et al. |
| 2017/0367382 A1* | 12/2017 | Regina .................... A23L 7/197 |

FOREIGN PATENT DOCUMENTS

| | | |
|---|---|---|
| WO | WO 2000/015810 | 3/2000 |
| WO | WO 2000/066745 | 9/2000 |
| WO | WO 2001/032886 | 5/2001 |
| WO | WO 2001/062934 | 8/2001 |
| WO | WO 2002/037955 | 5/2002 |
| WO | WO 2002/101059 | 12/2002 |
| WO | WO 2003/023024 | 3/2003 |
| WO | WO 2003/094600 | 11/2003 |
| WO | WO 2005/040381 | 6/2005 |
| WO | WO 2006/069422 | 7/2006 |
| WO | WO 2011/011833 | 2/2011 |
| WO | WO 2012058730 | 5/2012 |
| WO | WO 2012/0103594 | 8/2012 |
| WO | WO 2013/052499 | 4/2013 |

OTHER PUBLICATIONS

Interview Summary for U.S. Appl. No. 15/975,410 (dated Sep. 13, 2018).
Interview Summary for U.S. Appl. No. 15/649,231 (dated Sep. 13, 2018).
Decision Motions, Patent Interference 106,094 *Regina v. Slade*, Dated Aug. 14, 2018.
Office Action for U.S. Appl. No. 15/649,231 (dated Jul. 11, 2018).
Office Action for U.S. Appl. No. 15/975,410 (dated Jul. 18, 2018).
Wiersma et al., "Recurrent Selection for Kernel Weight in Spring Wheat," Crop Science 41:999-1005 (2001).
Regina Reply 1 Written Description, Patent Interference 106,094 *Regina v. Slade*, Dated Jul. 17, 2018.
Regina Motion 2 Benefit, Patent Interference 106,094 *Regina v. Slade*, Dated Jul. 17, 2018.
Corrected Brief for Appellants *Slade et al. v. Regina et al.* U.S. Interference No. 106,094, Dated Dec. 17, 2018.
Examination Report for India Application No. 706/KOLNP/2014 (dated Oct. 23, 2018) (which attached partial translation).
Examination Report for Canada Application No. 2,850,490 (dated Jul. 12, 2018).
Office Action for European Patent Application No. 12 775 107.1, dated Nov. 30, 2017.
Examination Report No. 2 for Australian Patent Application No. 2012318814, dated Feb. 26, 2018.
English Translation of Pertinent Portion of the Decision of Reexamination for China Patent Application No. 201280059762.8, dated Mar. 9, 2018.
Regina List of Proposed Motions, Patent Interference 106,094 *Regina v. Slade*, Dated Apr. 4, 2018.
Office Action for U.S. Appl. No. 15/615,555, dated Feb. 2, 2018.
Regina Motion 1 Written Description 112 1st, Patent Interference 106,094 *Regina v. Slade*, dated May 2, 2018.

Abel et al., GenBank Accession #Y10416, S. Tuberosum mRNA for Soluble Starch Synthase (Jan. 1997).
Abel et al., "Cloning and functional analysis of a cDNA encoding a novel 139 kDa Starch Synthase from Potato (*Solanum tuberosum* L.)," Plant J. 10(6):981-991 (1996).
Ainsworth et al., "Expression, organization and structure of the genes encoding the waxy protein (granule-bound starch synthase) in wheat," Plant Mol. Biol. 22:67-82 (1993).
Arnold, "Molecular pathogenesis of colorectal cancer", 2005, Cancer, vol. 104, pp. 2035-2047.
Baba et al., "Identification, cDNA cloning and gene expression of soluble starch synthase in rice (*Oiyza stativa* L.) Immature Seeds," Plant Physiol. 103:565-573 (1993).
Ball et al., "From glycogen to amylopectin: A model for the biogenesis of theplant starch granule," Cell 86:349-352, 1996.
Banks et al., "Studies on Starches of High Amylose Content," Starch 26:289-300 (1974).
Batey et al., "Measurement of Amylose/Amylopectin Ratio by High-Performance Liquid Chromatography," Starch 48:338-344 (1996).
Bernardo et al., North American study on essential derivation in maize: inbreds developed without and with selection from F2 populations, Theor Appl Genet (2001) 102:986-992, 7 pages.
Bhullar et al., GenBank Accession #CAB40374, Starch synthase isoform SS III (*Vigna unguiculata*) (Apr. 1999).
Blauth et al., "Identification of Mutator Insertional Mutants of Starch-Branching Enzyme 2a in Corn," Plant Physiology 125:1396-1405 (2001).
Block et al., GenBank Accession #U48227, Triticum aestivm soluble starch synthase mRNA, partial cds. (Jun. 1996).
Boyer et., "Evidence for Independent Genetic Control of the Multiple Forms of Maize Endosperm Branching Enzymes and Starch Synthases," Plant Physiology 67:1141-1145 (1981).
Buleon et al., "Starch Granules: Structure and Biosynthesis," International Journal of Biological Macromolecules 23:85-112 (1998).
Butardo et al., "Impact of down-regulation of starch branching enzyme llb in rice by artificial microRNA- and hairpin RNA-mediated RNA silencing," J. Exp. Bot. 62:4927-4941, 2011.
Chen et al., "A rapid DNA minipreparation method suitable for AFLP and other PCR applications," Plant Molecular Biology Reporter 17:53-57, 1999.
Chinese Office Action and English translation for application No. 201280059762.8 dated Jun. 24, 2015, 10 pages.
Clarke et al., "Gene expression in a starch synthase IIa mutant of barley: changes in the level of gene transcription and grain composition." Functional Integrated Genomics, 2008, 8:211-221.
Colasuonno et al., "TILLING starch branching enzyme-lla and llb to produce high amylose wheat," Abstract P292 from the Plant & Animal Genomes XVII Conference, San Diego, CA, Jan. 10-14, 2009.
Colbert et al., "High-throughput screening for induced point mutations," Plant Physiology 126:480-484, 2001.
Craig et al., "Mutations in the Gene Encoding Starch Synthase II Profoundly Alter Amylopectin Structure in Pea Embroyos," The Plant Cell 10:413-426 (1998).
Denyer et al., "Identification of Multiple Isoforms of Soluble and Granule Bound Starch Synthase in Developing Wheat Endosperm." Planta 196:256-265 (1995).
D'Hulst et al., GenBank Accession #AAC17969, Granule-bound starch synthase I precursor [*Chlamydomonas reinhardtii*] (Nov. 2001).
Dry et al., "Characterization of cDNAs encoding two isoforms of granule-bound synthase which show differential expression in developing storage organs of pea and potato," Plant J. 2(2):193-202 (1992).
Edwards et al., "Biochemical and Molecular Characterization of a Novel Starch Synthase from Potato Tubers," Plant J. 8(2):283-294 (1995).
English language abstract of PCT International Patent Application Publication No. WO 2003/023024, published Mar. 20, 2003 (Japan Science and Technology Corporation).
European Office Action for application No. 12775107.1 dated Jun. 1, 2015, 4 pages.

(56) References Cited

OTHER PUBLICATIONS

Feiz et al., "In planta mutagenesis determines the functional regions of the wheat puroindoline proteins," Genetic 183:853-860,2009.
Fujita et al., (2007) "Characterization of SSIIIa-Deficient Mutants of Rice: The Function of SSIIIa and Pleiotropic Effects by SSIIIa Deficiency in the Rice Endosperm" Plant Physiology , 144: 2009-2023.
Flipse et al., "Introduction of Sense and Antisense cDNA for Branching Enzyme in the Amylose-Free Potato Mutant Leads to Physico-Chemical Changes in the Starch," Planta 198:340-347 (1996).
Fujita et al., "Antisense Inhibition of Isoamylase Alters the Structure of Amylopectin and the Physiochemical Properties of Starch in Rice Endosperm," Plant Cell Physiol. 44(6):607-618 (2003).
Fujita et al., "Grain and Starch Characteristics of the Double Recessive Lines for Amylose-free and High Amylose Gene in Barley," Breeding Science 49:217-219 (1999).
Gao et al., "Isolation, Characterization, and Expression Analysis of Starch Synthase IIa cDNA from wheat (*Triticum aestivum* L.)," Genome 43:768-775 (2000).
Gao et al., "Characterization of dull I, a Maize Gene Coding for a Novel Starch Synthase," Plant Cell 10:399-412 (1998).
Gao et al., Triticum aestivum mRNA for Starch Synthase IIa-2 (wSs2a-2), EMBL Abstract Accession No. AJ269503 (Jul. 6, 2000).
Gao et al., GenBank Accession #AAC14014, Starch synthase DULL 1 [*Zea mays*] (Apr. 1998).
Gao et al., GenBank Accession #AAC14015, Starch synthase DULL 1 [*Zea mays*] (Apr. 1998).
Gao et al., GenBank Accession #AJ26502, Triticum aestivum mRNA for starch synthase Iia-1 (wSs2a-1 gene) (Apr. 2002).
Gao et al., GenBank Accession #CAB86618, Starch synthase Iia-1 [*Triticum aestivum*] (Apr. 2002).
Gillespie, "Type 1 diabetes: pathogenesis and prevention", CMAJ, 2006, vol. 175, pp. 165-170.
Goering, et al., "A Comparison of the Properties of Large- and Small-Granule Starch Isolated from Several Isogenic Lines of Barley," Cereal Chemistry 51:573-578 (1974).
Harn et al., "Isolation and Characterization of the zSSIIA and zSSIIb Starch Synthase cDNA Clones from Maize Endosperm," Plant Mol. Biol. 37:639-649 (1998).
Henikoff et al., "Using substitution probabilities to improve position specific scoring matrices," Computer Applications in the Biosciences 12: 135-143, 1996.
Henikoff et al., "Amino acid substitution matrices from protein blocks," Proc. Natl. Acad. Sci. USA 89:10915-10919,1992.
Holmes et al., Henderson's Dictionary of Biological Terms, 9th Ed., Van Nostrand Reinhold Co., New York, 1979, p. 218.
Innis et al., "PCR protocols: A guide to methods and applications," Academic Press, San Diego, 1990.
International Search Report, dated Jan. 17, 2012 in connection with PCT International Application No. PCT/AU2011/01426.
International Search Report, dated May 14, 2012 in connection with PCT International Patent Application No. PCT/AU2012/000098.
Jansson et al., "Cloning, Characterization and Modification of Genes Encoding Starch Branching Enzymes in Barley," Starch: Structure and Functionality, Royal Society of Chemistry, London, pp. 196-203 (1997).
Jarvi et al., "Shrunken Endosperm Mutants in Barley," Crop Science 15:363-366 (1975).
Kim et al., "Oryza minuta genomic clone OM Ba0201cll 5", Database Embase Elsevier Science Publishers, Amsterdam, NL, Jul. 8, 2005.
Klosgen et al., "Molecular Analysis of the Waxy Locus of *Zea mays*," Mol. Gen.Genet. 203:237-244 (1986).
Knight et al., "Molecular Cloning of Starch Synthase I from Maize (w64) Endosperm and Expression in *Escherichia coli*," Plant J. 14(5):613-622 (1998).
Konovalov et al., An approach to DNA polymorphism screening in SBElla homeologous genes of polyploid wheat (*Triticum* L.) Euphytica 183(2), 173-184, 2011 (Abstract Only).

Konovalov et al., "The sequence polymorphism of SBElla gene in wheat (*Triticum* sp.) In: Appeals R, Eastwood R, LagudahE, Landridge P, Mackay M, McIntyre L, Sharp P (eds) Proc." IlthInt. Wheat Genet. Symp. pp. 418-420, 2008.
Kull et al., "Genetic Engineering of Potato Starch Composition: Inhibition of Amylose Biosynthesis in Tubers from Transgentic Potato Lines by the Expression of Antisense Sequences of the Gene for Granule-bound Starch Synthase," J. Genet. Breed. 49:69-76 (1995).
Li et al., "Integrated platform for detection of DNA sequence variants using capillary array electrophoresis," Electrophoresis 23(10): 1499-1511, 2002.
Li et al. (2011) "The barley amol locus is tightly linked to the starch synthase IIIa gene and negatively regulates expression of granule-bound starch synthetic genes" Journal of Experimental Botany 62:5217-5231.
Li et al., "Cloning and Characterization of a Gene Encoding Wheat Starch Synthase I," Theor. AEEI. Genet. 98:1208-1216 (1999).
Li et al., "The Localization and Expression of the Class II Starch Synthases of Wheat," Plant Physiology 120:1147-1155 (1999).
Li et al., (2003) "The structural organisation of the gene endoding class II starch synthase of wheat and barley and the evolution of the genes encoding starch synthases in plants" Funct Integr Genomics 3:76-85.
Li et al., Triticum aestivum Starch Synthase IIA mRNA, complete cds., EMBL Abstract Accession No. AF155217 (Sep. 7, 1999).
Liu et al., "Stable Inheritance of the Antisense Waxy Gene in Transgenic Rice with Reduced Amylose Level and Improved Quality," Transgenic Research, 12:71-82, (2003).
Lorberth et al., "Inhibition of a starch-granule-bound protein leads to modified starch and repression of cold sweetening." Nature Biotechnology, (1998); 16(1):473-477.
Martin et al., "Starch biosynthesis," The Plant Cell 7:971-985, 1995.
Mazzolini et al., "Assaying synthetic ribozymes in plants: high-level expression of a functional hammerhead structure fails to inhibit target gene activity in transiently transformed protoplasts," Plant Mol. Biol. 20:715-731 (1992).
Mccallum et al., "Target screening for induced mutations," Nature Biotechnology 18:455-457, 2000a.
Mccallum et al., "Targeting induced local lesions in genomes (TILLING) for plant functional genomics," Plant Physiology 123:439-442, 2000b.
Miao, Hongmei et al., "Evaluation and Characterization of an Endosperm-Specific sbella Promoter in Wheat II," Chinese Science Bulletin, vol. 49, No. 6, pp. 579-585 (2004).
Mizuno et al., "Alteration of the Structural Properties of Starch Components by the Lack of an Isoform of Starch Branching Enzyme in Rice Seeds," J. Biol. Chem. 268(25):19084-19091 (1993).
Morell et al., "Barley sex6 Mutants Lack Starch Synthase iia Activity and Contain a Starch with Novel Properties," The Plant Journal 34:173-185 (2003).
Morell et al., "The Biochemistry and Molecular Biology of Starch Synthesis in Cereals," Aust. J. Plant. Physiol. 22:647-660 (1995).
Myers et al., "Recent Progress toward Understanding Biosynthesis of the Amylopection Crystal," Plant Physiology 122:989-997 (2000).
Nakamura Y., "Towards a Better Understanding of the Metabolic System for Amylopectin Biosynthesis in Plants: Rice Endoserm as s Model Tissue," Plant Cell Physiology 43(7):718-725 (2002).
Needleman, A general method applicable to the search for similarities in the amino acid sequences of two proteins. J. Mol. Biol. 48:443-453, 1970.
Newman et al. (1978) "Comparative Nutritive Value of Glacier and High Amyliose Glacier Barleys" Journal of Animal Science, 47:448-456.
Ng et al., "SIFT: Predicting amino acid changes that affect protein function," Nucleic Acids Research 31 (13):3812-3814, 2003.
Nishi et al., "Biochemical and Genetic Analysis of the Effects of Amylose-Extender Mutation in Rice Endosperm," Plant Physiology 127:459-472 (2001).
Okagaki R. J., "Nucleotide Sequence of a Long cDNA from the Rice Waxy Gene," Plant Molecular Biology 19:513-516 (1992).

(56) References Cited

OTHER PUBLICATIONS

Puchta, "Gene Replacement by Homologous Recombination in Plants," Plant Mol. Biol. 48:173-182 (2002).
Rahman et al., "Comparison of starch-branching enzyme genes reveals evolutionary relationships among isoforms. Characterization of a gene for starch branching enzyme IIa from the wheat D genome donor Aegilops tauschii," Plant Physiology 125(3), 1314-1324,2001.
Rahman et al., GenBank Accession #AF076680, Aegilops tauschii starch branching enzyme-I (SBE-1) gene, complete cds. (May 1999).
Rahman, S. et al., "Characterisation of a Gene Encoding Wheat Endosperm Starch Branching Enzyme-I,"Theor. Appl. Genet. 98:156-163 (1999).
Rahman, S. et al., "The Major Proteins of Wheat Endosperm Starch Granules," Aust. J. Plant Physiol. 22:793-803 (1995).
Rahman, S. et al., A Complex Arrangement of Genes at a Starch Branching Enzyme I Locus in the D-genome Donor of wheat, Genome 40:465-474 (1997).
Regina et al., "Control of starch branching in barley defined through differential RNAi suppression of starch branching enzyme IIa and IIb," J. Exp. Bot. 61: 1469-1482 2010.
Regina et al., Starch branching enzyme IIb in wheat is expressed at low levels in the endosperm compared to other cereals and encoded at a non-syntenic locus, Planta 2005222:899-909, 11 pages.
Regina, (2006) "High-amylose wheat generated by RNA interference improves indices of large bowel health in rats," PNAS, vol. 103, pp. 3546-3551.
Safford et al., "Consequences of Antisense RNA Inhibition of Starch Branching Enzyme Activity on Properties of Potato Starch," Carbohydrate Polymers 35:155-168 (1998).
Saika et al., Application of gene targeting to designed mutation breeding of high-tryptophan rice. Plant Physiology 156:1269-1277, 2011.
Sathish et al., "Cloning and Anti-Sense RNA Constructs of a Starch Branching Enzyme Gene From Barley Endosperm," Photosynthesis: from Light to Biosphere vol. V. P. Mathis (ed.) pp. 313-316 (1995).
Schondelmaier et al., "Genetical Studies in the Mode of Inheritance and Localization of the amol (High Amylose) Gene in Barley," Plant Breeding 109:274-280 (1992).
Schwall, et al., "Production of Very-High-Amylose Potato Starch by Inhibition of SBE A And B," Nature Biotechnology 18:551-554 (2000).
Sestili et al., "Increasing the amylose content of durum wheat through silencing of the SBEIIa genes," BMC Plant Biology 2010 10: 144, 12 pages.
Shannon et al., "In Starch: Chemistry and Technology," Whistler et al., eds, Academic Press, Orlando, FL 25-86 (1984).
Siddiqui et al. (2008) "Germination Behavior of Wheat (*Triticum aestivum*) Varieties to Artificial Ageing Under Varying Temperature and Humidity" 40 (3) : 1121-1127.
Sidebottom et al., "Characterization of the Difference of Starch Branching Enzyme Activities in Normal and Low-Amylopectin Maize during Kernel Development," Journal of Cereal Science 27:279-287 (1998).
Slade et al., "Development of high amylose wheat through TILLING," BMC Plant Biology 201212:69, 17 pages.
Slade et al., A reverse genetic, nontransgenic approach to wheat crop improvement by TILLING, Nature Biotechnology, Jan. 2005, vol. 23 No. 1, 7 pages.
Stewart et al., "A rapid CTAB DNA isolation technique useful for rapid fingerprinting and other PCR applications," Bio Techniques 14(5):748-749, 1993.
Sun et al., "Identification of Four Starch-Branching Enzymes in Barley Endosperm: Partial Purification of Forms I, IIa and IIb," New Phytol. 137:215-222 (1997).
Sun et al., "The Two Genes Encoding Starch-Branching Enzymes IIa and IIb Are Differentially Expressed in Barley," Plant Physiology 118:37-49 (1998).

Sundberg et al., "Glycaemic Responses and Hypocholesterolaemic Effects of High-Amylose Barley Diets on Broiler Chicks," J. Sci. Food Agric. 76:457-463 (1998).
Takaoka, M. et al., "Structural characterization of high molecular weight starch granule-bound proteins in wheat (*Triticum aestivum* L.)," J. Agric. Food Chem. 45:2929-2934 (1997).
Taylor et al., PARSENSP: "A tool for the analysis of nucleotide polymorphisms," Nucleic Acids Research 31:3808-3811, 2003.
Terada at al., (2002) "Efficient Gene Targeting by Homologous Recombination in Rice," Nature Biotech. 20:1030-1034.
Tetlow IJ et al., (2004) "Recent developments in understanding the regulation of starch metabolism in higher plants," Journal of Experimental Botany 55(406):2131-2145.
Thomas, et al., "Size Constraints for Targeting Post-Transcriptional Gene Silencing and for RNA-directed Methylation in Nicotiana benthamiana Using a Potato Virus X Vector," Plant J. 25:417-425 (2001).
Topping et al., "Resistant Starch and Health—Himalaya 292, a Novel Barley Cultivar to Deliver Benefits to Consumers" Starch/Starke 55: 539-545, 2003.
Topping et al., (2001) "Short-Chain Fatty Acids and Human Colonic Function: Roles of Resistant Starch and Non-starch Polysaccharides" Physiological Review, vol. 81(3), pp. 1031-1064.
Uauy et al., "A modified TILLING approach to detect induced mutations in tetraploid and hexaploid wheat," BMC Plant Biology 9: 115,2009.
USDA, ARS, National Genetic Resources Program. Germplasm Resources Information Network (GRIN) [Online Database] National Germplasm Resources Laboratory, Beltsville, Maryland (http://www.ars-grin.gov/npgs/), GRIN System [Accession No. GSHO 2476, Jun. 23, 1997].
Van der Leij et al., "Sequence of the Structural Gene for Granule-Bound Starch Synthase of Potato (*Solanum tuberosum* L.) and Evidence for a Single Point Deletion in the amf allele," Mol. Gen. Genet. 228:240-248 (1991).
Vrinten and Nakamura, "Wheat Granule-Bound Starch Synthase I and II Are Encoded by Separate Genes That Are Expressed in Different Tissues," Plant Physiology 122:255-263 (2000).
Walker and Merritt, "Genetic Control of Abnormal Starch Granules and High Amylose Content in a Mutant of Glacier Barley," Nature 221:482-484 (1969).
Walter et al., GenBank Accession #AAB17085, Starch Synthase (Oct. 1996).
Walter et al., GenBank Accession #U66377, Triticum aestivum soluble starch synthaese mRNA, partial cds. (Oct. 1996).
Wang et al., "Variance and marker estimates of parental contribution to F2 and BC1-derived inbreds," Crop Sci. 40:659-665, 2000.
Wang et al., (2009) "Simultaneous selectioin of major and minor genes: use of QLT to increase selection efficiency of coleoptile length of wheat (*Triticum aestivum* L.)," Theor Appl Genet, 119:65-74.
Wasserman et al., "Microstructure, Thermal properties and susceptibility of the high amylose wheat starch to enzymatic hydrolysis: A new material for resistant starch (SRIII) production," Polish Jounal of Food and Nutrition Sciences vol. 13-54, No. 2, pp. 151-156 (2004).
Wei et al., "C-Type Starch from High-Amylose Rice Resistant Starch Granules Modified by Antisense RNA Inhibition of Starch Branching Enzyme," Journal of Agricultural and Food Chemistry, 58:7383-7388 (2010).
Wesley SV et al., (2001) "Construct design for efficient, effective and high-throughput gene silencing in plants." Plant J. 27(6):581-90.
Wolters AM, Visser RG., (2000) "Gene silencing in potato: allelic differences and effect of ploidy" Plant Mol Biol. 43(2-3):377-86.
Yamamori and Endo, "Variation of Starch Granule Proteins and Chromosome Mapping of Their Coding Genes in Common Wheat," Theor. Appl. Genet. 93:275-181 (1996).
Yamamori et al., "Genetic Elimination of a Starch Granule Protein, SGP-1, of Wheat Generates an Altered Starch with Apparent High Amylose," Theor. AJ2, eI. Genet. 101:21-29 (2000).

(56) References Cited

OTHER PUBLICATIONS

Yamamori, "Selection of a Wheat Lacking a Putative Enzyme for Starch Synthesis, SGP-1," Proc. 9th In Wheat Gen. Symp. 4:300-302 (1998).
Zhang et al., "High frequency targeted mutagenesis in *Arabidopsis thaliana* using zinc finger nucleases," Proc. Natl. Acad. Sci. USA 107(26): 12028-12033, 2010.
Zhang et al. (2008) "Overlapping functions of the starch synthases SSII and SSIII in amylopectin biosynthesis in *Arabidopsis*" BMC Plant Biology 8:96.
Zobel et al., Starch Gelatinization: An X-ray Diffraction Study. Cereal Chem, 1988, 65(6):443-446.
Zobel, H.F., Starch Crystal Transformations and Their Industrial Importance. Starch, 1988, 40(1):1-7.
Zwar and Chandler, α-Amylose production and leave protein synthesis in a gibberellin-responsive dwarf mutant of 'Himalya' barley (*Hordeum vulgare* L.). Planta, 1995, 197:39-48.
Botticella et al., "High Resolution Melting Analysis for the Detection of EMS Induced Mutations in Wheat Sbella Genes," Plant Biology, vol. 11, 14 pp. (2011).
Hazard et al., "Induced Mutations in the Starch Branching Enzyme II (SBEII) Genes Increased Amylose and Resistant Starch Content in Durum Wheat," Crop Sci. 52(4):1754-66 (2012).
Office Action for U.S. Appl. No. 13/668,177 (dated Dec. 18, 2014).
Office Action for U.S. Appl. No. 13/668,177 (dated Jul. 21, 2015).
Declaration Under 37 C.F.R. § 1.132 of Ahmed Regina for U.S. Appl. No. 13/668,177, dated Dec. 5, 2014.
Examination Report No. 1 for Australian Patent Application No. 2012318814, dated May 7, 2017.
Office Action for European Patent Application No. 12 775 107.1, dated Apr. 20, 2016.
Office Summons to Attend Oral Proceedings for European Patent Application No. 12775107.1, dated Oct. 4, 2017.
Stryer, "Biochemistry", 3rd Ed., New York, W.H. Freeman and Company, pp. 106-107(1988).
Williams et al., "Genome-wide Prediction of Stop Codon Readthrough During Translation in the Yeast *Sacchararomyces cerevisiae*", Nucleic Acids Research, 32 (22). 6605-6616, (2004).
Ishikawa et al., "PCR-Based Landmark Unique Gene (PLUG) Markers Effectively Assign Homoeologous Wheat Genes to A, B, and D Genomes", BMC Genomics, (2007).
International Preliminary Report on Patentability and Written Opinion for Corresponding International Patent Application No. PCT/US2012/058481, dated Apr. 8, 2014.
English Translation of Pertinent Portion of the First Office Action for China Patent Application No. 201280059762.8, dated May 27, 2015.
English Translation of Pertinent Portion of the Second Office Action for China Patent Application No. 201280059762.8, dated Apr. 7, 2016.
English Translation of Pertinent Portion of the Decision of Rejection for China Patent Application No. 201280059762.8, dated Dec. 27, 2016.
English Translation of Pertinent Portion of the Notification of Reexamination for China Patent Application No. 201280059762.8, dated Sep. 29, 2017.
International Search Report for PCT App. No. PCT/US2012/058481 dated Feb. 15, 2013.
NCBI GenBank Accession FM865435, Aug. 22, 2012.
NCBI GenBank Accession CAR95900, Aug. 27, 2012.
NCBI GenBank Accession AF338431, Mar. 27, 2001.
NCBI GenBank Accession AAK26821, Mar. 27, 2001.
NCBI GenBank Accession AY7 40398, Mar. 14, 2006.
NCBI GenBank Accession AAW80632, Mar. 14, 2006.
Extended European Search Report for 19151512.1 (dated Jun. 13, 2019).
Declaration of Interference under 37 C.F.R. § 41.203(d), Patent Interference 106, 110 between U.S. Pat. No. 10,246,716 to Slade et al. And U.S. Appl. No. 15/440,652 to Regina et al. (dated Apr. 24, 2019).
Fujisawa et al., "Suppression of the Heterotrimeric G Protein Causes Abnormal Morphology, Including Dwarfism, in Rice," Proc. Natl. Acad. Sci. USA 96:7575-7580 (1999).
Laby et al., "The Arabidopsis Sugar-Insensitive Mutants sis4 and sis5 are Defective in Abscisic Acid Synthesis and Response," The Plant Journal 23(5):587-596 (2000).
Salmeron et al., "Tomato Mutants Altered in Bacterial Disease Resistance Provide Evidence for a New Locus Controlling Pathogen Recognition," The Plant Cell 6:511-520 (1994).
Wu et al., "Chemical- and Irradiation-Induced Mutants of Indica Rice IR64 for Forward and Reverse Genetics," Plant Molecular Biology 59:85-97 (2005).
Declaration of Ann J. Slade, Ph.D., dated Oct. 18, 2018.
Hicks et al., "Early Flowering3 Encodes a Novel Protein that Regulates Circadian Clock Function and Flowering in Arabidopsis," Plant Cell 13:1281-92 (2001).
Oki et al., "Study of Novel d1 Alleles, Defective Mutants of the Alpha Subunit of Heterotrimeric G-protein in Rice," Genes Genet. Syst. 84:35-42 (2009).
Fitzgerald et al., "A High-Throughput Method for the Detection of Homoeologous Gene Deletions in Hexaploid Wheat," BMC Plant Biology 10:264 (2010).
Sega, "A Review of the Genetic Effects of Ethyl Methanesulfonate," Mutation Res. 134:113-42 (1984).
Leung et al., "Deletion Mutants for Functional Genomics: Progress in Phenotyping, Sequence Assignment, and Database Development," In Rice Genetics IV, 239-51, (2001).
Comai et al., "Efficient Discovery of DNA Polymorphisms in Natural Populations by Ecotilling," Plant J. 37:778-86, (2004).
Brazilian Office Action and English translation for application No.11-2014-007928-5 dated Jun. 11, 2020, 9 pages.
Examination Report for Australian Patent Application No. 12018211346, dated Dec. 6, 2019.
Office Action for Argentina Patent Application No. 20120103690, dated Oct. 1, 2019.
Examination Report for Canada Application No. 2,850,490 (dated Sep. 18, 2019).
Mikulikova and Kraic, "Natural Sources of Health-Promoting Starch", J. Food Nutrition Res. 45:69-76 (2006).
Examination Report for Canada Application No. 2,850,490 dated Dec. 7, 2020.
Monteiro de Souza and de Oliveira e Magalhaes, "Application of Microbial Alpha-Amylase in Industry—A Review," Brazilian J. of Microbiology 41:850-861 (2010).

\* cited by examiner

SEQUENCE LISTING

```
<160> NUMBER OF SEQ ID NOS: 58

<210> SEQ ID NO 1
<211> LENGTH: 6114
<212> TYPE: DNA
<213> ORGANISM: Triticum aestivum

<400> SEQUENCE: 1
caattaatat cgtccatcac tcgggttccg cgctgcattt cggccggcgg gttgagtgag      60
atctgggcca ctgaccgact cactcgctcg ctgcgcgggg atgcgacgt ttgcggtgtc     120 cggcgcgacc ctcggtgtgg cgcggcccgc cggcgccggc ggcggactgc tgccgcgatc     180
cggctcggag cggaggggcg gggtggacct gccgtcgctg ctcctcagga agaaggactc     240
```

```
ctctcgtacg cctcgctcgc tcgctccaat ctcccgtcca tttttgcccc ccttctctct    300
ccctatctgc gcgcgcatgg cctgttcgat gctgttcccc agttgatctc catcaacgag    360
agagatagct ggattaggcg atcgcctgcg tcagtgtcac ccaggccctg gtgttatcac    420
ggctttgatc atctcctccc attctgatat tttctcactc tttcttctgt tcttgctgta    480
actgcaagtt gtagcattgt ctcactattg tagtcatcct tgcattgcag gcgccgtcct    540
gagccgcgcg gcctctccag ggaaggtcct ggtgcctgac ggtgagagcg acgacttggc    600
aagtccggcg caacctgaag aattacaggt acacaccatc gtgccgggaa atcttcatac    660
aatcgttatt cacttaccaa atgccggatg aaaccaagcc gcggaggcgt caggttttga    720
gcttcttcta tcagcattgt gcagtactgc actgccttgt gcattttgtt agccgtggcc    780
ccgtgctggc tcttgggcca ctgaaaactc agatggatgt gcattctagc aagaacttca    840
cgaaataatg cactgtttgt ggtttcgtta gtctgctcta caattgctat tttcgtgctg    900
tagatacctg aagacatcga ggagcaaacg gctgaagtaa acatgacagg ggggactgca    960
gaaaaacttg aatcttcaga accgactcaa ggcattgtgg aaacaatcac tgatggtgta   1020
accaaaggag ttaaggaact agtcgtgggg gagaaaccgc gagttgtccc aaaaccagga   1080
gatgggcaga aaatatacga gattgaccca acgctgaaag attttcggag ccatcttgac   1140
taccggtaat gcctacccgc tactttcgct cattttgaat taaggtcctt tcgtcatgca   1200
aatttgggga acatcaaaga gacaaagact agggaccact atttcttaca gttcccctca   1260
tggtctgaga atatgctggg acgtagatgt ataattgatg gctacaattt gctcataatt   1320
acgatacaaa taactgtctc tgatcattgc aattacagag tggcaaactg attaaaatgt   1380
gatagatggg ttatagattt tactttgcta attcctctac caaattcctg ggaaaaaaaa   1440
tctaccagtt gggcaactta gtttcttatc tttgttgcct ctttgttttg gggaaaacac   1500
actgctaaat ttgaatgatt ttgggtatgc ctccgtggat tcaacagata cagcgaatac   1560
aggagaattc gtgctgctat tgaccaacat gaaggtggat tggaagcatt ttctcgtggt   1620
tatgaaaagc ttggatttac ccgcaggtaa atttaaagct tcagtattat gaagcgcctc   1680
cactagtcta cttgcatatc ttacaagaaa atttataatt cctgttttcg cctctctttt   1740
ttccagtgct gaaggtattg tctagttgca tatcttataa gaaaatttat gttcctgttt   1800
tccccctattt tccagtgctg aaggtatcac ttaccgagaa tgggctcctg gagcgcatgt   1860
acgtctttta agtcttaaca gacaccttcc aattcattgt taatggtcac actattcacc   1920
aactagctta ctggacttac aacttagctt actgaatact gaccagttgc tctaaattta   1980
tgatctggct tttgcatcct attacagtct gcagcattag taggtgactt caacaattgg   2040
aatccgaatg cagatactat gaccagagta tgtctacagc ttggcaatct tccacctttg   2100
cttcataact actgatacat ctatttgtat ttatttttgct gtttgcacat tccttaaagt   2160
tgagcctcaa ctatatcata tcaaaatggt ataattttgtc agtgtcttaa gcttcagcct   2220
aaagattcta ctcaaattgg tccatctttt tgagattgaa aatgagtata ttaaggatgg   2280
atgaataggt gcaacactcc cattctttgg tagaaccttc tgcattatgt gtgttttttc   2340
atctacaatg agcatatttc catgctatca gtgaaggttt gctcctattg atgccgatat   2400
ttgatatgat cttttcagga tgattatggt gtttgggaga ttttcctccc taacaatgct   2460
gatggatccc cagctattcc tcatggctca cgtgtaaagg taagctggcc aattatttag   2520
ttgaggatgt agcatttcg aactctgccc actaagggtc cctttgcctt tctgttttct   2580
```

```
agatacggat ggatactcca tctggtgtga aggattcaat ttctgcttgg atcaagttct    2640
ctgtgcaggc tccaggtgaa ataccattca atggcatata ttatgatcca cctgaagagg    2700
taagtatcga tctccattac attattaaat gaaatttcca gtgttacggt tttttaatac    2760
ccatttcgtg tctcactgac atgtgagtca agacaatact ttagaatttg aagtgacat     2820
atgcattaat tcaccttcta agggctaagg ggcaagcaac catggtgatg tttgtatgct    2880
tgtgtgtgac ttaagatctt atagctcttt tatgtgttct ctgttggtta ggatattcca    2940
ttttgacctt ttgtgaccat ttactaagga tatttacatg caaatgcagg agaagtatgt    3000
cttccaacat cctcaaccta acgaccaga gtcactgagg atttatgaat cacacattgg     3060
aatgagcagc ccagtatgtc aataagttat ttcacctgtt tctggtctga tggtctattc    3120
tatggatttt ttagttctgt tatgtattgt taacatataa catggtgcat tcacgtgaca    3180
acctcgattt tattttctaa tgttattgca atagctcggt ataatgtaac catgttacta    3240
gcttaagatg gttagggttt cccacttagg atgcatgaaa tatcgcattg gagcatctcc    3300
agcaagccat tttttttgacg gttaacagca ggagctctgc ttttcattat aggagaggga   3360
aatgctgtac agactgaagt cagtcagagc aaagtaactt agaatcattt atgggccacc    3420
ctgcacaggg cagaaggcag gcaggaacga tcctctacag ccgtcggatt gcctccatca    3480
gaggaatcct ggccgttaat catgctctgg cccagtggtc agaatgcatc aaccagactg    3540
aggtgcttgc ctccttattg gtaaaggatg cagcggtacg agcctattga acagatcctg    3600
ttcaagtaag gccgttctcc agcaagccat ttcctagctt attaatgaga gagagagaga    3660
gaggggggg ggtctgtatt ctgcgagcaa ttcaaaaact tccattgttc tgaggtgtac     3720
gcattgtagg gatctcccat tatgaagagg atatagttaa ttctttgtaa cctacttgga    3780
aacttgagtc ttgcggcatc gctaatatat tctatcatca caatacttag aggatgcatc    3840
tgaatatttt agtgggatct tgcacaggaa ccgaagataa attcatatgc taattttagg    3900
gatgaggtgc tgccaagaat taaaaggctt ggatacaatg cagtgcagat aatggcaatc    3960
caggagcatt catactatgc gagctttggg tattcacaca atccattttt ttctgttctt    4020
ttttctgtat gcgcctcttc acccatttgg agctattaca tcctaatgct tcgtgcacat    4080
agaatatttg gatataattc tttagtagac atatagtaca acaacagttg gtatttctga    4140
cttgtatgac catttttattg ttgttggctt gttccaggta ccatgttact aattttttttg   4200
caccaagtag ccgttttgga actccagagg acttaaaatc cctgatcgat agagcacatg    4260
agcttggttt gcttgttctt atggatattg ttcataggta agtagtccaa ttaattttag    4320
ctgctttact gtttatctgg tattctaaat ggcagggccg tatcgacgag tatttttcca    4380
ttctatataa ttgtgctaca tgacttcttt tttctcagat gtattaaacc agttggacat    4440
caaatgtatt tggtacatct agtaaactga cagtttcaaa gaacatcgtt ttgtaatggc    4500
aacatgattt tgatgccatag atgtggactg agaagttcag atgctatcaa gaaaattaat    4560
caactggcca tgtactcgtg gcactacata gagtttgcaa gttggaaaac tgacagcaat    4620
acctcactga taagtagcta ggccccactt gccagcttca tattagatgt tacttccctg    4680
ttgaactcat ttgaacatat tacttaaagt tcttcatttg tcctaagtca aacttcttta    4740
agtttgacca agtctactga aaaatatatc aacatctaca acaccaaatt ggcttcatta    4800
gattcacaat ttttattttg taatattagc acacctttga tgttgtagat atcagcacat    4860
ttttctacag acttggtcaa atatagagaa gtttgactta ggacaaatct agaacttcaa    4920
tcaatttgga tcagaggga tagtccatac tggttgatta tatccggtaa catcaaataa     4980
```

-continued

```
tatagataga tgtcaacact ttaacaaaaa aatcagacct tgtcaccaaa tatgtatcag    5040
accatctgtt tgctttagcc acttgttttc atatttatgt gtttgtacct aatctatttt    5100
tacttctact tggtttggtt gattttttt cagttgcatt gcttcatcaa tgattttgtg     5160
taccctgcag tcattcatca ataataccc ttgacggctt gaatggtttc gatggcactg     5220
atacacatta cttccacggt ggtccacgtg gccatcattg gatgtgggat tctcgtctat    5280
tcaactatgg gagttgggaa gtatgtagct ctgacttctg tcaccatatt tggctaactg    5340
ttcctgttaa atctgttctt acacatgtcg atattctatt cttatgtagg tattgagatt    5400
cttactgtca aacgcgagat ggtggcttga agaatataag tttgatggat ttcgatttga    5460
tggggtgacc tccatgatgt atactcacca tggattacaa gtaagtcatc aagtggtttc    5520
agtaactttt ttagggcact gaaataattg ctatgcatca taacatgtat catgatcagg    5580
acttgtgcta cggagtctta gatagttccc tagtacgctt gtacaatttt acctgatgag    5640
atcatggacg attcgaagtg attattattt attttcttc taagtttgct tcttgttcta     5700
gatgacattt actgggaact atggcgagta ttttggattt gctactgatg ttgacgcggt    5760
agtttacttg atgctggtca acgatctaat tcatggactt catcctgatg ctgtatccat    5820
tggtgaagat gtaagtgctt acagtattta tgattttaa ccagttaagt agttttattt     5880
tgggatcagg ctgttactct ttttgttagg ggtaagatct ctcttttcat aacaatgcta    5940
atttatacct tgtatgataa tgcatcactt aggtaatttg aaaagtgcaa ggccattcaa    6000
gcttacgagc atatttttg atggctgtaa tttatttgat agtatgcttg tttgggtttt     6060
tcagtaaatg ggagtgtgtg actaatgttg cattagaaat gggcaacctt gtca          6114
```

<210> SEQ ID NO 2
<211> LENGTH: 527
<212> TYPE: PRT
<213> ORGANISM: Triticum aestivum

<400> SEQUENCE: 2

```
Met Ala Thr Phe Ala Val Ser Gly Ala Thr Leu Gly Val Ala Arg Pro
 1               5                  10                  15

Ala Gly Ala Gly Gly Gly Leu Leu Pro Arg Ser Gly Ser Glu Arg Arg
             20                  25                  30

Gly Gly Val Asp Leu Pro Ser Leu Leu Leu Arg Lys Lys Asp Ser Ser
         35                  40                  45

Arg Ala Val Leu Ser Arg Ala Ala Ser Pro Gly Lys Val Leu Val Pro
     50                  55                  60

Asp Gly Glu Ser Asp Asp Leu Ala Ser Pro Ala Gln Pro Glu Glu Leu
 65                  70                  75                  80

Gln Ile Pro Glu Asp Ile Glu Glu Gln Thr Ala Glu Val Asn Met Thr
                 85                  90                  95

Gly Gly Thr Ala Glu Lys Leu Glu Ser Ser Glu Pro Thr Gln Gly Ile
            100                 105                 110

Val Glu Thr Ile Thr Asp Gly Val Thr Lys Gly Val Lys Glu Leu Val
        115                 120                 125

Val Gly Glu Lys Pro Arg Val Val Pro Lys Pro Gly Asp Gly Gln Lys
    130                 135                 140

Ile Tyr Glu Ile Asp Pro Thr Leu Lys Asp Phe Arg Ser His Leu Asp
145                 150                 155                 160

Tyr Arg Tyr Ser Glu Tyr Arg Arg Ile Arg Ala Ala Ile Asp Gln His
                165                 170                 175
```

Glu Gly Gly Leu Glu Ala Phe Ser Arg Gly Tyr Lys Leu Gly Phe
                180                 185                 190

Thr Arg Ser Ala Glu Gly Ile Thr Tyr Arg Glu Trp Ala Pro Gly Ala
            195                 200                 205

His Ser Ala Ala Leu Val Gly Asp Phe Asn Asn Trp Asn Pro Asn Ala
        210                 215                 220

Asp Thr Met Thr Arg Asp Asp Tyr Gly Val Trp Glu Ile Phe Leu Pro
225                 230                 235                 240

Asn Asn Ala Asp Gly Ser Pro Ala Ile Pro His Gly Ser Arg Val Lys
            245                 250                 255

Ile Arg Met Asp Thr Pro Ser Gly Val Lys Asp Ser Ile Ser Ala Trp
        260                 265                 270

Ile Lys Phe Ser Val Gln Ala Pro Gly Glu Ile Pro Phe Asn Gly Ile
        275                 280                 285

Tyr Tyr Asp Pro Pro Glu Glu Glu Lys Tyr Val Phe Gln His Pro Gln
        290                 295                 300

Pro Lys Arg Pro Glu Ser Leu Arg Ile Tyr Glu Ser His Ile Gly Met
305                 310                 315                 320

Ser Ser Pro Glu Pro Lys Ile Asn Ser Tyr Ala Asn Phe Arg Asp Glu
            325                 330                 335

Val Leu Pro Arg Ile Lys Arg Leu Gly Tyr Asn Ala Val Gln Ile Met
        340                 345                 350

Ala Ile Gln Glu His Ser Tyr Tyr Ala Ser Phe Gly Tyr His Val Thr
        355                 360                 365

Asn Phe Phe Ala Pro Ser Ser Arg Phe Gly Thr Pro Glu Asp Leu Lys
        370                 375                 380

Ser Leu Ile Asp Arg Ala His Glu Leu Gly Leu Leu Val Leu Met Asp
385                 390                 395                 400

Ile Val His Ser His Ser Ser Asn Asn Thr Leu Asp Gly Leu Asn Gly
            405                 410                 415

Phe Asp Gly Thr Asp Thr His Tyr Phe His Gly Gly Pro Arg Gly His
        420                 425                 430

His Trp Met Trp Asp Ser Arg Leu Phe Asn Tyr Gly Ser Trp Glu Val
        435                 440                 445

Leu Arg Phe Leu Leu Ser Asn Ala Arg Trp Trp Leu Glu Glu Tyr Lys
        450                 455                 460

Phe Asp Gly Phe Arg Phe Asp Gly Val Thr Ser Met Met Tyr Thr His
465                 470                 475                 480

His Gly Leu Gln Met Thr Phe Thr Gly Asn Tyr Gly Glu Tyr Phe Gly
            485                 490                 495

Phe Ala Thr Asp Val Asp Ala Val Val Tyr Leu Met Leu Val Asn Asp
        500                 505                 510

Leu Ile His Gly Leu His Pro Asp Ala Val Ser Ile Gly Glu Asp
        515                 520                 525

<210> SEQ ID NO 3
<211> LENGTH: 10219
<212> TYPE: DNA
<213> ORGANISM: Triticum aestivum

<400> SEQUENCE: 3
tgagatctgg gccactgacc gactcactcg ctgcgcgggg atggcgacgt tcgcggtgtc    60
cggcgcgacc ctcggtgtgg cgcggccccgc cagcgccggc ggcggactgc tgcgatccgg   120

```
ctcggagcgg aggggcgggg tggacttgcc gtcgctgctc ctcaggaaga aggactcctc    180
tcgtacgcct cgctccctcc aatctccccg tctgttttttg ggcccccttc tctctccctc    240
gcctctctgc gcgcgcatgg cctgttcgat gctgttcccc agttgatctc catgaacgag    300
agagatagct ggattaggcg atcgcctcag gccctggtgt taccacggct ttgatcatct    360
cctcctttca tgctgatatt ttctcactct ttcttctgtt cttgctgtaa ctgcaagttg    420
tagcattttt ttggcgaata agttgtagca ttgtctcact attgtactca tccttgcatt    480
tgcaggcgcc gtcctgagcc gcgcggcctc tccagggaag gtcctggtgc ctgacggtga    540
gagcgacgac ttggcggcca ctccagcgca acccgaagaa ttacaggtac acaccgtcgt    600
gccggaaaat cttcatgcac ccgttattca cttaccaaat atcggatgaa ccaagccgcg    660
gaggcatcag gtttcaagct tcttctatca gcattgtgca ctacttcact gccttgtgca    720
gtttgttagc tgtggccccg cgctggctct tgggccactg aaaactcaga tggatgtgca    780
ttctagcaag aacttcacaa aataatgcac tgtttgtggt ttcgttagtc tgctctacaa    840
ttgctatttt tcgtgtgctg tagatacctg aagatatcga ggagcaaacg gctgaagtga    900
acatgacagg ggggactgca gagaaacttc aatattcaga accgactcag gcattgtgg    960
aaacaatcac tgatggtgta accaaggag ttaaggaact agtcgtgggg gagaaaccgc   1020
gagttgtccc aaaaccagga gatgggcaga aaatatacga gattgaccca acgctgaaag   1080
attttcggag ccatcttgac taccggtaat gcctacccgc taatttcgct catttgaat   1140
taaggtcctt tcatcatgca aatttgggga acatcaaaga ggcaaagact agggaccact   1200
gtttcataca gttcccctca tggtctgaga atatgctggg aagtatatgt ataattgctg   1260
gctacaattg gctcataatt gcaatacaaa taactgtctc cgatcattac aattacagag   1320
tggcaaactg atgaaaatgt ggtggatggg ttatggattt tactttgcta attcctctac   1380
caaattcctg ggaaaaaat ctaccagttg ggcaacttag tttcttatct ttgttgcctt   1440
tttgttttgg ggaaaacaca ctgctaaatt tgaatgattt tgggtatgcc ttggtggatt   1500
caacagatac agcgaataca agagaattcg tgctgctatt gaccaacatg aaggtggatt   1560
ggaagcattt tctcgtggtt atgaaaagct tggatttacc cgcaggtaaa tttaaagctt   1620
tactatgaaa cgcctccact agtctaattg catatcttgt aagaaaattt ataattcctg   1680
tttttcccctc tcttttttcc agtgctgaag gtatcatcta attgcttatc ttataagaaa   1740
atttataatt cctgttttccc cccctcttttt tccagtgctg aaggtatcac ttaccgagaa   1800
tgggctcctg gagcgcatgt acgtcttaac agacaccttc taatctattg ttaatggtca   1860
ctattcacca actagcttac tgaacttaca aaatagctta ctgaatactg accagttact   1920
ctaaatttat gatctggctt ttgcatcctg ttacagtctg cagcattagt aggtgacttc   1980
aacaattgga atccaaatgc agatactatg accagagtat gtctacagct tggcaatctt   2040
ccacctttgc ttcgtaacta ctgatacatc tatttgtatt tatttaactg tttgcacgtt   2100
cgttaaagtt gagcctcaac tatatcatac caaaatggta taatttgtca gtgtcttaag   2160
cttcagccta agatcctac tgaatttagt ccatcctttt gagattgaaa atgagtatat   2220
taagggtgat tgaatacttg caacactccc atttttggt agaaccttttt gcattatgtg   2280
tgcttttcca tccacaatga gcatatttcc atgttatcag tgaaggtttg ctcctattga   2340
tgccgatatt tgatatgatc tttcgatctt ttcaggatga ttatggtgtt tgggagatct   2400
tcctccctaa caatgctgat ggatccccag ctattcctca tggctcacgt gtaaaggtaa   2460
tctggccaat tatttagtcg aggatgtaac attttcgaac tctgcctact aagggtccct   2520
```

```
tttcctctct attttctaga tacggatgga tactccatct ggtgtgaagg attcgatttc    2580
tgcttggatc aagttctctg tgcaggctcc aggtgaaata ccattcaatg gcatatatta    2640
tgatccacct gaagaggtaa gtatcaatct atgttacatt attaaatgga atttccagtg    2700
ttacagtttt ttgatacccca cttcatgtct cactgacatg tgagtcaaga caatactttc    2760
gaatttggaa gtgacatatg cattaattca ccttctaagg ctaaggggc aaccaaccat     2820 ggtgatgtgt gtatgcttgt gtgacttaag atccttatag ctcttttatat gttctctgtt   2880 ggttaggaca ttccattttg acctttgtg accatttact aaggatattt tacatgcaaa    2940
tgcaggagaa gtatgtcttc caacatcctc aacctaaacg accagagtca ctaaggattt    3000
atgaatcaca cattggaatg agcagcccgg tatgtcaata agttatttca cctgtttccg    3060
gtctgatggt ttattctatg gattttctag ttctgttatg tactgttaac ataccacacg    3120
gtgcattcac gtgacaacct cgattttatt ttctaatgtc ttcatattgg aaaatgcaca    3180
actttgcttc ctctttgtct gatcgttttt ttgtctctaa gatttccatt gcatttcgag    3240
gtagcgggca tgtgaaagtc gaatctgaat attttttgtc agagcacagt tatattaaat    3300
gccattgttg ttgcaatagc ttggtataat gtagccatgt tactagctta agaaatatcg    3360
cattggagca tctccagcaa gccatttcct accttattac tgagggggg ggggggggg     3420 agcgggttc tgtattctgc gagcgattca aaacttccac tgttctgagg tgtacgtact     3480
gtagggatct cccattatga agaggacata gttaacttt tgtaacctac ttggaaactt    3540
gagtcttgat gcatcgctac tatatactat catcacaata cttagaggat gcatctgaat    3600
attttagcgt gatcttgcac aggaaccgaa gataaattca tatgctaatt ttagggatgg    3660
ggtgctgcca agaattaaaa ggcttggata caatgcagtg cagataatgg caatccagga    3720
gcattcatac tatgcaagct ttgggtattc atacagtcca tcttttctg tttttttttt      3780 ctgtatgtgc ctcttcaccc atttcgagcc attacatcct aatgcttcgt gcacataaaa    3840
tacttggata taattcttta ttagacatat agtacaacac cacttagtat ttctgacttg    3900
tatgatcatt ttattgttgt tggcttgtta caggtaccat gttactaatt tttttgcacc    3960
aagtagccgt tttggaactc cagaggactt aaaatccttg atcgatagag cacatgagct    4020
tggtttgctt gttcttatgg atattgttca taggtaatca gtccaattta attttagttg    4080
ctttactgtt tatctggtat tgtaaatggc agggccctat cgtcgaatat ttttccaatc    4140
tatataattg tgctacatga cttatttttt ctcagatgta ttaaaccagt tggatattaa    4200
atgtatttgg tacatctagt aaactgacag tttcatagaa ttgtgttgta atggcaacac    4260
aatttgatgg catagatgtg gactgagaag ttcagatgct atcagtaatt aattaactgg    4320
ccatgtactc gtggaactac atagagtttg caagttggaa aactgacagc aatacctcac    4380
tgataagtgt ccaggccaca cttgccagct tcatattaga tgttacttcc ctgttgaact    4440
cctttgaaca tatcacttaa agttcttcaa ttgtcctaag tcaaacttct ttgactttgg    4500
ccaagtctat tgaaaaatat gtcaacatct acagcaccaa attagtttca taatttttat     4560
tttgttatat tagcacgttt tttatgctgt agatatcagc acattttttct atagacttgg    4620 tcaaatatag agaagtttga cttaggacaa atcagaactt caagcaattt ggatcagagg    4680
gaatagtcca tactgcttga ttatattttc ccaaaggagg gagtgaggag cttgacttcg    4740
gtatcatcaa atgatattga tagatgtcaa cattttaaca aaaaatcaga ccttgtcacc    4800
aaatatgcat cagaccatct gtttgcttag gcacttgctt tcatatttat gtgtttgtaa    4860
```

```
ctaatctact tttccttcta cttggtttga ttgattctat ttcagttgca ttgcttcatc    4920
aatgattttg tgtaccctgc agtcattcgt caaataatac ccttgacggt ttgaatggtt    4980
tcgatggcac tgatacacat tacttccacg gtggtccacg tggccatcat tggatgtggg    5040
attctcgtct gttcaactat gggagttggg aagtatgtag ctgcgacttc tgtcaccatg    5100
tttggctaac tgttcctgcc aatctgttct tacacgtgtc aatattctat tcttatacag    5160
gtattaagat tcttactgtc aaacgcgaga tggtggcttg aagaatataa gtttgatgga    5220
tttcgatttg atggggtgac ctccatgatg tatactcacc atggattaca agtaagtcat    5280
caagtggttt cagtaacttc ttcagggcac tgaaacaatt gctatgcatc ataacatgta    5340
tcatgatcag tacttatgct acggagtctt agatagttcc ctagtatgct tgtacaattt    5400
tacctgatga gatcatggaa gattggaagt gattgttatt atttttcctt ctaagtttgc    5460
ttcttgttct agatgacatt tactgggaac tatggcgagt attttggatt tgccactgat    5520
gttgatgcgg tggtatactt aatgctggtc aacgatctaa ttcatggact ttatcctgat    5580
gctgtatcca ttggtgaaga tgtaagtgct tacagtattt atgttttta gtattttatt    5640 ttggggatca agctgttact actcttttg ttagggtaaa atctgtcttt tcataagaat    5700
gctaatttat actccctccg tctggaaata cttgtcggag gaatgaatgt atctagacgt    5760
attttagttc tagatacatc cattttatg catttctccg tcaagtattt ccggacggag    5820
ggagtacctt gtatggtaat gcatcacata ggtaatttga aagtgcaag ggcattcaag    5880 ctgacaagca tatttgttga tggctgtaat ttatttgata gtatgcttgt ttggattttt    5940
cagtaagtgt gagtgtgtga gtaatgttat attatttatt tacttgcgga agaaatgggc    6000
aaccttgtca attgcttcag aagactaact tagattccat aaatgctgtg gaatgagag    6060 gctattccca aggacacgaa attatacgtc agtgtgttac gcacatgtat ttgtaagagc    6120
aagagcaaca tggtttaact taaattcctg cactgctatg gaatctcact gtatgttgtt    6180
agtgtacgca tccacaaaca gtaatcctg agctttcaac tcacgagaaa ataggaggct    6240
ccacttctgc cagcattagc tgttcacagt tctaatttgt gtaactctga aattgttcag    6300
gtcagtggaa tgcctacatt ttgcatccct gttccagatg gtggtgttgg ttttgactat    6360
cgcctgcata tggctgtagc agataaatgg atcgaactcc tcaagtaagt gcaggaatat    6420
tggtgattac atgcgcacaa tgatctactc cctctgtccc ataatgtaag atgttttttg    6480
acactagtgt agtgtcaaaa aacgtcctat attatgggaa ggagggagta gttcacaatt    6540
tctaaattgt aaaaagaaaa atatgtatgt gaatagctag acatttccct ggtatcagct    6600
tcaacacaag aagatttatc aaatacatga tttaaatagc aaatttcgga aatgtaatgg    6660
ctagtgtctt tatgctggat attgtacatg gcgctgtagc aggtgagtca ataaagctag    6720
cgatattttc agaaacaaaa taatcattta tatctgtata tggggaaagt gggggtatag    6780
atggtggtca ttaatcgtgt tcactttttg tcctgtataa gcacaggcag taggtaataa    6840
atttagccag ataaaataaa tcgttattag gtttacaaaa ggaatacaga gggtcatgta    6900
gcatatctag ttgtagttat tgtaaaggct gacaagaggt tcagtaaaaa aaactttatg    6960
ttgatcccgg gtatgcaaga acgcgagtaa agctcaaaca tttatagtgg ttgctgttgc    7020
ttgctgtata cttgtatctg cgcatatatg aaattactac tacacagctg ccaatctgcc    7080
atgatctgtg ttttgctttg tgctatttaa attttaaatg ctaactcaat aaatggcaat    7140
aataaactaa ctattcaacc aatttgatgg atatcagaga tttcttccct cctttagtaa    7200
cattgtgctc ctgctgctgt tctctaccgt tacaaaagct gttttcat ttttcgcatc    7260
```

```
attattttg  tgtgtgagta  atttaagcat  gtcctttgaa  gctgtgagct  gttggtactt   7320
agtacattct  tggtagtgtc  caaatatgct  gcagtctaat  ttagcatttc  tataacacag   7380
gcaaagtgac  gaatcttgga  aaatgggtga  tattgtgcac  accctaacaa  atagaaggtg   7440
gcttgagaag  tgcgtcactt  atgcagaaag  tcatgatcaa  gcactagttg  gtgacaagac   7500
tattgcattc  tggttgatgg  ataaggtact  agctgttact  tttggatcaa  agaatcaca    7560 taagatttgt  ctcatcagat  tgctcatgtt  ttcttgtgat  aaagatttgg  cccctcacc    7620 catcaccagc  tatttcccaa  ctgtcacttg  agcaaaacgt  gccatgtggc  actgtggtgg   7680
cttgtgaact  ttgacagtta  atgttgcaaa  tttctgttct  tatttatttg  attcttatgt   7740
tatcgttcat  ttattcctca  aaaaatgtta  tcgttcattt  gctcattcct  ttccgagacc   7800
agccgaagtc  acgtgtagcc  atgtgatctg  ccatctgaat  cttgagcaaa  ttttatgaag   7860
aggctaaagt  cgaacggatt  atttgcttga  atttataaat  atacagacgt  ataatcacct   7920
ggtgctttct  gaaatgatta  ccatagtgcc  tgaaggctga  aatagttttg  gcgtttcctg   7980
gacgacgccc  aaaggagtga  attttattgg  gtagatttct  ggctgagccc  tggttacaac   8040
atacattttg  gagatatgct  taataacaaa  tctgggtgtt  tggtcacgag  tctgcatcta   8100
catgctcctt  gggttttatt  atggcgtcat  ctttgtaact  agtggcaccc  ctaaggaaac   8160
attcaaaagg  aaactgttac  atcattctag  tcaggaccac  cgtactaaga  gcaaaattct   8220
gttccaattt  tatgagtttt  tgagactcca  aaatgaacat  aagtgtctca  tattttgcta   8280
attaactaca  gatgttttta  tatcacttta  gttttattt   caggacagtt  gatacttggt   8340
actgtgctgt  aagcattgat  ccgacacaga  acagcatgaa  catttcgagc  tctctttgtg   8400
caggatatgt  atgatttcat  ggctctggat  agaccttcaa  ctcctcgcat  tgatcgtggc   8460
atagcattac  ataaaatgat  caggcttgtc  accatgggtt  taggtggcga  aggctatctt   8520
aacttcatgg  gaaatgagtt  tgggcatcct  ggtcagtctt  tacaacatta  ttgcattctg   8580
catggttgtg  atttactgta  atttgaacca  tgctttgttt  tcacattgta  tgtattatgt   8640
aatctgttgc  ttccaaggag  gaagttaact  tctatttact  tggcagaatg  gatagatttt   8700
ccaagaggtc  cgcaaactct  tccaaccggc  aaagttctcc  ctggaaataa  caatagttat   8760
gataaatgcc  gccgtagatt  tgatcttgta  agttttagct  gtgctcttac  gttccctcac   8820
tagatcttta  ttggctattt  atttcttgat  gaaatcataa  tgtttgttga  tcaacattgc   8880
ttttgtagtt  ttgtagacgt  taacataaat  atgtgttaag  agttattgat  cattaagaat   8940
atcatgattt  tttttgtagg  gagatgcaga  ttttcttaga  tatcgtggta  tgcaagagtt   9000
cgaccaggca  atgcagcatc  ttgaggaaaa  atatggggta  tgtcagtatg  tcactggttt   9060
gtctttgttg  catagcaagt  cacagtttaa  cgccagtctc  ttcaaatggt  caaaagtgt    9120 agaattaatt  cctgtaatga  gatgaaaact  gcgcaaaggc  gggagctgga  attgcttttc   9180
accaattaaa  actattttct  taagcgattg  tgtattgata  cctataccaa  cactgacaat   9240
gtaactgcag  tttatgacat  ctgagcacca  gtatgtttca  cggaaacatg  aggaagataa   9300
ggtgatcatc  ttcgaaagag  gagatttggt  atttgttttc  aacttccact  ggagcaatag   9360
cttttttgac  taccgtgttg  ggtgttccaa  gcctgggaag  tacaaggtat  gcttgccttt   9420
tcattgccca  cccttcacca  gtagggttag  tgggggcttc  tacaacttt   aattccacat   9480 gtagagtttg  ttgttcgtgc  agctatcaat  ataaagaata  ggataatttg  taagaaaag    9540 aatttgttgc  tcgagatgtt  gtagtcatat  aacatcccg   aagcacatct  actattcatt   9600
```

```
catattatct acttaagggt tgttacaat ctttgtactc agttggactc actctaatac      9660
tggaactatt taccgaatct accctaatca tcctagcagt tttagagcag ccccatttgg     9720
acagtccact gggtttagtt ggtttgtgac agtttctgct atttcttaat caggtggcct     9780
tagactccga cgatgcactc tttggtggat tcagcaggct tgatcatgat gtcgactact     9840
tcacaaccgt aagtctgggc tcaagcgtca cttgactcgt ctagactcaa ctgcttacaa     9900
atctgaatca acctcccatt tgctgatgcc cttgcaggaa catccgcatg acaataggcc     9960
gcgctctttc ttggtgtaca ctcctagcag aactgcggtc gtgtatgccc ttacagagta    10020
agaaccagca gcggcttgtt acaaggcaaa gagagaactc cagggagctc gtggattgtg    10080
agcgaagcga cgggcaactg cgtgaggctg ctctaagcgc catgactggg aggggatcgt    10140
gcctcttccc ctgatgccag gaggatcaga tggataggta gcttgttggg aaaaatatgg    10200
ggtatgtcag tatgtcact                                                 10219
```

<210> SEQ ID NO 4
<211> LENGTH: 823
<212> TYPE: PRT
<213> ORGANISM: Triticum aestivum

<400> SEQUENCE: 4

```
Met Ala Thr Phe Ala Val Ser Gly Ala Thr Leu Gly Val Ala Arg Pro
1               5                   10                  15

Ala Ser Ala Gly Gly Leu Leu Arg Ser Gly Ser Glu Arg Arg Gly
            20                  25                  30

Gly Val Asp Leu Pro Ser Leu Leu Leu Arg Lys Lys Asp Ser Ser Arg
        35                  40                  45

Ala Val Leu Ser Arg Ala Ala Ser Pro Gly Lys Val Leu Val Pro Asp
    50                  55                  60

Gly Glu Ser Asp Asp Leu Ala Ala Thr Pro Ala Gln Pro Glu Glu Leu
65                  70                  75                  80

Gln Ile Pro Glu Asp Ile Glu Glu Gln Thr Ala Glu Val Asn Met Thr
                85                  90                  95

Gly Gly Thr Ala Glu Lys Leu Gln Tyr Ser Glu Pro Thr Gln Gly Ile
            100                 105                 110

Val Glu Thr Ile Thr Asp Gly Val Thr Lys Gly Val Lys Glu Leu Val
        115                 120                 125

Val Gly Glu Lys Pro Arg Val Val Pro Lys Pro Gly Asp Gly Gln Lys
    130                 135                 140

Ile Tyr Glu Ile Asp Pro Thr Leu Lys Asp Phe Arg Ser His Leu Asp
145                 150                 155                 160

Tyr Arg Tyr Ser Glu Tyr Lys Arg Ile Arg Ala Ala Ile Asp Gln His
                165                 170                 175

Glu Gly Gly Leu Glu Ala Phe Ser Arg Gly Tyr Glu Lys Leu Gly Phe
            180                 185                 190

Thr Arg Ser Ala Glu Gly Ile Thr Tyr Arg Glu Trp Ala Pro Gly Ala
        195                 200                 205

His Ser Ala Ala Leu Val Gly Asp Phe Asn Asn Trp Asn Pro Asn Ala
    210                 215                 220

Asp Thr Met Thr Arg Asp Asp Tyr Gly Val Trp Glu Ile Phe Leu Pro
225                 230                 235                 240

Asn Asn Ala Asp Gly Ser Pro Ala Ile Pro His Gly Ser Arg Val Lys
                245                 250                 255

Ile Arg Met Asp Thr Pro Ser Gly Val Lys Asp Ser Ile Ser Ala Trp
```

-continued

```
                260                 265                 270
Ile Lys Phe Ser Val Gln Ala Pro Gly Glu Ile Pro Phe Asn Gly Ile
            275                 280                 285
Tyr Tyr Asp Pro Pro Glu Glu Lys Tyr Val Phe Gln His Pro Gln
        290                 295                 300
Pro Lys Arg Pro Glu Ser Leu Arg Ile Tyr Glu Ser His Ile Gly Met
305                 310                 315                 320
Ser Ser Pro Glu Pro Lys Ile Asn Ser Tyr Ala Asn Phe Arg Asp Gly
                325                 330                 335
Val Leu Pro Arg Ile Lys Arg Leu Gly Tyr Asn Ala Val Gln Ile Met
            340                 345                 350
Ala Ile Gln Glu His Ser Tyr Tyr Ala Ser Phe Gly Tyr His Val Thr
        355                 360                 365
Asn Phe Phe Ala Pro Ser Ser Arg Phe Gly Thr Pro Glu Asp Leu Lys
    370                 375                 380
Ser Leu Ile Asp Arg Ala His Glu Leu Gly Leu Leu Val Leu Met Asp
385                 390                 395                 400
Ile Val His Ser His Ser Ser Asn Asn Thr Leu Asp Gly Leu Asn Gly
                405                 410                 415
Phe Asp Gly Thr Asp Thr His Tyr Phe His Gly Pro Arg Gly His
            420                 425                 430
His Trp Met Trp Asp Ser Arg Leu Phe Asn Tyr Gly Ser Trp Glu Val
        435                 440                 445
Leu Arg Phe Leu Leu Ser Asn Ala Arg Trp Trp Leu Glu Glu Tyr Lys
    450                 455                 460
Phe Asp Gly Phe Arg Phe Asp Gly Val Thr Ser Met Met Tyr Thr His
465                 470                 475                 480
His Gly Leu Gln Met Thr Phe Thr Gly Asn Tyr Gly Glu Tyr Phe Gly
                485                 490                 495
Phe Ala Thr Asp Val Asp Ala Val Val Tyr Leu Met Leu Val Asn Asp
            500                 505                 510
Leu Ile His Gly Leu Tyr Pro Asp Ala Val Ser Ile Gly Glu Asp Val
        515                 520                 525
Ser Gly Met Pro Thr Phe Cys Ile Pro Val Pro Asp Gly Gly Val Gly
    530                 535                 540
Phe Asp Tyr Arg Leu His Met Ala Val Ala Asp Lys Trp Ile Glu Leu
545                 550                 555                 560
Leu Lys Gln Ser Asp Glu Ser Trp Lys Met Gly Asp Ile Val His Thr
                565                 570                 575
Leu Thr Asn Arg Arg Trp Leu Glu Lys Cys Val Thr Tyr Ala Glu Ser
            580                 585                 590
His Asp Gln Ala Leu Val Gly Asp Lys Thr Ile Ala Phe Trp Leu Met
        595                 600                 605
Asp Lys Asp Met Tyr Asp Phe Met Ala Leu Asp Arg Pro Ser Thr Pro
    610                 615                 620
Arg Ile Asp Arg Gly Ile Ala Leu His Lys Met Ile Arg Leu Val Thr
625                 630                 635                 640
Met Gly Leu Gly Gly Glu Gly Tyr Leu Asn Phe Met Gly Asn Glu Phe
                645                 650                 655
Gly His Pro Glu Trp Ile Asp Phe Pro Arg Gly Pro Gln Thr Leu Pro
            660                 665                 670
Thr Gly Lys Val Leu Pro Gly Asn Asn Asn Ser Tyr Asp Lys Cys Arg
        675                 680                 685
```

```
Arg Arg Phe Asp Leu Gly Asp Ala Asp Phe Leu Arg Tyr Arg Gly Met
        690                 695                 700

Gln Glu Phe Asp Gln Ala Met Gln His Leu Glu Lys Tyr Gly Phe
705                 710                 715                 720

Met Thr Ser Glu His Gln Tyr Val Ser Arg Lys His Glu Glu Asp Lys
                725                 730                 735

Val Ile Ile Phe Glu Arg Gly Asp Leu Val Phe Val Phe Asn Phe His
            740                 745                 750

Trp Ser Asn Ser Phe Phe Asp Tyr Arg Val Gly Cys Ser Lys Pro Gly
        755                 760                 765

Lys Tyr Lys Val Ala Leu Asp Ser Asp Ala Leu Phe Gly Gly Phe
770                 775                 780

Ser Arg Leu Asp His Asp Val Asp Tyr Phe Thr Thr Glu His Pro His
785                 790                 795                 800

Asp Asn Arg Pro Arg Ser Phe Leu Val Tyr Thr Pro Ser Arg Thr Ala
                805                 810                 815

Val Val Tyr Ala Leu Thr Glu
            820

<210> SEQ ID NO 5
<211> LENGTH: 11475
<212> TYPE: DNA
<213> ORGANISM: Aegilops tauschii
<220> FEATURE:
<221> NAME/KEY: misc_feature
<222> LOCATION: (4795)..(4795)
<223> OTHER INFORMATION: n is a, c, g, or t
<220> FEATURE:
<221> NAME/KEY: misc_feature
<222> LOCATION: (4973)..(4973)
<223> OTHER INFORMATION: n is a, c, g, or t
<220> FEATURE:
<221> NAME/KEY: misc_feature
<222> LOCATION: (5078)..(5079)
<223> OTHER INFORMATION: n is a, c, g, or t
<220> FEATURE:
<221> NAME/KEY: misc_feature
<222> LOCATION: (5082)..(5082)
<223> OTHER INFORMATION: n is a, c, g, or t
<220> FEATURE:
<221> NAME/KEY: misc_feature
<222> LOCATION: (7010)..(7010)
<223> OTHER INFORMATION: n is a, c, g, or t
<220> FEATURE:
<221> NAME/KEY: misc_feature
<222> LOCATION: (7327)..(7327)
<223> OTHER INFORMATION: n is a, c, g, or t
<220> FEATURE:
<221> NAME/KEY: misc_feature
<222> LOCATION: (7381)..(7381)
<223> OTHER INFORMATION: n is a, c, g, or t
<220> FEATURE:
<221> NAME/KEY: misc_feature
<222> LOCATION: (7384)..(7384)
<223> OTHER INFORMATION: n is a, c, g, or t
<220> FEATURE:
<221> NAME/KEY: misc_feature
<222> LOCATION: (7819)..(7819)
<223> OTHER INFORMATION: n is a, c, g, or t
<220> FEATURE:
<221> NAME/KEY: misc_feature
<222> LOCATION: (8189)..(8189)
<223> OTHER INFORMATION: n is a, c, g, or t

<400> SEQUENCE: 5
agaaacacct ccatttaga ttttttttt gttcttttcg acggtgggt cgtggagaga      60 ttagcgtcta gttttcttaa aagaacaggc catttaggcc ctgctttaca aaaggctcaa    120
```

```
ccagtccaaa acgtctgcta ggatcaccag ctgcaaagtt aagcgcgaga ccaccaaaac      180
aggcgcattc gaactggaca gacgctcacg caggagccca gcaccacagg cttgagcctg      240
acagcggacg tgagtgcgtg acacatgggg tcatctatgg gcgtcggagc aaggaagaga      300
gacgcacatg aacaccatga tgatgctatc aggcctgatg gagggagcaa ccatgcacct      360
tttcccctct ggaaattcat agctcacact ttttttttaat ggaagcaaga gttggcaaac     420
acatgcattt tcaaacaagg aaaattaatt ctcaaaccac catgacatgc aattctcaaa      480
ccatgcaccg acgagtccat gcgaggtgga aacgaagaac tgaaaatcaa catcccagtt      540
gtcgagtcga aagaggatg acactgaaag tatgcgtatt acgatttcat ttacatacat       600
gtacaaatac ataatgtacc ctacaatttg ttttttggag cagagtggtg tggtcttttt      660
tttttacacg aaaatgccat agctggcccg catgcgtgca gatcggatga tcggtcggag      720
acgacggaca atcagacact caccaactgc ttttgtctgg gacacaataa atgttttttgt     780 aaacaaaata aatacttata aacgagggta ctagaggccg ctaacggcat ggccaggtaa      840
acgcgctccc agccgttggt ttgcgatctc gtcctcccgc acgcagcgtc gcctccaccg      900
tccgtccgtc gctgccacct ctgctgtgcg cgcgcacgaa gggaggaaga acgaacgccg      960
cacacacact cacacacggc acactccccg tgggtcccct ttccggcttg gcgtctatct     1020
cctctccccc gcccatcccc atgcactgca ccgtacccgc cagcttccac ccccgccgca     1080
cacgttgctc ccccttctca tcgcttctca attaatatct ccatcactcg ggttccgcgc     1140
tgcatttcgg ccggcgggtt gagtgagatc tgggcgactg gctgactcaa tcactacgcg     1200
gggatggcga cgttcgcggt gtccggcgcg actctcggtg tggcgcgggc cggcgtcgga     1260
gtggcgcggg ccggctcgga gcggaggggc ggggcggact tgccgtcgct gctcctcagg     1320
aagaaggact cctctcgtac gcctcgctct ctcgaatctc ccccgtctgg ctttggctcc     1380
ccttctctct cctctgcgcg cgcatggcct gttcgatgct gttccccaat tgatctccat     1440
gagtgagaga gatagctgga ttaggcgatc gcgcttcctg aacctgtatt ttttcccccg     1500
cggggaaatg cgttagtgtc acccaggccc tggtgttacc acggctttga tcattcctcg     1560
tttcattctg atatatattt tctcattctt tttcttcctg ttcttgctgt aactgcaagt     1620
tgtggcgttt tttcactatt gtagtcatcc ttgcatttg caggcgccgt cctgagccgc      1680
gcggcctctc cagggaaggt cctggtgcct gacggcgaga gcgacgactt ggcaagtccg     1740
gcgcaacctg aagaattaca ggtacacaca ctcgtgccgg taaatcttca tacaatcgtt     1800
attcacttac caaatgccgg atgaaaccaa ccacggatgc gtcaggtttc gagcttcttc     1860
tatcagcatt gtgcagtact gcactgcctt gttcattttg ttagccttgg ccccgtgctg     1920
gctcttgggc cactgaaaaa atcagatgga tgtgcattct agcaagaact tcacaacata     1980
atgcaccgtt tgggtttcg tcagtctgct ctacaattgc tatttttcgt gctgtagata      2040
cctgaagata tcgaggagca aacggcgaaa gtgaacatga caggggggac tgcagagaaa     2100
cttcaatctt cagaaccgac tcagggcatt gtggaaacaa tcactgatgg tgtaaccaaa     2160
ggagttaagg aactagtcgt gggggagaaa ccgcgagttg tcccaaaacc aggagatggg     2220
cagaaaatat acgagattga cccaacactg aaagattttc ggagccatct tgactaccgg     2280
taatgcctac ccgctgcttt cgctcatttt gaattaaggt cctttcatca tgcaaatttg     2340
gggaacatca aagagacaaa gactagggac caccatttca tacagatccc ttcgtggtct     2400
gagaatatgc tgggaagtaa atgtataatt gatggctaca atttgctcaa aattgcaata     2460
```

```
cgaataactg tctccgatca ttacaattaa agagtggcaa actgatgaaa atgtggtgga   2520
tgggttatag attttacttt gctaattcct ctaccaaatt cctagggggg aaatctacca   2580
gttgggaaac ttagtttctt atctttgtgg cctttttgtt ttggggaaaa cacattgcta   2640
aattcgaatg attttgggta tacctcggtg gattcaacag atacagcgaa tacaagagaa   2700
ttcgtgctgc tattgaccaa catgaaggtg gattggaagc attttctcgt ggttatgaaa   2760
agcttggatt tacccgcagg taaatttaaa gctttattat tatgaaacgc ctccactagt   2820
ctaattgcat atcttataag aaaatttata attcctgttt tcccctctct tttttccagt   2880
gctgaaggta tcgtctaatt gcatatctta taagaaaatt tatattcctg ttttcccta   2940 ttttccagtg ctgaaggtat cacttaccga gaatgggctc ctggagcgca tgttatgttc   3000
ttttaagttc cttaacgaga caccttccaa tttattgtta atggtcacta ttcaccaact   3060
agcttactgg acttacaaat tagcttactg aatactgacc agttactata aatttatgat   3120
ctggcttttg caccctgtta cagtctgcag cattagtagg tgacttcaac aattggaatc   3180
caaatgcaga tactatgacc agagtatgtc tacagcttgg caattttcca cctttgcttc   3240
ataactactg atacatctat ttgtatttat ttagctgttt gcacattcct taaagttgag   3300
cctcaactac atcatatcaa aatggtataa tttgtcagtg tcttaagctt cagcccaaag   3360
attctactga atttagtcca tcttttgag attgaaaatg agtatattaa ggatgaatga   3420
atacgtgcaa cactcccatc tgcattatgt gtgcttttcc atctacaatg agcatatttc   3480
catgctatca gtgaaggttt gctcctattg atgcagatat ttgatatggt cttttcagga   3540
tgattatggt gtttgggaga ttttcctccc taacaacgct gatggatcct cagctattcc   3600
tcatggctca cgtgtaaagg taagctggcc aattatttag tcgaggatgt agcattttcg   3660
aactctgcct actaagggtc ccttttcctc tctgtttttt agatacggat ggatactcca   3720
tccggtgtga aggattcaat ttctgcttgg atcaagttct ctgtgcaggc tccaggtgaa   3780 ataccttca atggcatata ttatgatcca cctgaagagg taagtatcga tctacattac   3840
attattaaat gaaatttcca gtgttacagt ttttttaatac ccacttctta ctgacatgtg   3900
agtcaagaca atactttga atttggaagt gacatatgca ttaattcacc ttctaagggc   3960 taagggggcaa ccaaccttgg tgatgtgtgt atgcttgtgt gtgacataag atcttatagc   4020
tcttttatgt gttctctgtt ggttaggata ttccattttg ccttttgtg accatttact   4080 aaggatattt acatgcaaat gcaggagaag tatgtcttcc aacatcctca acgtaaacga   4140
ccagagtcac taaggattta tgaatcacac attggaatga gcagcccggt atgtcaataa   4200
gttatttcac ctgtttctgg tctgatggtt tattctatgg attttctagt tctgttatgt   4260
actgttaaca tattacatgg tgcattcact tgacaacctc gatttatttt tctaatgtct   4320
tcatattggc aagtgcaaaa ctttgcttcc tctttgtctg cttgttcttt tgtcttctgt   4380
aagatttcca ttgcatttgg aggcagtggg catgtgaaag tcatatctat ttttttttg   4440 tcagagcata gttatatgaa ttccattgtt gttgcaatag ctcggtataa tgtaaccatg   4500
ttactagctt aagatttccc acttaggatg taagaaatat tgcattggag cgtctccagc   4560
aagccatttc ctaccttatt aatgagagag agacaagggg gggggggggg gggggttcc   4620 cttcattatt ctgcgagcga ttcaaaaact tccattgttc tgaggtgtac gtactgcagg   4680
gatctcccat tatgaagagg atatagttaa ttctttgtaa cctacttgga aacttgagtc   4740
ttgaggcatc gctaatatat actatcatca caatacttag aggatgcatc tgaanatttt   4800
agtgtgatct tgcacaggaa ccgaagataa attcatatgc taattttagg gatgaggtgt   4860
```

```
tgccaagaat taaaaggctt ggatacaatg cagtgcagat aatggcaatc caggagcatt    4920
catactatgc aagctttggg tattcacaca atccattttt ttctgtatac acntcttcac    4980
ccatttggag ctattacatc ctaatgcttc atgcacataa aatatttgga tataatcctt    5040
tattagatat atagtacaac tacacttagt attctganna anaagatcat tttattgttg    5100
ttggcttgtt ccaggtacca tgttactaat ttttttgcac caagtagccg ttttggaact    5160
ccagaggact taaaatcctt gatcgataga gcacatgagc ttggtttgct tgttcttatg    5220
gatattgttc ataggtaatt agtccaattt aattttagct gttttactgt ttatctggta    5280
ttctaaaggg aaattcaggc aattatgata cattgtcaaa agctaagagt ggcgaaagtg    5340
aaatgtcaaa atctagagtg gcataaggaa aattggcaaa aactagagtg gcaaaaataa    5400
aattttccca tcctaaatgg cagggcccta tcgccgaata ttttttccatt ctatataatt    5460 gtgctacgtg acttcttttt tctcagatgt attaaaccag ttggacatga aatgtatttg    5520
gtacatgtag taaactgaca gttccataga atatcgtttt gtaatggcaa cacaatttga    5580
tgccatagat gtggattgag aagttcagat gctatcaata gaattaatca actggccatg    5640
tactcgtggc actacatata gtttgcaagt tggaaaactg acagcaatac ctcactgata    5700
agtggccagg ccccacttgc cagcttcata ctagatgtta cttccctgtt gaattcattt    5760
gaacatatta cttaaagttc ttcatttgtc ctaagtcaaa cttctttaag tttgaccaag    5820
tctattggaa aatatatcaa catctacaac accaaattac tttgatcaga ttaacaattt    5880
ttattttatt atattagcac atctttgatg ttgtagatat cagcacattt ttctatagac    5940
ttggtcaaat atagagaagt ttgacttagg acaaatctag aacttcaatc aatttggatc    6000
agagggaaca tcaaataata tagatagatg tcaacacttc aacaaaaaaa tcagaccttg    6060
tcaccatata tgcatcagac catctgtttg ctttagccac ttgctttcat atttatgtgt    6120
ttgtacctaa tctacttttc cttctacttg gtttggttga ttctatttca gttgcattgc    6180
ttcatcaatg attttgtgta ccctgcagtc attcgtcaaa taatacccctt gacggtttga    6240 atggtttcga tggcactgat acacattact tccacggtgg tccacgcggc catcattgga    6300
tgtgggattc tcgtctattc aactatggga gttgggaagt atgtagctct gacttctgtc    6360
accatatttg gctaactgtt cctgttaatc tgttcttaca catgttgata ttctattctt    6420
atgcaggtat tgagattctt actgtcaaac gcgagatggg ggcttgaaga atataagttt    6480
gatggatttc gatttgatgg ggtgacctcc atgatgtata ctcaccatgg attacaagta    6540
agtcatcaag tggtttcagt aactttttta gggcactgaa acaattgcta tgcatcataa    6600
catgtatcat gatcaggact tgtgctacgg agtcttagat agttccctag tatgcttgta    6660
caattttacc tgatgagatc atggaagatt ggaagtgatt attatttatt ttctttctaa    6720
gtttgtttct tgttctagat gacatttact gggaactatg gcgaatattt tggatttgct    6780
actgatgttc atgcggtagt ttacttgatg ctggtcaacg atctaattca tggactttat    6840
cctgatgctg tatccattgg tgaagatgta agtgcttaca gtatttatga ttttttaacta    6900 gttaagtagt tttatttgg ggatcagtct gttacacttt tgttaggggg taaaatctct    6960
cttttcataa caatgctaat ttatacccttg tatgataatg catcacttan gtaatttgaa    7020
aagtgcaagg gcattcaagc ttacgagcat attttttgat ggctgtaatt tatttgatag    7080
tatgcttgtt tgggttttc aataagtggg agtgtgtgac taatgttgta ttatttattt    7140
aattgcggaa gaaatgggca accttgtcaa ttgcttcaga aggctaactt tgattccata    7200
```

```
aacgctttgg aaatgagagg ctattcccaa ggacatgaat tatacttcag tgtgttctgt    7260
acatgtattt gtaatagtgg tttaacttaa attcctgcac tgctatggaa tctcactgta    7320
tgttgtnagt gtacacatcc acaaacaagt aatcctgagc tttcaactca tgagaaaata    7380
ngangtccgc ttctgccagc attaactgtt cacagttcta atttgtgtaa ctgtgaaatt    7440
gttcaggtca gtggaatgcc tacattttgc atccctgttc cagatggtgg tgttggtttt    7500
gactaccgcc tgcatatggc tgtagcagat aaatggattg aactcctcaa gtaagtgcag    7560
gaatattggt gattacatgc gcacaatgat ctagattaca ttttctaaat ggtaaaaagg    7620
aaaatatgta tgtgaatatc tagacatttg cctgttatca gcttaatac gagaagtcaa    7680
atacatgatt taaatagcaa atctcggaaa tgtaatggct agtgtcttta tgctgggcag    7740
tgtacattgc gctgtagcag gccagtcaac acagttagca atattttcag aaacaatatt    7800
atttatatcc gtatatgang aaagttagta tataaactgt ggtcattaat tgtgttcacc    7860
ttttgtcctg tttaaggatg ggcagtaggt aataaattta gccagataaa ataaatcgtt    7920
attaggttta caaaaggaat atacagggtc atgtagcata tctagttgta attaatgaaa    7980
aggctgacaa aaggctcggt aaaaaaaact ttatgatgat ccagatagat atgcaggaac    8040
gcgactaaag ctcaaatact tattgctact acacagctgc caatctgtca tgatctgtgt    8100
tctgctttgt gctatttaga tttaaatact aactcgatac attggcaata ataaacttaa    8160
ctattcaacc aatttggtgg ataccagana tttctgccct cttgttagta atgatgtgct    8220
ccctgctgct gttctctgcc gttacaaaag ctgttttcag tttttttgcat cattattttt    8280
gtgtgtgagt agtttaagca tgttttttga agctgtgagc tgttggtact taatacattc    8340
ttggaagtgt ccaaatatgc tgcagtgtaa tttagcattt cttttaacaca ggcaaagtga    8400
cgaatcttgg aaaatgggcg atattgtgca caccctaaca aatagaaggt ggcttgagaa    8460
gtgtgtaact tatgcagaaa gtcatgatca agcactagtt ggtgacaaga ctattgcatt    8520
ctggttgatg gataaggtac tagctgttac ttttggacaa aagaattact ccctccgttc    8580
ctaaatataa gtctttgtag agattccact atggaccaca tagtatatag atgcattta    8640
gagtgtagat tcactcattt tgcttcgtat gtagtccata gtgaaatctc tacagagact    8700
tatatttagg aacggaggga gtacataatt gatttgtctc atcagattgc tagtgttttc    8760
ttgtgataaa gattggctgc ctcacccatc accagctatt tcccaactgt tacttgagca    8820
gaatttgctg aaaacgtacc atgtggtact gtggcggctt gtgaactttg acagttatgt    8880
tgcaattttc tgttcttatt tatttgattg cttatgttac cgttcatttg ctcattcctt    8940
tccgagacca gccaaagtca cgtgttagct gtgtgatctg ttatctgaat cttgagcaaa    9000
ttttattaat aggctaaaat ccaacgaatt atttgcttga atttaaatat acagacgtat    9060
agtcacctgg ctctttctta gatgattacc atagtgcctg aaggctgaaa tagttttggt    9120
gtttcttgga tgccgcctaa aggagtgatt tttattggat agattcctgg ccgagtcttc    9180
gttacaacat aacattttgg agatatgctt agtaacagct ctgggaagtt tggtcacaag    9240
tctgcatcta cacgctcctt gaggttttat tatggcgcca tctttgtaac tagtggcacc    9300
tgtaaggaaa cacattcaaa aggaaacggt cacatcattc taatcaggac caccatacta    9360
agagcaagat tctgttccaa ttttatgagt ttttgggact ccaaagggaa caaaagtgtc    9420
tcatattgtg cttataacta cagttgtttt tataccagtg tagttttatt ccaggacagt    9480
tgatacttgg tactgtgctg taaattattt atccgacata aacagcatg aacatatcaa    9540
gctctctttg tgcaggatat gtatgatttc atggctctgg ataggccttc aactcttcgc    9600
```

```
attgatcgtg gcatagcatt acataaaatg atcaggcttg tcaccatggg tttaggtggt    9660
gaaggctatc ttaacttcat gggaaatgag tttgggcatc ctggtcagtc tttacaacat    9720
tattgcattc tgcatgattg tgatttactg taatttgaac catgcttttc tttcacattg    9780
tatgtattat gtaatctgtt gcttccaagg aggaagttaa cttctattta cttggcagaa    9840
tggatagatt ttccaagagg cccacaaact cttccaaccg gcaaagttct ccctggaaat    9900
aacaatagtt atgataaatg ccgccgtaga tttgatcttg taagttttag ctgtgctatt    9960
acattccctc actagatctt tattggccat ttatttcttg atgaaatcat aatgtttgtt   10020
aggaaagatc aacattgctt ttgtagtttt gtagacgtta acataagtat gtgttgagag   10080
ttgttgatca ttaaaaatat catgattttt tgcagggaga tgcagatttt cttagatatc   10140
gtggtatgca agagttcgat caggcaatgc agcatcttga ggaaaaatat ggggtatgtc   10200
actggtttgt ctttgttgca taacaagtca cagtttaacg tcagtctctt caagtggtaa   10260
aaaaagtgta gaattaattc ctgtaatgag atgaaaactg tgcaaaggcg agctggaat    10320 tgcttttcac caaaactatt ttcttaagtg cttgtgtatt gatacatata ccagcactga   10380
caatgtaact gcagtttatg acatctgagc accagtatgt ttcacggaaa catgaggaag   10440
ataaggtgat catcctcaaa agaggagatt tggtatttgt tttcaacttc cactggagca   10500
atagcttttt tgactaccgt gttgggtgtt ccaagcctgg gaagtacaag gtatgcttgc   10560
cttttcattg tccacccttc accagtaggg ttagtggggg cttctacaac ttttaattcc   10620
acatggatag agtttgttgg tcgtgcagct atcaatataa agaatagggt aatttgtaaa   10680
gaaaagaatt tgctcgagct gttgtagcca taggaaggtt gttcttaaca gccccgaagc   10740
acataccatt cattcatatt atctacttaa gtgtttgttt caatctttat gctcagttgg   10800
actcggtcta atactagaac tattttccga atctacccta accatcctag cagttttaga   10860
gcagccccat ttggacaatt ggctgggttt ttgttagttg tgacagtttc tgctatttct   10920
taatcaggtg gccttggact ctgacgatgc actctttggt ggattcagca ggcttgatca   10980
tgatgtcgac tacttcacaa ccgtaagtct gggctcaagc gtcacttgac tcgtcttgac   11040
tcaactgctt acaaatctga atcaacttcc caattgctga tgcccttgca ggaacatccg   11100
catgacaaca ggccgcgctc tttctcggtg tacactccga gcagaactgc ggtcgtgtat   11160
gcccttacag agtaagaacc agcagcggct tgttacaagg caaagagaga actccagaga   11220
gctcgtggat cgtgagcgaa gcgacgggca acggcgcgag gctgctccaa cgccatgac    11280 tgggagggga tcgtgcctct tccccagatg ccaggaggag cagatggata ggtagcttgt   11340
tggtgagcgc tcgaaagaaa atggacgggc ctgggtgttt gttgtgctgc actgaaccct   11400
cctcctatct tgcacattcc cggttgtttt tgtacatata actaataatt gcccgtgcgc   11460
tcaacgtgaa aatcc                                                   11475
```

<210> SEQ ID NO 6
<211> LENGTH: 819
<212> TYPE: PRT
<213> ORGANISM: Aegilops tauschii

<400> SEQUENCE: 6

Met Ala Thr Phe Ala Val Ser Gly Ala Thr Leu Gly Val Ala Arg Ala
1               5                   10                  15

Gly Val Gly Val Ala Arg Ala Gly Ser Glu Arg Arg Gly Gly Ala Asp
            20                  25                  30

-continued

Leu Pro Ser Leu Leu Leu Arg Lys Lys Asp Ser Ser Arg Ala Val Leu
        35                  40                  45

Ser Arg Ala Ala Ser Pro Gly Lys Val Leu Val Pro Asp Gly Glu Ser
 50                  55                  60

Asp Asp Leu Ala Ser Pro Ala Gln Pro Glu Glu Leu Gln Ile Pro Glu
65                   70                  75                  80

Asp Ile Glu Glu Gln Thr Ala Glu Val Asn Met Thr Gly Thr Ala
                85                  90                  95

Glu Lys Leu Gln Ser Ser Glu Pro Thr Gln Gly Ile Val Glu Thr Ile
            100                 105                 110

Thr Asp Gly Val Thr Lys Gly Val Lys Glu Leu Val Val Gly Glu Lys
            115                 120                 125

Pro Arg Val Val Pro Lys Pro Gly Asp Gly Gln Lys Ile Tyr Glu Ile
            130                 135                 140

Asp Pro Thr Leu Lys Asp Phe Arg Ser His Leu Asp Tyr Arg Tyr Ser
145                 150                 155                 160

Glu Tyr Lys Arg Ile Arg Ala Ala Ile Asp Gln His Glu Gly Gly Leu
                165                 170                 175

Glu Ala Phe Ser Arg Gly Tyr Glu Lys Leu Gly Phe Thr Arg Ser Ala
            180                 185                 190

Glu Gly Ile Thr Tyr Arg Glu Trp Ala Pro Gly Ala His Ser Ala Ala
            195                 200                 205

Leu Val Gly Asp Phe Asn Asn Trp Asn Pro Asn Ala Asp Thr Met Thr
        210                 215                 220

Arg Asp Asp Tyr Gly Val Trp Glu Ile Phe Leu Pro Asn Asn Ala Asp
225                 230                 235                 240

Gly Ser Ser Ala Ile Pro His Gly Ser Arg Val Lys Ile Arg Met Asp
                245                 250                 255

Thr Pro Ser Gly Val Lys Asp Ser Ile Ser Ala Trp Ile Lys Phe Ser
            260                 265                 270

Val Gln Ala Pro Gly Glu Ile Pro Phe Asn Gly Ile Tyr Tyr Asp Pro
        275                 280                 285

Pro Glu Glu Glu Lys Tyr Val Phe Gln His Pro Gln Arg Lys Arg Pro
290                 295                 300

Glu Ser Leu Arg Ile Tyr Glu Ser His Ile Gly Met Ser Ser Pro Glu
305                 310                 315                 320

Pro Lys Ile Asn Ser Tyr Ala Asn Phe Arg Asp Glu Val Leu Pro Arg
                325                 330                 335

Ile Lys Arg Leu Gly Tyr Asn Ala Val Gln Ile Met Ala Ile Gln Glu
            340                 345                 350

His Ser Tyr Tyr Ala Ser Phe Gly Tyr His Val Thr Asn Phe Phe Ala
            355                 360                 365

Pro Ser Ser Arg Phe Gly Thr Pro Glu Asp Leu Lys Ser Leu Ile Asp
        370                 375                 380

Arg Ala His Glu Leu Gly Leu Leu Val Leu Met Asp Ile Val His Ser
385                 390                 395                 400

His Ser Ser Asn Asn Thr Leu Asp Gly Leu Asn Gly Phe Asp Gly Thr
                405                 410                 415

Asp Thr His Tyr Phe His Gly Gly Pro Arg Gly His His Trp Met Trp
            420                 425                 430

Asp Ser Arg Leu Phe Asn Tyr Gly Ser Trp Glu Val Leu Arg Phe Leu
        435                 440                 445

Leu Ser Asn Ala Arg Trp Trp Leu Glu Glu Tyr Lys Phe Asp Gly Phe

```
                    450              455              460
Arg Phe Asp Gly Val Thr Ser Met Met Tyr Thr His His Gly Leu Gln
465                 470                  475                 480

Met Thr Phe Thr Gly Asn Tyr Gly Glu Tyr Phe Gly Phe Ala Thr Asp
                    485                  490                 495

Val Asp Ala Val Val Tyr Leu Met Leu Val Asn Asp Leu Ile His Gly
                500                  505                 510

Leu Tyr Pro Asp Ala Val Ser Ile Gly Glu Asp Val Ser Gly Met Pro
            515                  520                 525

Thr Phe Cys Ile Pro Val Pro Asp Gly Gly Val Gly Phe Asp Tyr Arg
        530                  535                 540

Leu His Met Ala Val Ala Asp Lys Trp Ile Glu Leu Leu Lys Gln Ser
545                  550                  555                 560

Asp Glu Ser Trp Lys Met Gly Asp Ile Val His Thr Leu Thr Asn Arg
                    565                  570                 575

Arg Trp Leu Glu Lys Cys Val Thr Tyr Ala Glu Ser His Asp Gln Ala
                580                  585                 590

Leu Val Gly Asp Lys Thr Ile Ala Phe Trp Leu Met Asp Lys Asp Met
            595                  600                 605

Tyr Asp Phe Met Ala Leu Asp Arg Pro Ser Thr Leu Arg Ile Asp Arg
        610                  615                 620

Gly Ile Ala Leu His Lys Met Ile Arg Leu Val Thr Met Gly Leu Gly
625                  630                  635                 640

Gly Glu Gly Tyr Leu Asn Phe Met Gly Asn Glu Phe Gly His Pro Glu
                    645                  650                 655

Trp Ile Asp Phe Pro Arg Gly Pro Gln Thr Leu Pro Thr Gly Lys Val
                660                  665                 670

Leu Pro Gly Asn Asn Asn Ser Tyr Asp Lys Cys Arg Arg Phe Asp
            675                  680                 685

Leu Gly Asp Ala Asp Phe Leu Arg Tyr Arg Gly Met Gln Glu Phe Asp
        690                  695                 700

Gln Ala Met Gln His Leu Glu Glu Lys Tyr Gly Phe Met Thr Ser Glu
705                  710                  715                 720

His Gln Tyr Val Ser Arg Lys His Glu Glu Asp Lys Val Ile Ile Leu
                    725                  730                 735

Lys Arg Gly Asp Leu Val Phe Val Phe Asn Phe His Trp Ser Asn Ser
                740                  745                 750

Phe Phe Asp Tyr Arg Val Gly Cys Ser Lys Pro Gly Lys Tyr Lys Val
            755                  760                 765

Ala Leu Asp Ser Asp Asp Ala Leu Phe Gly Gly Phe Ser Arg Leu Asp
        770                  775                 780

His Asp Val Asp Tyr Phe Thr Thr Glu His Pro His Asp Asn Arg Pro
785                  790                  795                 800

Arg Ser Phe Ser Val Tyr Thr Pro Ser Arg Thr Ala Val Val Tyr Ala
                    805                  810                 815

Leu Thr Glu

<210> SEQ ID NO 7
<211> LENGTH: 4431
<212> TYPE: DNA
<213> ORGANISM: Triticum aestivum

<400> SEQUENCE: 7
atggcgtcgc cggcattcgc agtttccgcg gcgggcctcg cccggccgtc ggctcctcga    60
```

```
tccggcgggc cagagcggag ggggcgcggg gtggagctgc agtcgccatc gctgctcttc    120
ggccgcaaca agggcacccg ttcaccccgt aattattggc gctaccttcc tcactcccat    180
tctcgtttat tcgtagcggg ctgcggttca gcgaccttac gttccctcct ggtgtggtga    240
tgtctgtagg tgccgtcggc gtcggaggtt ctggatggcg cgtggtcatg cgcgcgggtg    300
ggccgtccgg ggaggtgatg atccctgacg gcggtagtgg cggaacaccg ccttccatcg    360
acggtcccgt tcagttcgac tctgatgatc tgaaggtagt ttttatttct ttccttgcta    420
gtaccttcct gcatgacaat tgaaatctaa gacaaaaaca ccatatgcga agcctacacg    480
gtaggttggt ttacaactat gtgtgccaca gttcgtctga acttttttgtc cttcacatcg    540 tgttaggttc cattcatcga tgatgaaaca agcctacagg atggaggtga agatactatt    600
tggtcttcag agacaaatca ggttactgaa gaaattgatg ctgaaggcac gagcagaatg    660
gacaaagaat catctacggg agagaaatta cgcattctgc caccaccggg aaatggacag    720
caaatatacg agattgaccc aacgctccga gactttaagt accatcttga gtatcggtat    780
gcttcgcttc tattgtgtgc actttaaact ttaaatacaa tttacagtct ttgataagat    840
gtgaatggct gcttgctgtg acacaaaact cttgaagttc gtagtcactc ttgtgtgttc    900
atggctctga ggtgacatgg taaccgaaca aaaataggaa agtggcaaga actgcaatgt    960
gagctaccga taagcaccca ttgtaattgg gtacactgat taatatatgt cttgatgggt   1020
tctatgtttt ttcagtatct atgccaattg aacaacaatg ccacttcatt tcccctgtgt   1080 tgctttgta aggatgaaac ccatatgtcc agatcaaact gtactagcag tctcactgtg   1140
ccttaatgga tcaaaaacag atacagccta tataggagaa tacgttcaga cattgatgaa   1200
cacaaaggag gcatggatgt attttcccgc ggttacgaga agtttggatt tgtgcgcagg   1260
tgaaatttct tgactagata agtatgtatc tacctttttt ctgtatcgta tctacattcc   1320
tcttcccatg cagcgctgaa ggtatcactt accgagaatg ggctcctgga gcagatgtat   1380
gttcttctga ctgtctgatc gtttacctaa gtatactagt tctatctttc aactgcttgt   1440
gaataattag tgctcatctg ctatcctaag gttggggatt ttgcacttcc cagatgaaca   1500
gcatattaag ttgcacaact agctttattt agaactaact cttgcttcca attgcagtct   1560
gcagcattag ttggcgactt caacaattgg gatccaaatg cagaccatat gagcaaagta   1620
tgcatgtagt ttcacaaata tataattttt tctttgtaaa tttgtttctt aagatctgct   1680
tactatttaa atgtggttga atatacacct tatatgtatt ccggagttga gctgtgaata   1740
tagttggaag tgtttaggag tattaaagtc actagactct attctttcac ttgcctgttg   1800
cacgagccca ttaattacta gatatcaatg ttgatgatgc ttttgttgta aacgtcaaa    1860 ttgacaacat gcatgttacc cttttatata agtaatgctg cacaaatatt tttgatgatt   1920
tagacatgat ttaatgattt tggttattgc aagacactga gcggttttac atagtaatgg   1980
tattggagta ggctgactgg ataacccgtg aactgtagct ccatgtggtt gatatggatt   2040
tacaaatgct catattcaat ttaattgttt tcagaatgac ttgggtattt gggagatttt   2100
tctgccaaac aatgcagacg gttcgccacc aattcctcac ggctcacggg tgaaggttgt   2160
tttcttctcc tcgccaactg tgttaggctc aggaacatgt tctgtattac tcacaagctc   2220
ttttgaacat ctaggtgcga atgggtactc catctgggac aaaggattca attcctgctt   2280
ggatcaagta ctccgtgcag actccaggag atataccata caatggaata tattatgatc   2340
ctcccgaaga ggtatttac ttcgtcttct gtgctttag atttcagata ttttttaattg    2400
```

| | | | | |
|---|---|---|---|---|
| gaaagaaaat | tatgatttgt | ttttctcacg | aagcttccca | agtgttattt caagttgttc | 2460 |
| tacttcttat | ttgttgttgg | catcttagtt | ttctattcac | taaccagtta tgaaattctt | 2520 |
| acatgcatgt | gcaggagaag | tatgtattca | agcatcctca | acctaaacga ccaaaatcat | 2580 |
| tgcggatata | tgaaacacat | gttggcatga | gtagcccggt | atttcatctt taccctgtat | 2640 |
| tccataaatg | aagttagcta | tatgcaattc | aagttaattt | acaatttgtt acaatggtat | 2700 |
| ttttgtgttg | ttggccttct | ttcgttttat | aagtaaaaag | cttatcataa atttatgtgt | 2760 |
| tatgccactt | ggttaataca | atctgaaaaa | tgtaactgtg | acaatctag aactagataa | 2820 |
| tacaaatctg | aaaaaacatg | ctggaatagt | gtcatttcag | tcaaatagga tgttttgaat | 2880 |
| gctcgagaga | agtactagat | tgtgtagcat | caaaagctgg | tgtccatttg ttcgaacgtt | 2940 |
| ttacttgatg | taactgtgaa | tgttacatct | tttgctacta | aagttcattt tttcactata | 3000 |
| ttacatgttt | catcaacaac | ttaattaacc | tcattcctta | caaacatttg tatttacatt | 3060 |
| tgttcctaca | taaatggtta | ttttatatat | caacttatga | atcctgaacg ttataattaa | 3120 |
| gaccgatggt | atatcaacga | ttgagataat | ttggcatatg | cggatgaatt ttgtggcttg | 3180 |
| ttatgctctt | gttttaataa | tataataaat | agattatgct | tgttggtagc ctttttacat | 3240 |
| taacacatgg | gcaattactt | gtttctttgt | gcaaccagga | accaaagatc aacacatatg | 3300 |
| caaactttcg | ggatgaggtg | cttccaagaa | ttaaaagact | tgggtacaat gcagtgcaaa | 3360 |
| taatggcaat | ccaagagcac | tcatactatg | gaagctttgg | gtagttctct gggtcgattt | 3420 |
| ctgattcttt | tagttatttt | ttgtccatgg | aacatatttc | aactttagca actatactat | 3480 |
| tatattaact | tttcagctat | tctcttcctt | ttcttactag | taaagtatgt gtgtgcaatg | 3540 |
| cacgtattag | gtaggatatt | agtggcacgt | tatattaggt | aaaatatatt tatggcacat | 3600 |
| tgatatttgc | taagatatta | attgctttct | tcgcgggaat | ggtaaaatat taattacatg | 3660 |
| acagatttca | tgggatagcg | ttgagtctaa | acatgtttat | aaccaatgat agtgatgggt | 3720 |
| aattagagcg | ttaaacatgt | ttggtgctca | acattggagc | gatttgaact gctagattac | 3780 |
| atgatttgac | ggttgagatg | gtttggatct | gcccctttgg | gtcttttgt attggtatag | 3840 |
| atgtgagaga | ctgctgcttc | ttgctacttc | ctgtgttctc | attctgagta gatatcttat | 3900 |
| gagtggacaa | ctctatgtcg | acattctgga | agtatcactg | gttgatttgg tctaaaataa | 3960 |
| catactgcac | agatagccac | ataacagtgc | gattacacac | ataatgacca tgtttgcata | 4020 |
| gagtggcggt | agtatgttcc | tcaccatact | agcataatga | tttgttatat aggagtatat | 4080 |
| catattaact | tctttccaa | tgacatggaa | gctgtaacaa | ctttcaaatc atatttgtct | 4140 |
| tttaagtgct | gcttttttcc | tgtttgacaa | ttaatacaat | accacttta tgtgttttta | 4200 |
| cttctattgc | aggtaccatg | ttaccaattt | ctttgcacca | agtagccgtt ttgggtcccc | 4260 |
| agaagattta | aaatctttga | ttgatagagc | tcacgagctt | ggcttggttg tcctcatgga | 4320 |
| tgttgttcac | aggtacttaa | tgtaatttgc | cgttggcgtg | ttaggttcac attaatctta | 4380 |
| attcttatt | tcaattccta | tggcctctct | cctagatgga | acagtaaaag c | 4431 |

<210> SEQ ID NO 8
<211> LENGTH: 416
<212> TYPE: PRT
<213> ORGANISM: Triticum aestivum

<400> SEQUENCE: 8

Met Ala Ser Pro Ala Phe Ala Val Ser Ala Ala Gly Leu Ala Arg Pro
1               5                   10                  15

-continued

Ser Ala Pro Arg Ser Gly Gly Pro Glu Arg Arg Gly Arg Gly Val Glu
              20                  25                  30

Leu Gln Ser Pro Ser Leu Leu Phe Gly Arg Asn Lys Gly Thr Arg Ser
         35                  40                  45

Pro Arg Ala Val Gly Val Gly Gly Ser Gly Trp Arg Val Val Met Arg
     50                  55                  60

Ala Gly Gly Pro Ser Gly Glu Val Met Ile Pro Asp Gly Gly Ser Gly
65                  70                  75                  80

Gly Thr Pro Pro Ser Ile Asp Gly Pro Val Gln Phe Asp Ser Asp Asp
                 85                  90                  95

Leu Lys Val Pro Phe Ile Asp Asp Glu Thr Ser Leu Gln Asp Gly Gly
                100                 105                 110

Glu Asp Thr Ile Trp Ser Ser Glu Thr Asn Gln Val Thr Glu Glu Ile
            115                 120                 125

Asp Ala Glu Gly Thr Ser Arg Met Asp Lys Glu Ser Ser Thr Gly Glu
        130                 135                 140

Lys Leu Arg Ile Leu Pro Pro Gly Asn Gly Gln Gln Ile Tyr Glu
145                 150                 155                 160

Ile Asp Pro Thr Leu Arg Asp Phe Lys Tyr His Leu Glu Tyr Arg Tyr
                165                 170                 175

Ser Leu Tyr Arg Arg Ile Arg Ser Asp Ile Asp Glu His Lys Gly Gly
            180                 185                 190

Met Asp Val Phe Ser Arg Gly Tyr Glu Lys Phe Gly Phe Val Arg Ser
        195                 200                 205

Ala Glu Gly Ile Thr Tyr Arg Glu Trp Ala Pro Gly Ala Asp Ser Ala
210                 215                 220

Ala Leu Val Gly Asp Phe Asn Asn Trp Asp Pro Asn Ala Asp His Met
225                 230                 235                 240

Ser Lys Asn Asp Leu Gly Ile Trp Glu Ile Phe Leu Pro Asn Asn Ala
                245                 250                 255

Asp Gly Ser Pro Pro Ile Pro His Gly Ser Arg Val Lys Val Arg Met
            260                 265                 270

Gly Thr Pro Ser Gly Thr Lys Asp Ser Ile Pro Ala Trp Ile Lys Tyr
        275                 280                 285

Ser Val Gln Thr Pro Gly Asp Ile Pro Tyr Asn Gly Ile Tyr Tyr Asp
290                 295                 300

Pro Pro Glu Glu Glu Lys Tyr Val Phe Lys His Pro Gln Pro Lys Arg
305                 310                 315                 320

Pro Lys Ser Leu Arg Ile Tyr Glu Thr His Val Gly Met Ser Ser Pro
                325                 330                 335

Glu Pro Lys Ile Asn Thr Tyr Ala Asn Phe Arg Asp Glu Val Leu Pro
            340                 345                 350

Arg Ile Lys Arg Leu Gly Tyr Asn Ala Val Gln Ile Met Ala Ile Gln
        355                 360                 365

Glu His Ser Tyr Tyr Gly Ser Phe Gly Tyr His Val Thr Asn Phe Phe
370                 375                 380

Ala Pro Ser Ser Arg Phe Gly Ser Pro Glu Asp Leu Lys Ser Leu Ile
385                 390                 395                 400

Asp Arg Ala His Glu Leu Gly Leu Val Val Leu Met Asp Val Val His
                405                 410                 415

<210> SEQ ID NO 9
<211> LENGTH: 4727
<212> TYPE: DNA

<213> ORGANISM: Triticum aestivum

<400> SEQUENCE: 9

```
gcctcctcat ttcgctcgcg tgggtttaag caggagacga ggcggggtca gttgggcagt      60
taggttggat ccgatccggc tgcggcggca gcgacgagat ggcgtcgccg gcattcgcag     120
tttccgcggc ggggctcgcc cggccgtcga ctcctcgatc cggcggggca gagcggaggg     180
ggcgcggggt ggagctgcag tcgccatcgc tgctcttcgg ccgcaacaag ggcacccgtt     240
caccccgtaa ttttttggcgc caccttcctc actcccattc tcgtttattc gcagcgggct    300
gcggttcagc gatcttacgt tccctactgg tgtggtgatg tctgtaggtg ccgtcagcgt     360
cggaggttct ggatggcgcg tggtcatgcg cgcgggtggg ccgtccgggg aggtgatgat     420
ccctgacggc ggtagtggcg gaacaccgcc ttccatcgac ggtcccgttc agttcgactc     480
tgatgatctg aaggtagttt ttctttttcct ttttttgcat cgatctgaag gtagttgaca    540
tatattaccc tgactaaact attactgcca ccgtatttttt atggttcgct gaaatacct    600
gtttacttgc tacggtttgc actttcattg agacgtcaga agaaattcac tgaattccta     660
taatttggta gacaccgaaa tatgtaccttt taggtcaaa atattccggc agttaagttt     720
cagttgtata caagaattca atatatata ttttctcaaa atttacaact aattggttta     780
gtttcaagtg aacgttttgg tcctttggtc gagaagtaaa ccgaaatcac tgaaattcac    840
tgaatttcag tagtggccga aacttttata gaactgaaat tcaaaatctg ctattcggcg    900
aaattatata ctaaagattt gcttatttca cacgtaggtt gcggaatatc ctctttctaa    960
tttgttgggg aatggttctt attatcttgt cagtacctgc ctgcatgaca attgaaatcc   1020
aagacaaaac accatatgcg aggcctacac gctaggttgg ttttacaact atgtgtgcca   1080
cagttcttct gaacttttttg tcttgcacat tgtgttaggt tgcattcatc gatgatgaac   1140
caagcctaca ggatgaaggt gaagatagta tttggtcttc agagacaaat caggttactg   1200
aagaaattga tgttgaaggc acgaacataa tggacaaaga tcatctacg ggggagaaat    1260
tacgcattgt gccaccacca ggaaatggac agcaaatata cgagattgac ccaacgctcc    1320
gagacttcaa gtaccatctt gagtatcggt atgattcgct tctattgtgt gcactttaaa   1380
agaatttaca gtcttcgcta agatgtgaat ggctgcttga tgtatcacga aattcttgaa   1440
gttcatagtc actcttgtgt gttcatggtt ctgaggtaac ttggtaaccg aacaaaataa    1500
ggaaagtgca agcactgcaa tgtgagctac tgataaccac ccattgtaat tgggtagact   1560
gattaatata tatgtcttca tgggctctat gtttctttttc aatatctatg ccaattgaac   1620
aacaatgctt tgtggacggg tgttctttta ccctctcctt ctatcaatag atgatacgca    1680
tactcatgcg tattctacaa aaaattgaac aacgatgcca cttcatttcc cccgtgttgc    1740
ttttgtaagg atgaaacaca tatgtccaga tcaaactgta ctagcagtct cactgtgcct    1800
taatggatca aaaacagata cagcctatat aggagaatac gttcagacat tgatgaacac    1860
gaaggaggca tggatgtatt ttcccgcggt tacgagaagt ttggatttat gcgcaggtga    1920
aatttcttga ctaaataact atgtatctac cttttctttg tattgtatca acattcctct    1980
tctcatgcag cgctgaaggt atcacttacc gagaatgggc tcctggagca gatgtatgtt    2040
cttctaacca tctgatcgtt tacctaacta tactagttct atctttcaac tacttgtgaa    2100
taattactgc tcatcagcta tcctaaggtt ggggatttg cacctcccag atgaacagca    2160
tattaagtcg cacaactagc attattaaga actaactcct gcttccaatt gcagtctgca    2220
gcattagttg gcgacttcaa caattgggat ccaaatgcag accatatgag caaagtatgc    2280
```

```
atgtagtttc acaaataata ttttctttgt agattagttt ttttttagat tggcctatct    2340
atttaaatgt ggttgaatat acaccttata tgtattccag agttgagctg taaatatagt    2400
tggttggaag tgtttaggag tttaaattca ctggactcta ttctttcact tgcctgttgc    2460
gcgagcccat tactagatat caatgttgat gatgcttttg ttgtatgagg tcgaagtgaa    2520
acatgcatgt tacccttttta tataagtaag gttgcacatg tatttttat gatctaaaca    2580
tcatttactg attttgttct tgcaagacat tcagcagttt tacataataa tggtattgga    2640
gtaggccgac tgcatacctg aactgtagct ccatgtggtt gatatagatt tacaaatgct    2700
catattcaat gtaactgttt tcagaatgac ctcggtgttt gggagatttt tctgccaaac    2760
aatgcagatg gttcgccacc aattcctcac ggctcacggg tgaaggttgt ttttttctcc    2820
ttgccaaccg tgttaggctc aggaacatgt cttgcattac tcagaagctc ttttgaaaat    2880
ctaggtgaga atggatactc catctgggat aaaggattca attcctgctt ggatcaagta    2940
ctccgtgcag actccaggag atataccata caatggaata tattatgatc ctcccgaaga    3000
ggtattttac ttcattttct gtgcttttag atttcagata ttttttaattg gaaagaaaat    3060
tatgattttt tttctcacga agcttcccaa ttgctatttc aagctgtcct acttctattt    3120
gctgttggca tcttattttt ctattcacta accagttatg aaattcctta catgcatatg    3180
caggagaagt atgtattcaa gcatcctcaa cctaagcgac caaaatcatt gcggatatat    3240
gaaacacatg ttggcatgag tagcccggta tttcatcttt accctgtatt ccataaatga    3300
aagttagcta tatgcagttt aagttaattt acaggttgtt acaatggtat ttttgtgttg    3360
ttgccccttct ttcgttttat aagtaaaaaa cttatcataa atttatttgt tatgccactt    3420
ggttaataca atctgaaaaa tgtaactgtg gacaatctag aactagataa tacaaatctg    3480
aaaaaacaag ctggaatagt gtcatttcag tcaaatagga tgttttgaat gctcgagaga    3540
agtactagat tgtgtagcat caaaagctgg tgtccatttg gtcaaatgtt taacttgatg    3600
taactgtgaa tgttacatct tttgctacta taagttcata tttttttcac tatattacat    3660
gtttcatcaa caatttagtt aacctaattc cttacaaaca tttgtattta aatttgttcc    3720
tacatgtata tttattttat atatcaactt ataaatcctg accgttataa ttaagaccaa    3780
tggtatatca atgattgaga taattttggca tatgtggatg aattttgtgg cttgttatgc    3840
tcttgttttta ataatataat aaatagatta tgcttgttgg tagccttttt acattaacac    3900
atgggcaatt acttgtttct ttgtgcaacc aggaaccaaa gatcaacaca tatgcaaact    3960
tcagggatga ggtgcttcca agaattaaaa gacttggata taatgcagtg caaataatgg    4020
caatccaaga gcactcatac tatggaagct ttgggtagtt ctctgggtcg atttctggtt    4080
cttttagtta ttttttgtcc atagaacata tttcaacttt agcaactata ctagtatatt    4140
aactttcag ctattgtctt cctttttctt atgtgagaga ctgctgcttc ttgctacttt    4200
ctgtgttctc attcagagta gacatcttat gagtggacaa ctctatgttg acattctgga    4260
agtatcactg gttggtttgg tctaaaataa catactgctc agatagccac ataacagtat    4320
gattacacac acaatgacca tgtttgcata gagtggcggt agtatgttcc tcaccatact    4380
agcataatga tttgttatat aagagtatat catattaact tcttttccaa taacatggaa    4440
gccttaacaa ctttcaaatc gttttttgtct tttaagtgct gctttttttcc tgtttgacaa    4500
ttaatacaat accactttta tgtgtttcta cttctattgc aggtaccatg ttaccaattt    4560
ctttgcacca agtagccgtt ttgggtcccc agaagattta aaatcattga ttgatagagc    4620
```

-continued

```
tcacgagctt ggcttggttg tcctcatgga tgttgttcac aggtacttaa tgtaatttgc    4680
ggttggcgtg ttaggttcac attaatctta attctttatt tcaattc                  4727
```

<210> SEQ ID NO 10
<211> LENGTH: 415
<212> TYPE: PRT
<213> ORGANISM: Triticum aestivum

<400> SEQUENCE: 10

```
Met Ala Ser Pro Ala Phe Ala Val Ser Ala Ala Gly Leu Ala Arg Pro
1               5                  10                  15

Ser Thr Pro Arg Ser Gly Gly Ala Glu Arg Arg Gly Arg Gly Val Glu
            20                  25                  30

Leu Gln Ser Pro Ser Leu Leu Phe Gly Arg Asn Lys Gly Thr Arg Ser
        35                  40                  45

Pro Arg Ala Val Ser Val Gly Gly Ser Gly Trp Arg Val Val Met Arg
    50                  55                  60

Ala Gly Gly Pro Ser Gly Glu Val Met Ile Pro Asp Gly Gly Ser Gly
65                  70                  75                  80

Gly Thr Pro Pro Ser Ile Asp Gly Pro Val Gln Phe Asp Ser Asp Asp
                85                  90                  95

Leu Lys Val Ala Phe Ile Asp Asp Glu Pro Ser Leu Gln Asp Glu Gly
            100                 105                 110

Glu Asp Ser Ile Trp Ser Ser Glu Thr Asn Gln Val Thr Glu Glu Ile
        115                 120                 125

Asp Val Glu Gly Thr Asn Ile Met Asp Lys Ser Ser Thr Gly Glu
    130                 135                 140

Lys Leu Arg Ile Val Pro Pro Gly Asn Gly Gln Gln Ile Tyr Glu
145                 150                 155                 160

Ile Asp Pro Thr Leu Arg Asp Phe Lys Tyr His Leu Glu Tyr Arg Tyr
                165                 170                 175

Ser Leu Tyr Arg Arg Ile Arg Ser Asp Ile Asp Glu His Glu Gly Gly
            180                 185                 190

Met Asp Val Phe Ser Arg Gly Tyr Glu Lys Phe Gly Phe Met Arg Ser
        195                 200                 205

Ala Glu Gly Ile Thr Tyr Arg Glu Trp Ala Pro Gly Ala Asp Ser Ala
    210                 215                 220

Ala Leu Val Gly Asp Phe Asn Asn Trp Asp Pro Asn Ala Asp His Met
225                 230                 235                 240

Ser Lys Asn Asp Leu Gly Val Trp Glu Ile Phe Leu Pro Asn Asn Ala
                245                 250                 255

Asp Gly Ser Pro Pro Ile Pro His Gly Ser Arg Val Lys Val Arg Met
            260                 265                 270

Asp Thr Pro Ser Gly Ile Lys Asp Ser Ile Pro Ala Trp Ile Lys Tyr
        275                 280                 285

Ser Val Gln Thr Pro Gly Asp Ile Pro Tyr Asn Gly Ile Tyr Tyr Asp
    290                 295                 300

Pro Pro Glu Glu Glu Lys Tyr Val Phe Lys His Pro Gln Pro Lys Arg
305                 310                 315                 320

Pro Lys Ser Leu Arg Ile Tyr Glu Thr His Val Gly Met Ser Ser Pro
                325                 330                 335

Glu Pro Lys Ile Asn Thr Ala Asn Phe Arg Asp Glu Val Leu Pro Arg
            340                 345                 350

Ile Lys Arg Leu Gly Tyr Asn Ala Val Gln Ile Met Ala Ile Gln Glu
```

-continued

```
                 355                 360                 365
His Ser Tyr Tyr Gly Ser Phe Gly Tyr His Val Thr Asn Phe Phe Ala
    370                 375                 380

Pro Ser Ser Arg Phe Gly Ser Pro Glu Asp Leu Lys Ser Leu Ile Asp
385                 390                 395                 400

Arg Ala His Glu Leu Gly Leu Val Val Leu Met Asp Val Val His
                405                 410                 415

<210> SEQ ID NO 11
<211> LENGTH: 14896
<212> TYPE: DNA
<213> ORGANISM: Aegilops tauschii
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (88)..(88)
<223> OTHER INFORMATION: n is a, c, g, or t
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (107)..(107)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (146)..(146)
<223> OTHER INFORMATION: n is a, c, g, or t
<220> FEATURE:
<221> NAME/KEY: misc_feature
<222> LOCATION: (154)..(154)
<223> OTHER INFORMATION: n is a, c, g, or t
<220> FEATURE:
<221> NAME/KEY: misc_feature
<222> LOCATION: (156)..(156)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (172)..(172)
<223> OTHER INFORMATION: n is a, c, g, or t
<220> FEATURE:
<221> NAME/KEY: misc_feature
<222> LOCATION: (206)..(206)
<223> OTHER INFORMATION: n is a, c, g, or t
<220> FEATURE:
<221> NAME/KEY: misc_feature
<222> LOCATION: (210)..(210)
<223> OTHER INFORMATION: n is a, c, g, or t
<220> FEATURE:
<221> NAME/KEY: misc_feature
<222> LOCATION: (230)..(230)
```

```
<223> OTHER INFORMATION: n is a, c, g, or t
<220> FEATURE:
<221> NAME/KEY: misc_feature
<222> LOCATION: (272)..(272)
<223> OTHER INFORMATION: n is a, c, g, or t
<220> FEATURE:
<221> NAME/KEY: misc_feature
<222> LOCATION: (274)..(274)
<223> OTHER INFORMATION: n is a, c, g, or t
<220> FEATURE:
<221> NAME/KEY: misc_feature
<222> LOCATION: (313)..(313)
<223> OTHER INFORMATION: n is a, c, g, or t
<220> FEATURE:
<221> NAME/KEY: misc_feature
<222> LOCATION: (374)..(374)
<223> OTHER INFORMATION: n is a, c, g, or t
<220> FEATURE:
<221> NAME/KEY: misc_feature
<222> LOCATION: (5514)..(5514)
<223> OTHER INFORMATION: n is a, c, g, or t
<220> FEATURE:
<221> NAME/KEY: misc_feature
<222> LOCATION: (5541)..(5541)
<223> OTHER INFORMATION: n is a, c, g, or t
<220> FEATURE:
<221> NAME/KEY: misc_feature
<222> LOCATION: (5574)..(5574)
<223> OTHER INFORMATION: n is a, c, g, or t
<220> FEATURE:
<221> NAME/KEY: misc_feature
<222> LOCATION: (5586)..(5586)
<223> OTHER INFORMATION: n is a, c, g, or t
<220> FEATURE:
<221> NAME/KEY: misc_feature
<222> LOCATION: (5602)..(5602)
<223> OTHER INFORMATION: n is a, c, g, or t
<220> FEATURE:
<221> NAME/KEY: misc_feature
<222> LOCATION: (5619)..(5619)
<223> OTHER INFORMATION: n is a, c, g, or t
<220> FEATURE:
<221> NAME/KEY: misc_feature
<222> LOCATION: (6366)..(6366)
<223> OTHER INFORMATION: n is a, c, g, or t
<220> FEATURE:
<221> NAME/KEY: misc_feature
<222> LOCATION: (6596)..(6596)
<223> OTHER INFORMATION: n is a, c, g, or t
<220> FEATURE:
<221> NAME/KEY: misc_feature
<222> LOCATION: (6604)..(6604)
<223> OTHER INFORMATION: n is a, c, g, or t
<220> FEATURE:
<221> NAME/KEY: misc_feature
<222> LOCATION: (6623)..(6623)
<223> OTHER INFORMATION: n is a, c, g, or t
<220> FEATURE:
<221> NAME/KEY: misc_feature
<222> LOCATION: (6676)..(6676)
<223> OTHER INFORMATION: n is a, c, g, or t
<220> FEATURE:
<221> NAME/KEY: misc_feature
<222> LOCATION: (6746)..(6746)
<223> OTHER INFORMATION: n is a, c, g, or t
<220> FEATURE:
<221> NAME/KEY: misc_feature
<222> LOCATION: (6787)..(6787)
<223> OTHER INFORMATION: n is a, c, g, or t
<220> FEATURE:
<221> NAME/KEY: misc_feature
<222> LOCATION: (6803)..(6803)
<223> OTHER INFORMATION: n is a, c, g, or t
<220> FEATURE:
<221> NAME/KEY: misc_feature
<222> LOCATION: (6845)..(6845)
<223> OTHER INFORMATION: n is a, c, g, or t
<220> FEATURE:
<221> NAME/KEY: misc_feature
```

```
<222> LOCATION: (6864)..(6864)
<223> OTHER INFORMATION: n is a, c, g, or t
<220> FEATURE:
<221> NAME/KEY: misc_feature
<222> LOCATION: (6877)..(6877)
<223> OTHER INFORMATION: n is a, c, g, or t
<220> FEATURE:
<221> NAME/KEY: misc_feature
<222> LOCATION: (6963)..(6963)
<223> OTHER INFORMATION: n is a, c, g, or t
<220> FEATURE:
<221> NAME/KEY: misc_feature
<222> LOCATION: (7055)..(7055)
<223> OTHER INFORMATION: n is a, c, g, or t
<220> FEATURE:
<221> NAME/KEY: misc_feature
<222> LOCATION: (7123)..(7123)
<223> OTHER INFORMATION: n is a, c, g, or t
<220> FEATURE:
<221> NAME/KEY: misc_feature
<222> LOCATION: (9161)..(9161)
<223> OTHER INFORMATION: n is a, c, g, or t
<220> FEATURE:
<221> NAME/KEY: misc_feature
<222> LOCATION: (9206)..(9206)
<223> OTHER INFORMATION: n is a, c, g, or t
<220> FEATURE:
<221> NAME/KEY: misc_feature
<222> LOCATION: (9284)..(9284)
<223> OTHER INFORMATION: n is a, c, g, or t
<220> FEATURE:
<221> NAME/KEY: misc_feature
<222> LOCATION: (10857)..(10857)
<223> OTHER INFORMATION: n is a, c, g, or t
<220> FEATURE:
<221> NAME/KEY: misc_feature
<222> LOCATION: (10861)..(10861)
<223> OTHER INFORMATION: n is a, c, g, or t
<220> FEATURE:
<221> NAME/KEY: misc_feature
<222> LOCATION: (10926)..(10926)
<223> OTHER INFORMATION: n is a, c, g, or t
<220> FEATURE:
<221> NAME/KEY: misc_feature
<222> LOCATION: (11177)..(11177)
<223> OTHER INFORMATION: n is a, c, g, or t
<220> FEATURE:
<221> NAME/KEY: misc_feature
<222> LOCATION: (11224)..(11224)
<223> OTHER INFORMATION: n is a, c, g, or t
<220> FEATURE:
<221> NAME/KEY: misc_feature
<222> LOCATION: (11336)..(11336)
<223> OTHER INFORMATION: n is a, c, g, or t
<220> FEATURE:
<221> NAME/KEY: misc_feature
<222> LOCATION: (12749)..(12749)
<223> OTHER INFORMATION: n is a, c, g, or t
<220> FEATURE:
<221> NAME/KEY: misc_feature
<222> LOCATION: (12771)..(12771)
<223> OTHER INFORMATION: n is a, c, g, or t
<220> FEATURE:
<221> NAME/KEY: misc_feature
<222> LOCATION: (12964)..(12964)
<223> OTHER INFORMATION: n is a, c, g, or t
<220> FEATURE:
<221> NAME/KEY: misc_feature
<222> LOCATION: (12984)..(12984)
<223> OTHER INFORMATION: n is a, c, g, or t
<220> FEATURE:
<221> NAME/KEY: misc_feature
<222> LOCATION: (12986)..(12986)
<223> OTHER INFORMATION: n is a, c, g, or t
<220> FEATURE:
<221> NAME/KEY: misc_feature
<222> LOCATION: (13126)..(13126)
<223> OTHER INFORMATION: n is a, c, g, or t
<220> FEATURE:
```

```
<221> NAME/KEY: misc_feature
<222> LOCATION: (13893)..(13893)
<223> OTHER INFORMATION: n is a, c, g, or t
<220> FEATURE:
<221> NAME/KEY: misc_feature
<222> LOCATION: (14086)..(14086)
<223> OTHER INFORMATION: n is a, c, g, or t
<220> FEATURE:
<221> NAME/KEY: misc_feature
<222> LOCATION: (14109)..(14109)
<223> OTHER INFORMATION: n is a, c, g, or t
<220> FEATURE:
<221> NAME/KEY: misc_feature
<222> LOCATION: (14156)..(14156)
<223> OTHER INFORMATION: n is a, c, g, or t
<220> FEATURE:
<221> NAME/KEY: misc_feature
<222> LOCATION: (14173)..(14173)
<223> OTHER INFORMATION: n is a, c, g, or t
<220> FEATURE:
<221> NAME/KEY: misc_feature
<222> LOCATION: (14517)..(14517)
<223> OTHER INFORMATION: n is a, c, g, or t
<220> FEATURE:
<221> NAME/KEY: misc_feature
<222> LOCATION: (14591)..(14591)
<223> OTHER INFORMATION: n is a, c, g, or t

<400> SEQUENCE: 11
ttttncgggg ttgcttcttc cagattcata ttcgnaaaat ttcanatgga gcttaaaaat        60
aatgtngttg agcttttttg agggtttnca aatggccaat tanaacnttg ggttttgaat       120
taattgaatc caatttngac caattnattt aagnantttt aaattggnat gnaaaacttt       180
tatttgaact attgtcgcct tggaantttn attttttgag tttaaaaggn cttgcgatat       240
ttttcttttg attgttttcc aacccatgta ananagtgcg ttaaaagagc aaggtatac        300
gccaaagaag gcncacccat tacaaagcca cataggcatg acccaactaa agaacccaaa       360
ccattgatga ttcncaatta ataaacccac caaaatcagc ttaaattaga gcaagggcat       420
tacacatgca acaaagtagg caacattttc agtgcataag actacaatag acaacaacac       480
tatctcaaca cgaccacgac aacggacaac atcgaataaa acccaaagaa cacatgaaga       540
aggcatgacg tcactgagca aggaggctac aaatccacca ccgccgggcc gacttgccac       600
caaggccata gaaggaccgt ggggtgcata ggcataaacc agagcaggag gcacatgacc       660
aacaaagaca acatcaacca cgatcaagta ccacaacagg ggaggagtga gggaaaatgc       720
catcggagac tcgaagtgga cgttggagta tttttctttg attattttca atattcaaac       780
tacacaagat caacaacaga tgagagacca aaacatttga taactacagt tggataatat       840
tggccatgat gtctgtttga tgatccgccc gagatgccaa gctttgtagc cttgcacggg       900
ctccccaaca aactgcctca ctcgattgtc aaaaaagtaa aaatgattgt agaaaaaaaa       960
actgactcac tcgtcactac cctaccgtcc tacatgacac ctggccgcaa gacgacgccg      1020
tcctcctgcc gcgcgcgtcc gcgatcacac caccgcaaaa accaaaacct cttcgccggt      1080
gcgtcccacg ctaccatcca tgcagccgtc cgcccgcgcg cgcgttgccc gcaccacccg      1140
ctggcggcca ccacgccgcc actctcgcgt gaaggctccg tccgcttcct cctagttcca      1200
ctctctctcc gtgctagcag tatatagcat ccgccctccg cccctcccca atcttagaac      1260
accccctccct ttgcctcctc atttcgctcg cgtgggttta agcaggagac gaggcgggt      1320
cagttgggca gttaggttgg atccgatccg gctgcggcgg cggcgacggg atggctgcgc      1380
cggcattcgc agtttccgcg gcggggctgg cccggccgtc ggctcctcga tccggcgggg      1440
cagagcggag ggggcgcggg gtggagctgc agtcgccatc gctgctcttc ggccgcaaca      1500
```

```
agggcacccg ttcacccccgt aattatttgc gccacctttc tcactcacat tctctcgtgt   1560
attctgtcgt gctcgccctt cgccgacgac gcgtgccgat tccgtatcgg gctgcggtgt   1620
tcagcgatct tacgtcggtt ccctcctggt gtggtgatgt ctgtaggtgc cgtcggcgtc   1680
ggaggttctg gatggcgcgt ggtcatgcgc gcgggggggc cgtccgggga ggtgatgatc   1740
cctgacggcg gtagtggcgg aacaccgcct tccatcgacg gtcccgttca gttcgattct   1800
gatgatctga aggtagtttt ttttttgcat cgatctgaag gtacttgaca tatactactg   1860
tattaccctg agtaaatact gccaccatat ttttatggtt cgcttgaaat acctgtttac   1920
ttgctacggt tttcacttc attgagacgt cggacgaaat tcactgaatt cctataattt   1980
ggtagacacc gaaatatata ctactccttc cgtcccataa tataagagcg ttttggcac    2040 cttatattat agggcggagg gagtaccttt taggtcaaaa tattgtggta gtttcaattg   2100
tatacaagaa ttcaaatatt ttttttaaaa aaaaatcaac taattggttg agtttcaagt   2160
gaagcgtttt ggtcctttgg ctgagatgta aaccgaaatc actgaaattc atagtagccg   2220
aaactttaat agaactgaaa ctcaaaatct gctatccggc gaaattctaa agatttgctt   2280
atttcacacg taggttgcag tacaccctct ttctaattta ttggggaagg ggtattatta   2340
tcttgttagt acctgcctgc atgacaattg aaatctaaga caaaacacca tatgcgaggc   2400
ctacacacgg taggttggtt tacaactatg tgtgccacag ttcgtctgaa cttttttgtcc  2460 ttcacatcgt gttaggttcc attcattgat gatgaaacaa gcctacagga tggaggtgaa   2520
gatagtattt ggtcttcaga gacaaatcag gttagtgaag aaattgatgc tgaagacacg   2580
agcagaatgg acaaagaatc atctacgagg gagaaattac gcattctgcc accaccggga   2640 aatgacagc aaatatacga gattgaccca acgctccgag actttaagta ccatcttgag    2700
tatcggtatg cttcgcttct attgtgtgca ctttaaaaac aatttacagt ctttgataag   2760
atgtgaatgg ctgcttgctg tgacacgaaa ctcttgaagt tcgtagtcac tcttgtgtgt   2820
tcatggttct gaggtaacat ggtaaccgaa caaaaatagg aaagtggcaa gcactgcaat   2880
gtgagctact gataaccacc cattgtaatt gggtacactg attaatatat atgtcttcat   2940
gggctctatt tttttttcaat atctatgcca attgaacaac aatgctttgt ggacgggtgt   3000
tcttttaccc tcttcttcta tcaatagatg atatgcatac tcatgcgtat cctacaaaaa   3060
attgaacaac aatgccactt tcccccgtgt tgcttttgta aggatgaaac acatatgtcc   3120
agatcaaact atactagcag tctaactgtg ccttaatgga tcaaaaacag atatagccta   3180
tacaggagaa tacgttcaga cattgatgaa cacgaaggag gcatggatgt atttcccgc    3240 ggttacgaga agtttggatt tatgcgcagg tgaaatttct tgactaaata actatgtatc   3300 tacctttct ttgtactcta tcaacattcc tcttcccatg cagcgctgaa ggtatcactt    3360
accgagaatg ggctcctgga gcagatgtac gttcttctaa ccatctgatc gtttacctga   3420
ctatactaat tctatctttc aactaattgt gaataattac tgctcatcag ctatcctaag   3480
gttggggatt ttgcacctcc cagatgaaca gcatattaag tcgcacaact agcattatta   3540
agaactaact cctgcttcca attgcagtct gcagcattag ttggcgactt caacaattgg   3600
gatccaaatg cagaccatat gagcaaagta tgcatgtagt ttcacaaata tatcatattt   3660
tctttgtaga tttttttttt tagatcggct tatctattta aatgtggttg aatatacacc   3720
ttatatgtac gttgagctgt aaatatagtt ggaagtgttt aggagtatta aattcactgg   3780
actctattct ttcacttgcc tgttgcacga gcccattact agatatcaat gttgatgatg   3840
```

```
cttttgttgt atgaggtcga agtgaaacat gcatgttacc ctttatata agtaaggttg   3900
cacatgtatt ttttatgatc taaacattat ttactgattt tgttcttgca agacactaag   3960
cagttttaca taataatggc gttggagcag gccgactgca catctgaact gtagctccat   4020
gtggttgata tagattacaa atgctcatat tcaatgtaac tgttttcaga atgaccttgg   4080
tgtttgggag attttttctgc caaacaatgc agatggttcg ccaccaattc ctcacggctc   4140
acgggtgaag gttgttttct tctccttgcc aacggtgtta ggctcaggaa catgtcctgt   4200
attactcaga agctcttttg aacatctagg tgagaatgga tactccatct gggataaagg   4260
attcaattcc tgcttggatc aagtactccg tgcagactcc aggagatata ccatacaatg   4320
gaatatatta tgatcctccc gaagaggtat tttacttcat cttctgtgct tttagatttc   4380
agatatttt attagaagaa aattatgatt ttttccctca cgaaccttcc caattgctat   4440
ttcaagctgt cctacttatt tgctgctggc atcttatttt tctattctct aaccagttat   4500
gaaattcctt acatgcatat gcaggagaag tatgtattca agcatcctca acctaaacga   4560
ccaaaatcat tgcggatata tgaaacacat gttggcatga gtagcccggt atttcatctt   4620
taccatgtat tccataaatg aagttagcta tatgcagttc aaatttattt acaggttgtt   4680
acaatggtat ttttgtgttg gtgcccttct ttcgttttat aagtaaaaaa cttatcataa   4740
atttatttgt tatgccgctt ggttaataca atctgaaaaa tgtaactgtg acaatctag    4800
aactagataa tacaaatctg aaaaaacatg ctggaatagt gtcatttcag tcaactagga   4860
tgttttgaat gctcaagaga agtactagtg tgtagcatca aaagctggtg tccatttgtt   4920
caaatgttta attaacacta tagtgaaaac aagtaattgc acaaagaaac aagtaattgc   4980
ccaagttcat atgtttttc actatattac atgtttcatc aacaatttaa ttaacctcat    5040
tccttacaaa catttgtatt tacatttgtt cctacatata tagttatttt atatatcaac   5100
tttataaatc atgactgtta taattaaaac cgatggtata tcaacgattg agataatttg   5160
gcatatgtgg atgaatttg tggcttgtta tgctcttgtt ttaataacat aataaataga   5220
ttatgcttgt tggtagccct tttacattaa cacatgggca attacttgtt tctttgtgca   5280
accaggaacc aaagatcgac acatatgcaa acttcaggga tgaggtgctt ccaagaatta   5340
aaagacttgg atacaatgca gtgcaaataa tggcaatcca agagcactca tactatggaa   5400
gctttgggta gttctctggg tcgatttctg gttcttttag ttatcttttg tccatagaac   5460
atatttcaac tttagcaact atactattat attaacttt cagctattgt cttnctttt     5520
cttatgtgag agactgctgc ntcttgctac ttcctgtgtt ctcattcaga gtanacatct   5580
tatgantaga caactctatg tngacattcc ggaagtatnc actggctgat tcggtctaaa   5640
ataacatact gctcagatag ccacataaca gtacgattac acacataatg accatgtttg   5700
catagagtgg cggtagtatg ttcctcacca tactagcata atgacttgtt atataagagt   5760
atatcatatt aacttctttt ccaatgacat ggaagctgta acaactttca aatcattttt   5820
gtcttttaag tgctgctttt ttcctgtttg acaattaata caataccact tttatgtgtt   5880
tttacttcta ttgcaggtac catgttacca atttctttgc accaagtagc cgttttgggt   5940
ccccagaaga tttaaaatct ttgattgata gagctcacga gcttggcttg gttgtcctca   6000
tggatgttgt tcacaggtac ttaatgtaat ttgaggttgg cgtgttaagt tcacattaat   6060
cttaattctt tatttcaatt cctatggcct ctctcctaga ttggaacagt aaaagcatca   6120
tccagttgt ataaattgct aaaagaacat tttacatgtt aagtatttc aattactatg     6180
aaacatataa atttacatac ttattgattt tacgacagaa gtaccgatct cacaagatga   6240
```

```
acaattggtt gatcacatat catttcatac tacaatacaa gaaaatgaat agagaacgag    6300
ttaatattag ccttggtaaa atcagcaact tgtttggaaa taaagtatag tgatgccagt    6360
gcaaanaaca aggcatcaag ttggtttcag ctcccacggt cggtgctagc tgtcaagggt    6420
aatttgcacg tagtcgcaca tagatttgtg tgggagtgga agtaaccac agattgtccg     6480 aggaacacgg gacacacgtc ttagccacag gtttgggctc cccttgatgc gggtagtagc    6540
tttactcctt atatgaaatt atctcaagat agatttcaat ttggggttac acttangaac    6600
tcancaagtt aaggatcaac tcnctgagtt ctatacgact gatctttgac cgagatatct    6660
tgatcaggct aagtancaaa atccaggcct tgagatgttg aacatgtcct tcattttggg    6720
ctgggtgccc ttgggcataa ggtgtngtcc ttccttcatg tgcttcttgc agcgtatgac    6780
ataaacntcc tctgagttgg tanatgcacg gttcccttg aggaaatcag gggtagtcgc     6840
atctngggaa agttggtcac ccangcatgg atcctcngcg cacaccgggc aaacacggtg    6900
aaaccacttc tcctcgacac tagctaactt gacattcaag caaactaaga atataacttt    6960
atntctaaat gaaccggaca ccctccttgt gcctgcacct acagagtaca atgccagttt    7020
tggactgaac tcttgtgttc atgtatgtgc taatnacata ggttctaacc atgattctaa    7080
atagcgcgtt ataactccac tatagtaatg ctatagcgtt tanaagatcc cgcactaagg    7140
gaccttagtc caaatacatg atcaaacatt ttacatagcg cgctatagct atttaaaact    7200
atggtcaccc gctaagaggc ataactcgct atttaaaact atggttctaa cttttaatct    7260
attttatgtc ttggtccaaa gccccttttt gttctatagc tttacctttg ggttgagatc    7320
acccttaacc cattggtaat cctggttgat ttactccatc ctttcttgcg tagctttact    7380
tttggttttt tgtttctcac agtcacgcgt caaataatac cttggacggg ttgaatggtt    7440
ttgatggcac ggatacacat tacttccatg gcggttcacg gggccatcac tggatgtggg    7500
attcccgtgt gtttaactat gggaataagg aagtatggga ctatagaatt tctattgcca    7560
tttgttatgt atttatccat taattaatcc tccaaccgat attccaacat tgttatcttt    7620
atacaggtta taaggtttct actttccaat gcaagatggt ggctagagga gtataagttt    7680
gatggtttcc gattcgatgg cgcgacctcc atgatgtata cccatcatgg attacaagta    7740
attcattgct tgattgtctt tgttctatct tgactacctg tgcaacttta ataagattac    7800
gcctagctaa tattttcttt tatgttatag tatcaatttt tatttgagct tgaaacctaa    7860 attactttt ttttgaattg ctgcgctcta ttttaggtaa cctttacagg aagctaccat     7920
gaatattttg gctttgccac tgatgtagat gcggtcgttt acttgatgct gatgaatgat    7980
ctaattcatg ggttttatcc tgaagccgta actatcggtg aagatgtaag tgtttctata    8040
gtcatctttc aatatgaatt tgttagaact attggtactt atctttttg tagtttaggc     8100 tattctgttc attcttacag gaggtgcata cagaagttgc tttagatttt gaaacgcagt    8160
gcacattgtg ccattacttt gtagctatat cgagttgaga cttgagagcc atggtaatca    8220
agttcctgac gtggcattgc attagatagt tgcatgtcta agttcctgac gtggagatag    8280
aagaaagaac gcaccccccg cgtcgctcct ctcagggcga cacgggcgga gccctcaccc    8340
ccgccgccac agggagcatc caccttctc ctctcccctc gccgccgccg gagggcaaag     8400
accgcgcggc gtcgcggcgg tgggtgcggc ctgggctggc atctggcagc ggcgatttgg    8460
cctcccctgc ccagaactgt gctgccgcgc tttgtggcag cttgggcatc ggcagtggcc    8520
cgagtctgcg gtggcggcgt gtctggcgtc cggaggtgca gcgattgtgc ggttgtgtgg    8580
```

```
ctcaggctcg gagggcgtgc gggctgccag gtccggccag atctggcctc gagtggcttc   8640
gtacggggcg gtggctgttg cgggtccgtg ggccgaggtt cgggtgtggc tgctgcttgc   8700
ccggaccggt ggtgcgtaac gatgccggag cagcgtcctc gggtcgttga agtgggcgct   8760
cctccggcag cttcaggtgg tgattcgtcg cagcgggtgg tgcactgggg gtctcggctg   8820
attgtggtgc catggtggtg gtggttgttg gcggtagcaa agtgcctggt gcacacggct   8880
agggttttgg cggatggaca gacttgatgc aatgccttag gcatagtgaa atttcagcta   8940
agtacctagc accgaccttg gtcaatgccg ccgccgctgg tgtcttagga cgttgttgcc   9000
cttgttggag gcgtgttgtg gagccccttc acctccatgg gcatttagat ctcgagctct   9060
ctgggtgaaa acgccggctt tggctttggc cggagtgggc ggtggcggcg taaccgtcgc   9120
tccccccatg ggggtgtagt cttggaggtc tagacttctg ntaagcgtca gtggttggtg   9180
tggtcctgaa ggttcgtatc ggctangcag gagcacggtc tcagggccgg tgtggaagcc   9240
agagcagcag ctccggagag cgcatttgtg ttgcatggtg cccnagtctg gtcgcttggg   9300
tggcttgaac ccatccggtt cagtgggtac acagccttgg ggctggtgtg tggagaacgc   9360
ctttatgtta tagggtatca attttgttca cttgggttac ggagtcgtcg actcgtctgg   9420
tacacggcct cagggccgat atgtgtctct ctgtgtgtgt ctgtttgtgt gttgttgagg   9480
tttgtacgcc agggcggcgg ctccaagtcg tgttgtatgg tatcgactct ggtcgttaga   9540
gcgactgagt cgccggctca tttggggcgc agcctcggaa ctggtgtgtg tgtcacaggc   9600
tcacaactgt attagttttg agctagtttt ccttgttaac cggtcaatta aaattcttct   9660
gtatgaaaag gcagagctac tgtcagttac tagggaaaaa atgtttctgg catgaaaaac   9720
tattttctat ccatttcatg tagtgacaac ttttcttttt cttgagtgag actactaact   9780
ttccatgaaa gtcagatgaa aatcaacaac ttctataaac aaacagaact ttccagaaat   9840
aaggaacaaa ttgttggata tatcagcaat ttttcaattt atttatttaa tacgaaagca   9900
tgatgatagt gctggcaaga tttaatccta attgtaatct aaacatgtga gtgcgtgcat   9960
aaaacatgca tatctcttaa catagtgagt actggaaact catgaaccaa gcagaagtgg  10020
gatgaatgga tcatacccctc cagtagcaaa agtaagggggt tagggccgtg gcaacagcag  10080
cattggcatt ggtggccttc ttcaaggaac cattgttccc acccatgggt ttggttgggg  10140
aagtcaagaa agtagtcgaa gtcgtggatg caaaaggaca gaagggagcc gtcagggtga  10200
catgctcccc aataacctta ttgatctcca cctggtgcat ggttctgttg cgtgccgcag  10260
agaaggtgcg cacatgtacc cactcctctt ctcatgctcc caatgggtca tgaagagagt  10320
tcttatatat tggtccaaat tctcctccac tccttgggtc ggactaaatt tccaaccatt  10380
tcatgaaacc actaatgggt ctttgagatt atgcaggaat tattaattat ataatatggc  10440
ccaaggccca tctaactttc aacaataata acttaattgt tcaactgagg tgttggtttt  10500
tcatttgaat tctcaggtta gtggaatgcc tacatttgcc cttcctgttc aagttggtgg  10560
ggttggtttt gactatcgct tacatatggc tgttgccgac aaatggattg aacttctcaa  10620
gtaagtgttt caaaattggt atgcatatgt taatatttta ctggacagaa gatttgattg  10680
tcagtgtata ttaatgcaat taaaatgttc ctttgcgtaa cactattgca catatggact  10740
tccacatgaa tgtccaaaaa catgtatcgt tattagtgta tttgatttgg ccacaatgtg  10800
attatagttg tgatttcgta gtttatacag tataacaaca aaagtaggat acatgtncca  10860
ncttttggga attcttataa tgatattaca cttttttaat cttgcatccc tcatcatttc  10920
tattgnctca gttgtttcaa gtttctataa aagtttggtt tcgtgttctg gttattgatg  10980
```

```
tggagtatct tgtatctgaa acatgaattg caacttttta ttctaaacag aggaaacgat   11040
gaagcttggg agatgggtaa tattgtgcac acactaacaa acagaaggtg gctggaaaag   11100
tgtgttactt atgctgaaag tcacgatcaa gcacttgttg gagacaagac tattgcattc   11160
tggttgatgg acaaggnaac aacacattat ttctccagac tttaaatact aacatttatt   11220
ttgnttcgca atttccttat atctatgatt tttaattata cttatctctc ttgattttcc   11280
tccccacaaa aatgcaagct agaatttttt tcctcatgaa agtatgcaaa gcttgngcct   11340
atgcattgat aaagtattta caagcctaag aataggcgac aaccgaccac tcaagcgaag   11400
tccacaatca aatggttgtc agacacgtta ccgaactact tttagcctaa atgacaacca   11460
cacaaacaca ctgggttgcc cttgctttgg ataaatcgat ggcccctaga ctgccggtcg   11520
cacctcggaa ctgccaaccg ccatggccgc ttgaatagtg aaccatcaca cattgccata   11580
tcctctacat gttgaaactt agtacgcaac cgtagtcgat cgtgccccca agatgccaca   11640
tcacgggatt ggcacatggc tgatgcaagt aggaaccact gaaaaagcca aggcttgtgt   11700
tcataccaat cgaaggaaaa ccttgaagaa caaagccatt agaaaggtat caacatcaac   11760
tggctacctc gtctgatcta ggtctgaatc gacaaacccg atttggcttt tcactctaag   11820
gattagacaa caggggatgg ggtaaattgg tattccttga caatgccccc aaggtggaaa   11880
cggtgttagg aaggcgtcac tagtccttt atacagactg ctaagtgcgg agacgggaat   11940
cgaacccgtg acctcaaggt tatgagcctc gtcggcattg acagtgggaa tatcaagtgc   12000
ccctaacact taggtgttcc catgtctaga aaaatcaatt ttaaatgttt caaaaaaaat   12060 cttttttgt gaatcttcat aaaacatgtg tttgcaaccc ctaaaagta caaatccaaa   12120 ctcagaatac atataggaca acacaaaaga caaatctaga tgtgaacatt gccattttg   12180 tttttgatt ctattcatga tgatttgtct ttttcgttcc tccaagtatt ttgattttaa   12240 tttttagag gtcgtagaca catcctatga actttcacaa ctcttttct agaatcgttt   12300 gaaacgttta aaaatgaatc tctagatatg gggaatgaca acgcccaagt gttgggagca   12360 ctattttt ttcccacacc tacctggtgg ggatgggttt cgtttgaagc cgcatgacca   12420
ccactcatgc catgggtgca gccccatgaa ggctcctcaa caaaatgtat caccacccgc   12480
aatcacacta gctcgacagc ctgattgcca tgccatccca ccaacaagga ctaccatgca   12540
ttgcacatca ggaccaacat agactgactg caaggagctg gaacatggtt taggagccta   12600
tgtacttgaa acctatacct gcagtgagat gcccggacct acgacaacac cactagagca   12660
cacatcagca accctgggca aagcatgaca aatgatgcca ggtacatcca tccgtagatg   12720
ttgcaagatg acgccggacg ggaactaana gcatcttcaa taacttgtgg natgttagtt   12780
tgttacaaaa tatagtaatc tcttcaccaa taagccattc tacaaatact ccaatggagt   12840
gtatttagct tgtcgaatag gaggtgagag aatatatagg attgctctta ggtatcgcta   12900
agtgatgtaa gcgcaagccc tatggttgtc ccaatcttca taatttgtag gtggcaaagg   12960
ggancatcac aaagaacaca tagncntaaa gaggaaacac ccaaacaata ttctcatcac   13020
acatgtcctc tttagtttaa tgctttgcta accctaattt gagtccatgg tacagtttat   13080
acagcatagg acgaagctg gtaggtagga gagggataca tggccncttg actcgatttc   13140
cacgcaggca tgggacgggc agtccaggtt gcaagcctga cagtctggtc gttgtagctc   13200
gtccggatca gggcttcccc atgcgccgct cgaagggctc actccaggtg tcgatagtct   13260
aggctccaag ttggacagcc ggcttcacca atttagcttt tgttgcctag cgtgtggtag   13320
```

-continued

```
ccggactaag gaccagacgg tgttctagag aaggtttttg tctggttgtt ggattccagt   13380
agcccatctc cttcgtcgtg cacttcctcc ttcgcttcca cgcttccttc gcagatggtg   13440
taggcgtact cttgtgcttg ccttggtaaa ttcgctctca tgttcaatat ggacgaactc   13500
attgccacac gccgccatgt ttgaagggta agtcccatgc tcaaccatct catcaccgtt   13560
gccaaggatg aaggccatat ggtgtggctc atcatcatca tccgcctcca tgactgaagg   13620
gaatatccca tgctcaacca tctcacttga ggtgcctccg aagatggagc ggtcacactt   13680
gcttgttgtt ggtgatcgac gtgatgtagt cgccggagcg tcagagcttg aaggagtatc   13740
acttatttgt aactcgagga agagaaatgt tgcttgatgt agcattgtgt ccattgttgg   13800
tgtagattct tcaaggaatg ttttcttgta ggctttatgc atcgttttct tgatgtcgtg   13860
gccattcctc ttcatgatgc gtttggagtg tgnaagcgct cttcttgttg atgatgttca   13920
cggtcaaggg tgtggccttg gaatccatcg ttgcgaagaa ggttgtagct tgatgttgct   13980
cttgtacttt gaggtgtcaa tgccggtgtg atcctgaaga cttgtggtgg ttgagcacgt   14040
tttgaaagag ttgtgcgtca atcttggcgt cccaatggtc catctnggcg tcaaagttt   14100 tggtgtagnc ctagaccgga ggtgatgtgc cttctctatt catattgaca ctcgancaaa   14160
gtgtgagtgg acnaagggaa agaacaatac caaagttacc tctttccgat gttggtgaag   14220
gatcaagcga tctcacacta tggaatatta agagagaaca ataccaaagt tacctctttc   14280
cgatacattc gtcaacacaa tacctttgtc gaggttggag gcaaccggcc ttgatttcgg   14340
ttgtggtgtc aaaggatgga gtggttgttg ttgttacgag aaccaaagcg gaagaacaac   14400
cacaaatcaa aaaggggcg aaagatgaca aatttcagca gattcggaag aggtcggaca   14460
gtcgagttgg tggccccttt ttcgactcga gcaaagtgtg agtggcaagg gaaagancaa   14520
taccaaagtt acctctttcc gatgttggtg aaggatcaag cgatctcaca ctatggaata   14580
ttaagagaga ncaataccaa agttacctct tcccgataca ttggtcaaca caataccttt   14640
gtcgaggtca gaggcaaccg gccttgcttt cggttgtggt gtcaaaggat ggagtggttg   14700
ttgttgttac gagaaccaaa gcggaagaac aaccacaaat cgaaaaggg gcgaaagatg   14760 aacaaatttc agcagattca agagaggtcg gacagtccga gttggtggcc ggacgggggt   14820
tggctggaca gtccgggttg gaagctgaca gttcgggtag gtcaactcgg ctgttcttca   14880
ggggaaattg gatcga                                                    14896
```

<210> SEQ ID NO 12
<211> LENGTH: 623
<212> TYPE: PRT
<213> ORGANISM: Aegilops tauschii

<400> SEQUENCE: 12

```
Met Ala Ala Pro Ala Phe Ala Val Ser Ala Ala Gly Leu Ala Arg Pro
1               5                   10                  15

Ser Ala Pro Arg Ser Gly Gly Ala Glu Arg Arg Gly Arg Gly Val Glu
            20                  25                  30

Leu Gln Ser Pro Ser Leu Leu Phe Gly Arg Asn Lys Gly Thr Arg Ser
        35                  40                  45

Pro Arg Ala Val Gly Val Gly Gly Ser Gly Trp Arg Val Val Met Arg
    50                  55                  60

Ala Gly Gly Pro Ser Gly Glu Val Met Ile Pro Asp Gly Gly Ser Gly
65                  70                  75                  80

Gly Thr Pro Pro Ser Ile Asp Gly Pro Val Gln Phe Asp Ser Asp Asp
                85                  90                  95
```

```
Leu Lys Val Pro Phe Ile Asp Asp Glu Thr Ser Leu Gln Asp Gly Gly
            100                 105                 110

Glu Asp Ser Ile Trp Ser Ser Glu Thr Asn Gln Val Ser Glu Glu Ile
            115                 120                 125

Asp Ala Glu Asp Thr Ser Arg Met Asp Lys Ser Ser Thr Arg Glu
            130                 135                 140

Lys Leu Arg Ile Leu Pro Pro Gly Asn Gly Gln Gln Ile Tyr Glu
145                 150                 155                 160

Ile Asp Pro Thr Leu Arg Asp Phe Lys Tyr His Leu Glu Tyr Arg Tyr
            165                 170                 175

Ser Leu Tyr Arg Arg Ile Arg Ser Asp Ile Asp Glu His Glu Gly Gly
            180                 185                 190

Met Asp Val Phe Ser Arg Gly Tyr Glu Lys Phe Gly Phe Met Arg Ser
            195                 200                 205

Ala Glu Gly Ile Thr Tyr Arg Glu Trp Ala Pro Gly Ala Asp Ser Ala
            210                 215                 220

Ala Leu Val Gly Asp Phe Asn Asn Trp Asp Pro Asn Ala Asp His Met
225                 230                 235                 240

Ser Lys Asn Asp Leu Gly Val Trp Glu Ile Phe Leu Pro Asn Asn Ala
            245                 250                 255

Asp Gly Ser Pro Pro Ile Pro His Gly Ser Arg Val Lys Val Arg Met
            260                 265                 270

Asp Thr Pro Ser Gly Ile Lys Asp Ser Ile Pro Ala Trp Ile Lys Tyr
            275                 280                 285

Ser Val Gln Thr Pro Gly Asp Ile Pro Tyr Asn Gly Ile Tyr Tyr Asp
            290                 295                 300

Pro Pro Glu Glu Glu Lys Tyr Val Phe Lys His Pro Gln Pro Lys Arg
305                 310                 315                 320

Pro Lys Ser Leu Arg Ile Tyr Glu Thr His Val Gly Met Ser Ser Pro
            325                 330                 335

Glu Pro Lys Ile Asp Thr Tyr Ala Asn Phe Arg Asp Glu Val Leu Pro
            340                 345                 350

Arg Ile Lys Arg Leu Gly Tyr Asn Ala Val Gln Ile Met Ala Ile Gln
            355                 360                 365

Glu His Ser Tyr Tyr Gly Ser Phe Gly Tyr His Val Thr Asn Phe Phe
            370                 375                 380

Ala Pro Ser Ser Arg Phe Gly Ser Pro Glu Asp Leu Lys Ser Leu Ile
385                 390                 395                 400

Asp Arg Ala His Glu Leu Gly Leu Val Val Leu Met Asp Val Val His
            405                 410                 415

Ser His Ala Ser Asn Asn Thr Leu Asp Gly Leu Asn Gly Phe Asp Gly
            420                 425                 430

Thr Asp Thr His Tyr Phe His Gly Gly Ser Arg Gly His His Trp Met
            435                 440                 445

Trp Asp Ser Arg Val Phe Asn Tyr Gly Asn Lys Glu Val Ile Arg Phe
            450                 455                 460

Leu Leu Ser Asn Ala Arg Trp Trp Leu Glu Glu Tyr Lys Phe Asp Gly
465                 470                 475                 480

Phe Arg Phe Asp Gly Ala Thr Ser Met Met Tyr Thr His His Gly Leu
            485                 490                 495

Gln Val Thr Phe Thr Gly Ser Tyr His Glu Tyr Phe Gly Phe Ala Thr
            500                 505                 510
```

```
Asp Val Asp Ala Val Val Tyr Leu Met Leu Met Asn Asp Leu Ile His
        515                 520                 525

Gly Phe Tyr Pro Glu Ala Val Thr Ile Gly Asp Val Ser Gly Met
530                 535                 540

Pro Thr Phe Ala Leu Pro Val Gln Val Gly Gly Val Gly Phe Asp Tyr
545                 550                 555                 560

Arg Leu His Met Ala Val Ala Asp Lys Trp Ile Glu Leu Leu Lys Gly
                565                 570                 575

Asn Asp Glu Ala Trp Glu Met Gly Asn Ile Val His Thr Leu Thr Asn
            580                 585                 590

Arg Arg Trp Leu Glu Lys Cys Val Thr Tyr Ala Glu Ser His Asp Gln
        595                 600                 605

Ala Leu Val Gly Asp Lys Thr Ile Ala Phe Trp Leu Met Asp Lys
    610                 615                 620

<210> SEQ ID NO 13
<211> LENGTH: 23
<212> TYPE: DNA
<213> ORGANISM: Artificial Sequence
<220> FEATURE:
<223> OTHER INFORMATION: Synthetic Construct

<400> SEQUENCE: 13
acggctttga tcatctcctc cca                                              23

<210> SEQ ID NO 14
<211> LENGTH: 25
<212> TYPE: DNA
<213> ORGANISM: Artificial Sequence
<220> FEATURE:
<223> OTHER INFORMATION: Synthetic Construct

<400> SEQUENCE: 14
tttgtctctt tgatgttccc caaat                                            25

<210> SEQ ID NO 15
<211> LENGTH: 31
<212> TYPE: DNA
<213> ORGANISM: Artificial Sequence
<220> FEATURE:
<223> OTHER INFORMATION: Synthetic Construct

<400> SEQUENCE: 15
tatgaccaga gtatgtctac agcttggcaa t                                     31

<210> SEQ ID NO 16
<211> LENGTH: 27
<212> TYPE: DNA
<213> ORGANISM: Artificial Sequence
<220> FEATURE:
<223> OTHER INFORMATION: Synthetic Construct

<400> SEQUENCE: 16
tgcatcctaa gtgggaaacc ctaacca                                          27

<210> SEQ ID NO 17
<211> LENGTH: 27
<212> TYPE: DNA
<213> ORGANISM: Artificial Sequence
<220> FEATURE:
<223> OTHER INFORMATION: Synthetic Construct

<400> SEQUENCE: 17
```
tcaatttgga tcagagggga tagtcca                                27

<210> SEQ ID NO 18
<211> LENGTH: 27
<212> TYPE: DNA
<213> ORGANISM: Artificial Sequence
<220> FEATURE:
<223> OTHER INFORMATION: Synthetic Construct

<400> SEQUENCE: 18
tgacaaggtt gcccatttct aatgcaa                                27

<210> SEQ ID NO 19
<211> LENGTH: 28
<212> TYPE: DNA
<213> ORGANISM: Artificial Sequence
<220> FEATURE:
<223> OTHER INFORMATION: Synthetic Construct

<400> SEQUENCE: 19
gatagctgga ttaggcgatc gcctcagg                               28

<210> SEQ ID NO 20
<211> LENGTH: 30
<212> TYPE: DNA
<213> ORGANISM: Artificial Sequence
<220> FEATURE:
<223> OTHER INFORMATION: Synthetic Construct

<400> SEQUENCE: 20
ttggtagagg aattagcaaa gtaaaatcca                             30

<210> SEQ ID NO 21
<211> LENGTH: 32
<212> TYPE: DNA
<213> ORGANISM: Artificial Sequence
<220> FEATURE:
<223> OTHER INFORMATION: Synthetic Construct

<400> SEQUENCE: 21
ggtagaacct tttgcattat gtgtgctttt cc                          32

<210> SEQ ID NO 22
<211> LENGTH: 33
<212> TYPE: DNA
<213> ORGANISM: Artificial Sequence
<220> FEATURE:
<223> OTHER INFORMATION: Synthetic Construct

<400> SEQUENCE: 22
gctacctcga aatgcaatgg aaatcttaga gac                         33

<210> SEQ ID NO 23
<211> LENGTH: 27
<212> TYPE: DNA
<213> ORGANISM: Artificial Sequence
<220> FEATURE:
<223> OTHER INFORMATION: Synthetic Construct

<400> SEQUENCE: 23
ccaaggaggg agtgaggagc ttgactt                                27

<210> SEQ ID NO 24
<211> LENGTH: 27
<212> TYPE: DNA
<213> ORGANISM: Artificial Sequence

```
<220> FEATURE:
<223> OTHER INFORMATION: Synthetic Construct

<400> SEQUENCE: 24
tgtcagcttg aatgcccttg cacttct                                              27

<210> SEQ ID NO 25
<211> LENGTH: 23
<212> TYPE: DNA
<213> ORGANISM: Artificial Sequence
<220> FEATURE:
<223> OTHER INFORMATION: Synthetic Construct

<400> SEQUENCE: 25
gatcgcgctt cctgaacctg tat                                                  23

<210> SEQ ID NO 26
<211> LENGTH: 25
<212> TYPE: DNA
<213> ORGANISM: Artificial Sequence
<220> FEATURE:
<223> OTHER INFORMATION: Synthetic Construct

<400> SEQUENCE: 26
ctcagaccac gaagggatct gtatg                                                25

<210> SEQ ID NO 27
<211> LENGTH: 27
<212> TYPE: DNA
<213> ORGANISM: Artificial Sequence
<220> FEATURE:
<223> OTHER INFORMATION: Synthetic Construct

<400> SEQUENCE: 27
atgaatacgt gcaacactcc catctgc                                              27

<210> SEQ ID NO 28
<211> LENGTH: 29
<212> TYPE: DNA
<213> ORGANISM: Artificial Sequence
<220> FEATURE:
<223> OTHER INFORMATION: Synthetic construct

<400> SEQUENCE: 28
ggaagcaaag ttttgcactt gccaatatg                                            29

<210> SEQ ID NO 29
<211> LENGTH: 28
<212> TYPE: DNA
<213> ORGANISM: Artificial Sequence
<220> FEATURE:
<223> OTHER INFORMATION: Synthetic Construct

<400> SEQUENCE: 29
cgtctccagc aagccatttc ctacctta                                             28

<210> SEQ ID NO 30
<211> LENGTH: 28
<212> TYPE: DNA
<213> ORGANISM: Artificial Sequence
<220> FEATURE:
<223> OTHER INFORMATION: Synthetic Construct

<400> SEQUENCE: 30
ttttgccact agttttttgcc aattttcc                                            28
```

<210> SEQ ID NO 31
<211> LENGTH: 29
<212> TYPE: DNA
<213> ORGANISM: Artificial Sequence
<220> FEATURE:
<223> OTHER INFORMATION: Synthetic Construct

<400> SEQUENCE: 31
tcaatcaatt tggatcagag ggaacatca                                    29

<210> SEQ ID NO 32
<211> LENGTH: 36
<212> TYPE: DNA
<213> ORGANISM: Artificial Sequence
<220> FEATURE:
<223> OTHER INFORMATION: Synthetic Construct

<400> SEQUENCE: 32
tagcagtgca ggaatttaag ttaaaccact attaca                            36

<210> SEQ ID NO 33
<211> LENGTH: 24
<212> TYPE: DNA
<213> ORGANISM: Artificial Sequence
<220> FEATURE:
<223> OTHER INFORMATION: Synthetic Construct

<400> SEQUENCE: 33
ctcccattct cgtttattcg tagc                                         24

<210> SEQ ID NO 34
<211> LENGTH: 26
<212> TYPE: DNA
<213> ORGANISM: Artificial Sequence
<220> FEATURE:
<223> OTHER INFORMATION: Synthetic Construct

<400> SEQUENCE: 34
gttcggttac catgtcacct cagagc                                       26

<210> SEQ ID NO 35
<211> LENGTH: 28
<212> TYPE: DNA
<213> ORGANISM: Artificial Sequence
<220> FEATURE:
<223> OTHER INFORMATION: Synthetic Construct

<400> SEQUENCE: 35
gccaattgaa caacaatgcc acttcatt                                     28

<210> SEQ ID NO 36
<211> LENGTH: 24
<212> TYPE: DNA
<213> ORGANISM: Artificial Sequence
<220> FEATURE:
<223> OTHER INFORMATION: Synthetic Construct

<400> SEQUENCE: 36
gagtacccat tcgcacctag atgt                                         24

<210> SEQ ID NO 37
<211> LENGTH: 27
<212> TYPE: DNA
<213> ORGANISM: Artificial Sequence
<220> FEATURE:
<223> OTHER INFORMATION: Synthetic Construct

<400> SEQUENCE: 37
gcctgttgca cgagcccatt aattact                                      27

<210> SEQ ID NO 38
<211> LENGTH: 28
<212> TYPE: DNA
<213> ORGANISM: Artificial Sequence
<220> FEATURE:
<223> OTHER INFORMATION: Synthetic Construct

<400> SEQUENCE: 38
ttcgaacaaa tggacaccag cttttgat                                     28

<210> SEQ ID NO 39
<211> LENGTH: 28
<212> TYPE: DNA
<213> ORGANISM: Artificial Sequence
<220> FEATURE:
<223> OTHER INFORMATION: Synthetic Construct

<400> SEQUENCE: 39
ttatatatca acttatgaat cctgaacg                                     28

<210> SEQ ID NO 40
<211> LENGTH: 31
<212> TYPE: DNA
<213> ORGANISM: Artificial Sequence
<220> FEATURE:
<223> OTHER INFORMATION: Synthetic Construct

<400> SEQUENCE: 40
gtaaagtgtt cttttagcaa tttatacaaa c                                 31

<210> SEQ ID NO 41
<211> LENGTH: 30
<212> TYPE: DNA
<213> ORGANISM: Artificial Sequence
<220> FEATURE:
<223> OTHER INFORMATION: Synthetic Construct

<400> SEQUENCE: 41
gcctcctcat ttcgctcgcg tgggtttaag                                   30

<210> SEQ ID NO 42
<211> LENGTH: 36
<212> TYPE: DNA
<213> ORGANISM: Artificial Sequence
<220> FEATURE:
<223> OTHER INFORMATION: Synthetic Construct

<400> SEQUENCE: 42
agtgactatg aacttcaaga atttcgtgat acatca                            36

<210> SEQ ID NO 43
<211> LENGTH: 32
<212> TYPE: DNA
<213> ORGANISM: Artificial Sequence
<220> FEATURE:
<223> OTHER INFORMATION: Synthetic Construct

<400> SEQUENCE: 43
ctacaaaaaa ttgaacaacg atgccacttc at                                32

<210> SEQ ID NO 44

```
<211> LENGTH: 27
<212> TYPE: DNA
<213> ORGANISM: Artificial Sequence
<220> FEATURE:
<223> OTHER INFORMATION: Synthetic Construct

<400> SEQUENCE: 44
ccaactatat ttacagctca actctgg                                            27

<210> SEQ ID NO 45
<211> LENGTH: 27
<212> TYPE: DNA
<213> ORGANISM: Artificial Sequence
<220> FEATURE:
<223> OTHER INFORMATION: Synthetic Construct

<400> SEQUENCE: 45
actgattttg ttcttgcaag acattca                                            27

<210> SEQ ID NO 46
<211> LENGTH: 24
<212> TYPE: DNA
<213> ORGANISM: Artificial Sequence
<220> FEATURE:
<223> OTHER INFORMATION: Synthetic Construct

<400> SEQUENCE: 46
caaatggaca ccagcttttg atgc                                               24

<210> SEQ ID NO 47
<211> LENGTH: 37
<212> TYPE: DNA
<213> ORGANISM: Artificial Sequence
<220> FEATURE:
<223> OTHER INFORMATION: Synthetic Construct

<400> SEQUENCE: 47
aaagttagct atatgcagtt taagttaatt tacaggt                                 37

<210> SEQ ID NO 48
<211> LENGTH: 30
<212> TYPE: DNA
<213> ORGANISM: Artificial Sequence
<220> FEATURE:
<223> OTHER INFORMATION: Synthetic Construct

<400> SEQUENCE: 48
tgtaagatgt tctttcagca atttatacta                                         30

<210> SEQ ID NO 49
<211> LENGTH: 22
<212> TYPE: DNA
<213> ORGANISM: Artificial Sequence
<220> FEATURE:
<223> OTHER INFORMATION: Synthetic Construct

<400> SEQUENCE: 49
acgacgcgtg ccgattccgt at                                                 22

<210> SEQ ID NO 50
<211> LENGTH: 35
<212> TYPE: DNA
<213> ORGANISM: Artificial Sequence
<220> FEATURE:
<223> OTHER INFORMATION: Synthetic Construct

<400> SEQUENCE: 50
```
gccattcaca tcttatcaaa gactgtaaat tgttt 35

<210> SEQ ID NO 51
<211> LENGTH: 34
<212> TYPE: DNA
<213> ORGANISM: Artificial Sequence
<220> FEATURE:
<223> OTHER INFORMATION: Synthetic Construct

<400> SEQUENCE: 51
atcctacaaa aaattgaaca acaatgccac tttc 34

<210> SEQ ID NO 52
<211> LENGTH: 25
<212> TYPE: DNA
<213> ORGANISM: Artificial Sequence
<220> FEATURE:
<223> OTHER INFORMATION: Synthetic Construct

<400> SEQUENCE: 52
acatggagct acagttcaga tgtgc 25

<210> SEQ ID NO 53
<211> LENGTH: 27
<212> TYPE: DNA
<213> ORGANISM: Artificial Sequence
<220> FEATURE:
<223> OTHER INFORMATION: Synthetic Construct

<400> SEQUENCE: 53
gcctgttgca cgagcccatt actagat 27

<210> SEQ ID NO 54
<211> LENGTH: 34
<212> TYPE: DNA
<213> ORGANISM: Artificial Sequence
<220> FEATURE:
<223> OTHER INFORMATION: Synthetic Construct

<400> SEQUENCE: 54
ggcaattact tgtttctttg tgcaattact tgtt 34

<210> SEQ ID NO 55
<211> LENGTH: 28
<212> TYPE: DNA
<213> ORGANISM: Artificial Sequence
<220> FEATURE:
<223> OTHER INFORMATION: Synthetic Construct

<400> SEQUENCE: 55
gttttgaatg ctcaagagaa gtactagt 28

<210> SEQ ID NO 56
<211> LENGTH: 30
<212> TYPE: DNA
<213> ORGANISM: Artificial Sequence
<220> FEATURE:
<223> OTHER INFORMATION: Synthetic Construct

<400> SEQUENCE: 56
tgtaagatgt tctttcagca atttatacta 30

<210> SEQ ID NO 57
<211> LENGTH: 28
<212> TYPE: DNA

```
<213> ORGANISM: Artificial Sequence
<220> FEATURE:
<223> OTHER INFORMATION: Synthetic Construct

<400> SEQUENCE: 57
ttatgtcttg gtccaaagcc ccttttttg                                          28

<210> SEQ ID NO 58
<211> LENGTH: 30
<212> TYPE: DNA
<213> ORGANISM: Artificial Sequence
<220> FEATURE:
<223> OTHER INFORMATION: Synthetic Construct

<400> SEQUENCE: 58
tccacgtcag gaacttagac atgcaactat                                         30
```

WHEAT WITH INCREASED RESISTANT STARCH LEVELS

CROSS-REFERENCE TO RELATED APPLICATIONS

This application is a continuation application of U.S. patent application Ser. No. 14/825,369, filed Aug. 13, 2015, which is a continuation of U.S. patent application Ser. No. 13/633,588, filed Oct. 2, 2012, now U.S. Pat. No. 9,150,839, issued Oct. 6, 2015, which claims the benefit of U.S. Provisional Application No. 61/542,953, entitled "WHEAT WITH INCREASED RESISTANT STARCH LEVELS," filed Oct. 4, 2011; all of which are incorporated herein by reference.

STATEMENT REGARDING FEDERALLY SPONSORED RESEARCH OR DEVELOPMENT

This invention was made with government support under grant number DK085811 awarded by the National Institutes of Health. The government has certain rights in the invention.

FIELD

This invention relates to human-induced non-transgenic mutations in one or more starch branching enzyme II (SBEII) genes. In one embodiment, the invention relates to human-induced non-transgenic mutations in one or more SBEII genes of wheat and wheat plants. In still another embodiment, human-induced non-transgenic mutations are in the SBEIIa and/or SBEIIb gene sequences, more particularly, combined mutations in SBEIIa and in both SBEIIa and SBEIIb.

This invention further relates to wheat plants having wheat seeds and wheat flour with increased levels of amylose and increased levels of resistant starch as a result of non-transgenic mutations in at least one of their SBEII genes. This invention also relates to a method that utilizes non-transgenic means to create wheat plants having mutations in at least one of their SBEII genes. In addition, this invention concerns wheat flour and wheat-based food products made from the seeds of these wheat plants having mutations in at least one of their SBEII genes.

BACKGROUND

An alarming number of adults and children in the United States are either overweight or obese. Healthier food choices, including foods that are high in resistant starch, can help people to better manage their blood sugar levels and their weight. Resistant starch is defined as starch that is not digested in the small intestine of healthy individuals but is fermented in the large intestine. Due to its slow digestion, resistant starch does not have the same caloric load as readily digestible starch, nor does it cause as rapid a rise in blood glucose levels after ingestion. Instead, resistant starch results in a more controlled glucose release over a longer period of time after digestion. This results in a decreased glycemic response, increased insulin sensitivity, and greater feelings of satiety. As a form of dietary fiber, resistant starch contributes to better colon health due to its fermentation by probiotic organisms in the lower gastrointestinal tract into short chain fatty acids, such as butyrate.

In the United States, the majority of dietary starch is consumed in the form of wheat based foods, such as bread, cereals, pastas, and tortillas, which contain very low levels of resistant starch. Cereal starches typically contain less slowly digested amylose (about 25% of total starch) and more highly branched, rapidly digested amylopectin (about 75% of total starch). The amount of amylose in starch positively correlates with the levels of dietary fiber and resistant starch. In corn and barley, loss-of-function mutations of SBEIIb, one of several enzymes in the starch synthesis pathway, have been identified. SBEIIb is the predominant isoform of SBEII expressed in the endosperm of these crops and its loss results in increased amylose and resistant starch levels. In contrast, both SBEIIa and SBEIIb are expressed in the wheat endosperm, but SBEIIa is the major isoform that is expressed in this crop. Though there has been great interest in finding mutations that increase amylose content (and therefore resistant starch content) in wheat, wheat lines with increased amylose levels are not commercially available. Preferred mutations would be single nucleotide polymorphisms (SNPs) that reduce or eliminate SBEII enzyme activity (and, in turn, increase amylose levels) without having significant negative pleiotropic effects.

Identification of SNPs in wheat SBEII genes has proceeded slowly because, among other possible reasons, there is limited genetic diversity in today's commercial wheat cultivars and bread wheat is a polyploid, with a complement of 7 chromosomes from each of three ancestors called the A, B and D genomes, resulting in a total of 21 chromosomes. Typically, the bread wheat genome has three functionally redundant copies of each gene (called homoeologs), and therefore, single gene alterations usually do not produce any readily visible phenotype such as those that have been found in diploid corn. Often in wheat, altered variants of all three homoeologs must be combined genetically in order to evaluate their effects. Pasta (durum) wheat is a tetraploid, consisting of A and B genomes, so only two altered copies of each homoeolog must be combined to obtain a phenotype.

To further compound these challenges, SBEIIa and SBEIIb are closely located on the same chromosome in wheat, making it difficult for alleles in these genes to be inherited independently unless through a rare recombination event. Thus, it would be useful to have knock-down or knock-out mutations, resulting from SNPs, of both SBEIIa and SBEIIb of each genome of wheat. The availability of multiple allelic mutations within each SBEII locus, particularly within each SBEII locus of the same genome, would allow for the breeding of new, non-genetically modified wheat lines with a spectrum of increased amylose and resistant starch levels in seeds. Seeds from these lines could be used to produce healthier wheat-based food products, including flour, bread, cereals, pastas, and tortillas.

SUMMARY

In one embodiment, the invention relates to non-transgenic mutations in one or more SBEII genes. In one embodiment, one or more mutations are in the SBEIIa gene. In another embodiment, one or more mutations are in the SBEIIb gene. In another embodiment, one or more mutations are in each of the SBEIIa and SBEIIb genes.

In one embodiment, the invention relates to multiple non-transgenic mutations in the SBEIIa gene including but not limited to 1, 2, 3, 4, 5, 6, 7, 8, 9, 10, and greater than 10 mutations.

In another embodiment, the invention relates to multiple non-transgenic mutations in the SBEIIb gene including but not limited to 1, 2, 3, 4, 5, 6, 7, 8, 9, 10, and greater than 10 mutations.

In another embodiment, the invention relates to multiple non-transgenic mutations in the SBEIIa gene including but not limited to 1, 2, 3, 4, 5, 6, 7, 8, 9, 10, and greater than 10 mutations and multiple mutations in the SBEIIb gene including but not limited to 1, 2, 3, 4, 5, 6, 7, 8, 9, 10, and greater than 10 mutations.

In another embodiment, this invention relates to a wheat plant, wheat seeds, wheat plant parts, and progeny thereof with increased amylose content and increased resistant starch levels compared to wild type wheat plant, wheat seeds, wheat plant parts, and progeny thereof.

In another embodiment, this invention relates to a wheat plant, wheat seeds, wheat plant parts, and progeny thereof having reduced activity of one or more SBEII enzymes compared to the wild type wheat plant, wherein the reduction in SBEII enzyme activity is caused by a human-induced non-transgenic mutation in one or more of the wheat plant's SBEII genes. In another embodiment, the SBEIIa enzyme has reduced activity. In yet another embodiment, the SBEIIb enzyme has reduced activity. In still another embodiment, the SBEIIa and SBEIIb enzymes have reduced activity.

In another embodiment, this invention includes a wheat plant containing one or more mutated SBEII genes, as well as seeds, pollen, plant parts and progeny of that plant.

In another embodiment, this invention includes food and food products incorporating wheat seeds and wheat flour having reduced SBEII enzyme activity caused by a human-induced non-transgenic mutation in one or more SBEII genes.

In another embodiment, this invention includes a wheat plant having reduced activity of one or more SBEII enzymes compared to the wild type wheat plants, created by the steps of obtaining plant material from a parent wheat plant, inducing at least one mutation in at least one copy of an SBEII gene of the plant material by treating the plant material with a mutagen to create mutagenized plant material (e.g., seeds or pollen), analyzing progeny wheat plants to detect at least one mutation in at least one copy of a SBEII gene, selecting progeny wheat plants that have at least one mutation in at least one copy of an SBEII gene, crossing progeny wheat plants that have at least one mutation in at least one copy of an SBEII gene with other progeny wheat plants that have at least one mutation in a different copy of an SBEII gene, and repeating the cycle of identifying progeny wheat plants having mutations and crossing the progeny wheat plants having mutations with other progeny wheat plants having mutations to produce progeny wheat plants with reduced SBEII enzyme activity. In another embodiment, the method comprises growing or using the mutagenized plant material to produce progeny wheat plants.

BRIEF DESCRIPTION OF THE SEQUENCE LISTING

SEQ ID NO: 1 shows a partial *Triticum aestivum* gene for starch branching enzyme IIa, A genome, exons 1-14.

SEQ ID NO: 2 shows the partial protein sequence encoded by SEQ ID NO: 1.

SEQ ID NO: 3 shows the *Triticum aestivum* SBEIIa gene for starch branching enzyme IIa, B genome, exons 1-22 (GenBank Accession FM865435).

SEQ ID NO: 4 shows the protein encoded by SEQ ID NO: 3 (GenBank Accession CAR95900).

SEQ ID NO: 5 shows the *Aegilops tauschii* gene for starch branching enzyme IIa, D genome, complete sequence exons 1-22 (GenBank Accession AF338431).

SEQ ID NO: 6 shows the protein encoded by SEQ ID NO: 5 (GenBank Accession AAK26821).

SEQ ID NO: 7 shows a partial *Triticum aestivum* gene for starch branching enzyme IIb, A genome, exons 1-11.

SEQ ID NO: 8 shows the partial protein encoded by SEQ ID NO: 7.

SEQ ID NO: 9 shows the partial *Triticum aestivum* gene for starch branching enzyme IIb, B genome, exons 1-11.

SEQ ID NO: 10 shows the partial protein encoded by SEQ ID NO: 9.

SEQ ID NO: 11 shows the partial *Aegilops tauschii* gene for starch branching enzyme IIb, D genome, exons 1-16 (GenBank Accession AY740398).

SEQ ID NO: 12 shows the partial protein encoded by SEQ ID NO: 11 (GenBank Accession AAW80632).

SEQ ID NOs: 13-58 show exemplary homoeolog specific primers that have proven useful in identifying useful mutations within the SBEIIa and SBEIIb gene sequences.

DETAILED DESCRIPTION

Definitions

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, viscosity, etc., is from 100 to 1,000, it is intended that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, relative amounts of components in a mixture, and various temperature and other parameter ranges recited in the methods.

As used herein, the term "allele" is any of one or more alternative forms of a gene, all of which relate to one trait or characteristic. In a diploid cell or organism, the two alleles of a given gene occupy corresponding loci on a pair of homologous chromosomes.

As used herein, amino acid or nucleotide sequence "identity" and "similarity" are determined from an optimal global alignment between the two sequences being compared. An optimal global alignment is achieved using, for example, the Needleman-Wunsch algorithm (Needleman and Wunsch, 1970, J. Mol. Biol. 48:443-453). Sequences may also be aligned using algorithms known in the art including but not limited to CLUSTAL V algorithm or the Blastn or BLAST 2 sequence programs.

"Identity" means that an amino acid or nucleotide at a particular position in a first polypeptide or polynucleotide is identical to a corresponding amino acid or nucleotide in a second polypeptide or polynucleotide that is in an optimal global alignment with the first polypeptide or polynucleotide. In contrast to identity, "similarity" encompasses amino acids that are conservative substitutions. A "conservative" substitution is any substitution that has a positive score in the Blosum62 substitution matrix (Hentikoff and Hentikoff, 1992, Proc. Natl. Acad. Sci. USA 89: 10915-10919).

By the statement "sequence A is n % similar to sequence B," it is meant that n % of the positions of an optimal global alignment between sequences A and B consists of identical residues or nucleotides and conservative substitutions. By the statement "sequence A is n % identical to sequence B," it is meant that n % of the positions of an optimal global alignment between sequences A and B consists of identical residues or nucleotides.

As used herein, the term "plant" includes reference to an immature or mature whole plant, including a plant from which seed or grain or anthers have been removed. A seed or embryo that will produce the plant is also considered to be the plant.

As used herein, the term "plant parts" includes plant protoplasts, plant cell tissue cultures from which wheat plants can be regenerated, plant calli, plant clumps, and plant cells that are intact in plants or parts of plants, such as embryos, pollen, ovules, pericarp, seed, flowers, florets, heads, spikes, leaves, roots, root tips, anthers, and the like.

As used herein, the term "polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers, and to longer chains generally referred to as proteins. Polypeptides may contain amino acids other than the 20 gene-encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature and they are well known to those of skill in the art. It will be appreciated that the same type of modification may be present in the same or varying degree at several sites in a given polypeptide.

As used herein, an "SBEII derivative" refers to a SBEII protein/peptide/polypeptide sequence that possesses biological activity that is substantially reduced as compared to the biological activity of the whole SBEII protein/peptide/polypeptide sequence. In other words, it refers to a polypeptide of a modified SBEII protein of the invention that has reduced SBEII enzymatic activity. The term "SBEII derivative" encompasses the "fragments" or "chemical derivatives" of a modified SBEII protein/peptide.

As used herein, the term "polynucleotide(s)" generally refers to any polyribonucleotide or poly-deoxyribonucleotide, which may be unmodified RNA or DNA or modified RNA or DNA. This definition includes, without limitation, single- and double-stranded DNA, DNA that is a mixture of single- and double-stranded regions or single-, double- and triple-stranded regions, cDNA, single- and double-stranded RNA, and RNA that is a mixture of single- and double-stranded regions, hybrid molecules comprising DNA and RNA that may be single-stranded or, more typically, double-stranded, or triple-stranded regions, or a mixture of single- and double-stranded regions. The term "polynucleotide(s)" also embraces short nucleotides or fragments, often referred to as "oligonucleotides," that due to mutagenesis are not 100% identical but nevertheless code for the same amino acid sequence.

A "reduced or non-functional fragment," as is used herein, refers to a nucleic acid sequence that encodes for a SBEII protein that has reduced biological activity as compared the protein coding of the whole nucleic acid sequence. In other words, it refers to a nucleic acid or fragment(s) thereof that substantially retains the capacity of encoding an SBEII polypeptide of the invention, but the encoded SBEII polypeptide has reduced activity.

The term "fragment," as used herein, refers to a polynucleotide sequence, (e.g., a PCR fragment) which is an isolated portion of the subject nucleic acid constructed artificially (e.g., by chemical synthesis) or by cleaving a natural product into multiple pieces, using restriction endonucleases or mechanical shearing, or a portion of a nucleic acid synthesized by PCR, DNA polymerase or any other polymerizing technique well known in the art, or expressed in a host cell by recombinant nucleic acid technology well known to one of skill in the art.

With reference to polynucleotides of the invention, the term "isolated polynucleotide" is sometimes used. This term, when applied to DNA, refers to a DNA molecule that is separated from sequences with which it is immediately contiguous (in the 5' and 3'directions) in the naturally occurring genome of the organism from which it was derived. For example, the "isolated polynucleotide" may comprise a PCR fragment. In another embodiment, the "isolated polynucleotide" may comprise a DNA molecule inserted into a vector, such as a plasmid or virus vector, or integrated into the genomic DNA of a prokaryote or eukaryote. An "isolated polynucleotide molecule" may also comprise a cDNA molecule.

In one embodiment, the invention relates to non-transgenic mutations in one or more SBEII genes. In another embodiment, the invention describes wheat plants exhibiting seeds with increased amylose content and increased resistant starch levels compared to wild type wheat seeds, without the inclusion of foreign nucleic acids in the wheat plants' genomes.

In still another embodiment, the invention relates to a series of independent human-induced non-transgenic mutations in one or more SBEII genes; wheat plants having one or more of these mutations in at least one SBEII gene thereof; and a method of creating and identifying similar and/or additional mutations in at least one SBEII gene of wheat. Additionally, the invention relates to wheat plants exhibiting seed with increased amylose and resistant starch content compared to wild type wheat seed, without the inclusion of foreign nucleic acids in the plants' genomes.

SBEII Mutations

A. SBEII Genes

In one embodiment, the invention relates to one or more non-transgenic mutations in the SBEII gene. In another embodiment, the SBEII gene may contain one or more non-transgenic mutations recited in Tables 1-6 and 8-12 and corresponding mutations in homoeologues and combinations thereof.

In another embodiment, the invention comprises corresponding mutations to the one or more non-transgenic mutations disclosed herein in the SBEII gene in a corresponding homoeologue. By way of example, an identified mutation in the SBEIIa gene of the A genome may be a beneficial mutation in the SBEIIa gene of the B and/or D genome. One of ordinary skill in the art will understand that the mutation in the homoeologue may not be in the exact location.

One of ordinary skill in the art understands there is natural variation in the genetic sequences of the SBEII genes in different wheat varieties. The degree of sequence identity between homologous SBEIIa genes or the proteins is believed to be about 90%. This is true for SBEIIb genes and proteins as well.

The inventors have determined that to achieve a high amylose phenotype in wheat plants, mutations that reduce SBEII gene function are desirable. Preferred mutations include missense and nonsense changes, including mutations that prematurely truncate the translation of one or more SBEII proteins from messenger RNA, such as those mutations that create a stop codon within the coding region of an SBEII messenger RNA. Such mutations include insertions, repeat sequences, splice junction mutations, modified open reading frames (ORFs) and point mutations.

1. SBEIIa Genes

In another embodiment, the invention relates to one or more mutations in the SBEIIa gene. In one embodiment, the invention relates to multiple non-transgenic mutations in the SBEIIa gene including but not limited to 1, 2, 3, 4, 5, 6, 7, 8, 9, 10, and greater than 10 mutations.

In still another embodiment, one or more mutations are in the SBEIIa gene of the A genome. In another embodiment, one or more mutations are in the SBEIIa gene of the B genome. In still another embodiment, one or more mutations are in the SBEIIa gene of the D genome. In yet another embodiment, one or more mutations are in the SBEIIa genes of the A and B genomes. In still another embodiment, one or more mutations are in the SBEIIa genes of the A and D genomes. In another embodiment, one or more mutations are in the SBEIIa genes of the B and D genomes. In yet another embodiment, one or more mutations are in the SBEIIa genes of the A, B, and D genomes.

In one embodiment, one or more non-transgenic mutations are in both alleles of the SBEIIa gene in the A genome. In another embodiment, the non-transgenic mutations are identical in both alleles of the SBEIIa gene of the A genome.

In one embodiment, one or more non-transgenic mutations are in both alleles of the SBEIIa gene in the B genome. In another embodiment, the non-transgenic mutations are identical in both alleles of the SBEIIa gene of the B genome.

In one embodiment, one or more non-transgenic mutations are in both alleles of the SBEIIa gene in the D genome. In another embodiment, the non-transgenic mutations are identical in both alleles of the SBEIIa gene of the D genome.

The following mutations are exemplary of the mutations created and identified according to various embodiments of the invention. SEQ ID NOs 1-6 are reference sequences for SBEIIa. SEQ ID NOs 7-12 are reference sequences for SBEIIb.

The following mutations identified in Tables 1-6 are exemplary of the mutations created and identified according to various embodiments of the invention. They are offered by way of illustration, not limitation. It is to be understood that the mutations below are merely exemplary and that similar mutations are also contemplated.

The nomenclature used in Tables 1-6 and 8-12 indicates the wild type nucleotide or amino acid, followed by its position according to the referenced sequence, followed by the changed nucleotide or amino acid (A.A.) at that position using standard genetic code terminology. An asterisk is used to designate a stop codon, also called a truncation mutation.

One exemplary mutation is G5267A, resulting in a change from guanine to adenine at nucleotide position 5267 identified according to its position in the sequence of SEQ ID NO: 1. This mutation results in a change from tryptophan to a stop mutation at amino acid position 436 identified according to its position in the expressed protein (SEQ ID NO: 2).

TABLE 1

Examples of mutations created and identified in SBEIIa in the A genome of wheat plants. Nucleotide and amino acid changes are identified according to their positions in SEQ ID NOs: 1 and 2, respectively.

| Variety | Primer SEQ IDs. | Nucleotide Mutation | A.A. Mutation | PSSM | SIFT |
|---|---|---|---|---|---|
| Express | 13, 14 | C538T | V51= | | |
| Express | 13, 14 | G586A | E67= | | |
| Express | 13, 14 | C605T | P74S | | 0.89 |
| Express | 13, 14 | G608A | A75T | | 0.67 |
| Express | 13, 14 | C644T | Intron | | |
| Express | 13, 14 | G648A | Intron | | |
| Express | 13, 14 | C853T | Intron | | |
| Express | 13, 14 | G951A | G97= | | |
| Express | 13, 14 | G952A | G98R | | 0.44 |
| Express | 13, 14 | G1036A | E126K | | 0.86 |
| Express | 13, 14 | G1059A | P133= | | |
| Express | 15, 16 | C2384T | Intron | | |
| Express | 15, 16 | C2384T | Intron | | |
| Express | 15, 16 | C2394T | Intron | | |
| Express | 15, 16 | G2574A | Intron | | |
| Express | 15, 16 | G2582A | Splice Junction | | |
| Express | 15, 16 | G2592A | D260N | 10.4 | 0.3 |
| Express | 15, 16 | G2605A | G264D | 22 | 0 |
| Express | 15, 16 | G2612A | K266= | | |
| Express | 15, 16 | G2625A | A271T | 10.8 | 0.04 |
| Express | 15, 16 | C2664T | P284S | 20.3 | 0.01 |
| Express | 15, 16 | G2674A | G287D | 19.4 | 0 |
| Express | 15, 16 | C2857T | Intron | | |
| Express | 15, 16 | C2861T | Intron | | |
| Express | 15, 16 | C2921T | Intron | | |
| Express | 15, 16 | G2990A | E296K | | 0.03 |
| Express | 15, 16 | C3004T | F300= | | |
| Express | 15, 16 | G3039A | R312K | 8.2 | 0.08 |
| Express | 15, 16 | A3155T | Intron | | |
| Express | 17, 18 | C5164T | Intron | | |
| Express | 17, 18 | C5164T | Intron | | |
| Express | 17, 18 | G5196A | G413S | 13.8 | 0 |
| Kronos | 17, 18 | G5239A | G427D | 6.6 | 0.09 |
| Kronos | 17, 18 | C5256T | H433Y | 22.3 | 0 |
| Express | 17, 18 | G5267A | W436* | | |
| Kronos | 17, 18 | G5267A | W436* | | |
| Express | 17, 18 | G5268A | D437N | 7.9 | 0.04 |
| Express | 17, 18 | G5268A | D437N | 7.9 | 0.04 |
| Kronos | 17, 18 | G5268A | D437N | 7.9 | 0.04 |
| Express | 17, 18 | G5289A | G444R | 19 | 0 |
| Kronos | 17, 18 | G5289A | G444R | 19 | 0 |
| Express | 17, 18 | G5298A | E447K | 8.9 | 0.02 |
| Express | 17, 18 | G5301A | Splice Junction | | |
| Express | 17, 18 | G5301A | Splice Junction | | |
| Express | 17, 18 | G5305A | Intron | | |
| Kronos | 17, 18 | G5308A | Intron | | |
| Express | 17, 18 | C5315T | Intron | | |
| Express | 17, 18 | C5315T | Intron | | |
| Express | 17, 18 | C5315T | Intron | | |
| Express | 17, 18 | C5324T | Intron | | |
| Kronos | 17, 18 | C5325T | Intron | | |
| Kronos | 17, 18 | G5332A | Intron | | |
| Express | 17, 18 | G5386A | Intron | | |
| Express | 17, 18 | C5405T | L453= | | |
| Express | 17, 18 | C5405T | L453= | | |
| Express | 17, 18 | G5418A | R457K | 18.3 | 0.01 |
| Express | 17, 18 | G5422A | W458* | | |
| Kronos | 17, 18 | G5429A | E461K | 17.1 | 0.01 |
| Kronos | 17, 18 | G5429A | E461K | 17.1 | 0.01 |
| Express | 17, 18 | G5432A | E462K | 17.6 | 0.01 |

TABLE 1-continued

Examples of mutations created and identified in SBEIIa in the A genome of wheat plants. Nucleotide and amino acid changes are identified according to their positions in SEQ ID NOs: 1 and 2, respectively.

| Variety | Primer SEQ IDs. | Nucleotide Mutation | A.A. Mutation | PSSM | SIFT |
|---|---|---|---|---|---|
| Express | 17, 18 | G5432A | E462K | 17.6 | 0.01 |
| Express | 17, 18 | G5448A | G467E | 27.1 | 0 |
| Express | 17, 18 | G5463A | G472E | 27.1 | 0 |
| Express | 17, 18 | G5463A | G472E | 27.1 | 0 |
| Express | 17, 18 | G5463A | G472E | 27.1 | 0 |
| Express | 17, 18 | G5464A | G472= | | |
| Express | 17, 18 | G5465A | V473M | 17.1 | 0 |
| Express | 17, 18 | C5470T | T474= | | |
| Kronos | 17, 18 | C5470T | T474= | | |
| Express | 17, 18 | C5484T | T479I | 10.3 | 0.4 |
| Kronos | 17, 18 | G5493A | G482E | 27.1 | 0 |
| Kronos | 17, 18 | G5522A | Intron | | |
| Express | 17, 18 | G5534A | Intron | | |
| Express | 17, 18 | G5655A | Intron | | |
| Express | 17, 18 | C5712T | T488I | 16.9 | 0 |
| Express | 17, 18 | C5712T | T488I | 16.9 | 0 |
| Express | 17, 18 | C5719T | N490= | | |
| Express | 17, 18 | G5736A | G496E | 22.1 | 0 |
| Express | 17, 18 | C5745T | T499I | 15.8 | 0.02 |
| Express | 17, 18 | G5753A | D502N | 17.1 | 0.01 |
| Express | 17, 18 | G5756A | A503T | 19.8 | 0 |
| Express | 17, 18 | C5757T | A503V | 19.2 | 0 |
| Express | 17, 18 | G5783A | D512N | 7.8 | 0.18 |
| Kronos | 17, 18 | C5801T | H518Y | −8.3 | 1 |
| Express | 17, 18 | C5804T | P519S | 26.7 | 0 |
| Express | 17, 18 | C5811T | A521V | 6.3 | 0.21 |
| Express | 17, 18 | C5811T | A521V | 6.3 | 0.21 |
| Express | 17, 18 | G5831A | Splice Junction | | |
| Express | 17, 18 | G5852A | Intron | | |
| Express | 17, 18 | C5921T | Intron | | |
| Express | 17, 18 | G5956A | Intron | | |
| Express | 17, 18 | G5956A | Intron | | |

In one embodiment, the invention relates to a polynucleotide of the SBEIIa gene in the A genome with one or more non-transgenic mutations listed in Table 1 and corresponding to SEQ ID NO: 1. In another embodiment, the polynucleotide with one or more non-transgenic mutations listed in Table 1 is 85%, 86%, 87%, 88%, 89%, 90%, 91%, 92%, 93%, 94%, 95%, 96%, 97%, 98%, 99% or greater than 99% identical to SEQ ID NO: 1. In yet another embodiment, the polynucleotide with one or more non-transgenic mutations listed in Table 1 is 85%, 86%, 87%, 88%, 89%, 90%, 91%, 92%, 93%, 94%, 95%, 96%, 97%, 98%, 99% or greater than 99% similar to SEQ ID NO: 1.

In still another embodiment, the polynucleotide with one or more non-transgenic mutation listed in Table 1 codes for a SBEIIa protein, wherein the SBEIIa protein comprises one or more non-transgenic mutations and is 85%, 86%, 87%, 88%, 89%, 90%, 91%, 92%, 93%, 94%, 95%, 96%, 97%, 98%, 99% or greater than 99% identical to SEQ ID NO: 2. In still another embodiment, the polynucleotide with one or more non-transgenic mutation listed in Table 1 codes for a SBEIIa protein, wherein the SBEIIa protein comprises one or more non-transgenic mutations and is 85%, 86%, 87%, 88%, 89%, 90%, 91%, 92%, 93%, 94%, 95%, 96%, 97%, 98%, 99% or greater than 99% similar to SEQ ID NO: 2.

Examples of mutations created and identified in SBEIIa in the B genome of wheat plants are provided in Table 2. Nucleotide and amino acid changes are identified according to their positions in SEQ ID NOs: 3 and 4, respectively.

TABLE 2

Representative mutations in the SBEIIa gene in the B genome

| Variety | Primer SEQ IDs. | Nucleotide Mutation | A.A. Mutation | PSSM | SIFT |
|---|---|---|---|---|---|
| Express | 23, 24 | C4792T | Intron | | |
| Express | 23, 24 | G4830A | Intron | | |
| Express | 23, 24 | C4878T | Intron | | |
| Kronos | 23, 24 | C4881T | Intron | | |
| Express | 23, 24 | C4937T | Intron | | |
| Express | 23, 24 | C4960T | T410I | 4.8 | 0.25 |
| Express | 23, 24 | C4960A | T410N | 13.9 | 0.02 |
| Express | 23, 24 | C4961T | T410= | | |
| Express | 23, 24 | G4978A | G416D | 14.5 | 0.73 |
| Express | 23, 24 | G4987A | G419D | 16.8 | 0.01 |
| Express | 23, 24 | G4987A | G419D | 16.8 | 0.01 |
| Express | 23, 24 | C4990T | T420I | 21.4 | 0 |
| Express | 23, 24 | C4998T | H423Y | 15.5 | 0.59 |
| Express | 23, 24 | C5006T | F425= | | |
| Kronos | 23, 24 | G5011A | G427D | −0.4 | 0.5 |
| Express | 23, 24 | C5017T | P429L | 14.1 | 0.11 |
| Express | 23, 24 | G5020A | R430H | 21.4 | 0 |
| Kronos | 23, 24 | G5020A | R430H | 21.4 | 0 |
| Kronos | 23, 24 | G5020A | R430H | 21.4 | 0 |
| Kronos | 23, 24 | G5020A | R430H | 21.4 | 0 |
| Kronos | 23, 24 | G5022A | G431S | 25.2 | 0 |
| Kronos | 23, 24 | C5025T | H432Y | −3.6 | 1 |
| Express | 23, 24 | G5032A | W434* | | |
| Kronos | 23, 24 | G5033A | W434* | | |
| Express | 23, 24 | G5036A | M435I | 15 | 0.03 |
| Express | 23, 24 | G5038A | W436* | | |
| Express | 23, 24 | G5038A | W436* | | |
| Kronos | 23, 24 | G5040A | D437N | 19.9 | 0.01 |
| Kronos | 23, 24 | G5040A | D437N | 19.9 | 0.01 |
| Express | 23, 24 | C5044T | S438F | 12.1 | 0.01 |
| Express | 23, 24 | G5062A | G444E | 17 | 0 |
| Kronos | 23, 24 | G5062A | G444E | 17 | 0 |
| Kronos | 23, 24 | G5062A | G444E | 17 | 0 |
| Kronos | 23, 24 | G5063A | G444= | | |
| Kronos | 23, 24 | G5065A | S445N | −4.7 | 1 |
| Express | 23, 24 | G5068A | W446* | | |
| Express | 23, 24 | G5069A | W446* | | |
| Express | 23, 24 | G5069A | W446* | | |
| Kronos | 23, 24 | G5069A | W446* | | |
| Express | 23, 24 | G5069A | W446* | | |
| Express | 23, 24 | G5069A | W446* | | |
| Express | 23, 24 | G5069A | W446* | | |
| Express | 23, 24 | G5070A | E447K | 9.3 | 0.02 |
| Express | 23, 24 | G5070A | E447K | 9.3 | 0.02 |
| Kronos | 23, 24 | G5073A | Splice Junction | | |
| Kronos | 23, 24 | G5080A | Intron | | |
| Express | 23, 24 | C5081T | Intron | | |
| Express | 23, 24 | G5083A | Intron | | |
| Kronos | 23, 24 | C5087T | Intron | | |
| Express | 23, 24 | C5090T | Intron | | |
| Kronos | 23, 24 | C5090T | Intron | | |
| Kronos | 23, 24 | C5090T | Intron | | |
| Express | 23, 24 | C5090T | Intron | | |
| Express | 23, 24 | G5092A | Intron | | |
| Kronos | 23, 24 | G5105A | Intron | | |
| Express | 23, 24 | G5112A | Intron | | |
| Kronos | 23, 24 | G5112A | Intron | | |
| Kronos | 23, 24 | C5129T | Intron | | |
| Kronos | 23, 24 | C5129T | Intron | | |
| Express | 23, 24 | C5158T | Intron | | |
| Express | 23, 24 | G5160A | Splice Junction | | |
| Express | 23, 24 | G5161A | V448I | | 0.01 |
| Express | 23, 24 | G5161A | V448I | | 0.01 |
| Express | 23, 24 | G5161A | V448I | | 0.01 |
| Express | 23, 24 | G5168A | R450K | 19 | 0.01 |
| Express | 23, 24 | G5168A | R450K | 19 | 0.01 |
| Kronos | 23, 24 | G5168A | R450K | 19 | 0.01 |
| Express | 23, 24 | C5172T | F451= | | |
| Express | 23, 24 | G5185A | A456T | 13.3 | 0.11 |
| Express | 23, 24 | G5185A | A456T | 13.3 | 0.11 |
| Kronos | 23, 24 | G5189A | R457K | 19 | 0.01 |
| Express | 23, 24 | G5193A | W458* | | |
| Express | 23, 24 | C5197T | L460F | 11.7 | 0.02 |

TABLE 2-continued

Representative mutations in the SBEIIa gene in the B genome

| Variety | Primer SEQ IDs. | Nucleotide Mutation | A.A. Mutation | PSSM | SIFT |
|---|---|---|---|---|---|
| Express | 23, 24 | G5200A | E461K | 18.3 | 0.01 |
| Kronos | 23, 24 | G5203A | E462K | 18.3 | 0 |
| Kronos | 23, 24 | G5203A | E462K | 18.3 | 0 |
| Kronos | 23, 24 | G5211A | K464= | | |
| Kronos | 23, 24 | G5211A | K464= | | |
| Express | 23, 24 | G5219A | G467E | 27.7 | 0 |
| Kronos | 23, 24 | G5219A | G467E | 27.7 | 0 |
| Kronos | 23, 24 | G5219A | G467E | 27.7 | 0 |
| Kronos | 23, 24 | G5219A | G467E | 27.7 | 0 |
| Kronos | 23, 24 | T5223C | F468= | | |
| Express | 23, 24 | C5224T | R469* | | |
| Kronos | 23, 24 | G5233A | G472R | 27.3 | 0 |
| Kronos | 23, 24 | G5234A | G472E | 27.7 | 0 |
| Kronos | 23, 24 | G5234A | G472E | 27.7 | 0 |
| Express | 23, 24 | G5234A | G472E | 27.7 | 0 |
| Kronos | 23, 24 | C5240T | T474I | 21.9 | 0 |
| Kronos | 23, 24 | C5244T | S475= | | |
| Express | 23, 24 | C5255T | T479I | 9.8 | 0.55 |
| Express | 23, 24 | G5264A | G482E | 27.7 | 0 |
| Express | 23, 24 | G5272A | Splice Junction | | |
| Express | 23, 24 | G5272A | Splice Junction | | |
| Kronos | 23, 24 | G5272A | Splice Junction | | |
| Kronos | 23, 24 | G5276A | Intron | | |
| Express | 23, 24 | G5284A | Intron | | |
| Express | 23, 24 | G5286A | Intron | | |
| Express | 23, 24 | G5287A | Intron | | |
| Kronos | 23, 24 | G5287A | Intron | | |
| Kronos | 23, 24 | C5297T | Intron | | |
| Kronos | 23, 24 | C5297T | Intron | | |
| Kronos | 23, 24 | G5306A | Intron | | |
| Express | 23, 24 | C5330T | Intron | | |
| Express | 23, 24 | G5338A | Intron | | |
| Express | 23, 24 | G5350A | Intron | | |
| Express | 23, 24 | G5350A | Intron | | |
| Express | 23, 24 | C5353T | Intron | | |
| Express | 23, 24 | G5364A | Intron | | |
| Express | 23, 24 | G5364A | Intron | | |
| Express | 23, 24 | G5372A | Intron | | |
| Express | 23, 24 | G5372A | Intron | | |
| Express | 23, 24 | C5379T | Intron | | |
| Express | 23, 24 | C5395T | Intron | | |
| Express | 23, 24 | G5409A | Intron | | |
| Express | 23, 24 | G5421A | Intron | | |
| Express | 23, 24 | C5448T | Intron | | |
| Express | 23, 24 | T5450C | Intron | | |
| Kronos | 23, 24 | C5469T | Intron | | |
| Express | 23, 24 | G5472A | Splice Junction | | |
| Express | 23, 24 | G5475A | M485I | | 0.18 |
| Express | 23, 24 | G5495A | G492D | −0.8 | 0.39 |
| Express | 23, 24 | T5522A | V501D | 8.3 | 0.08 |
| Express | 23, 24 | C5528A | A503E | 19.9 | 0 |
| Express | 23, 24 | G5530A | V504M | 7.8 | 0.04 |
| Express | 23, 24 | C5553T | N511= | | |
| Express | 23, 24 | G5566A | G516R | 5.2 | 0.32 |
| Express | 23, 24 | C5575T | P519S | 17.4 | 0.02 |
| Kronos | 23, 24 | C5582T | A521V | 4.8 | 0.33 |
| Kronos | 23, 24 | C5582T | A521V | 4.8 | 0.33 |
| Express | 23, 24 | C5589T | S523= | | |
| Express | 23, 24 | G5606A | Intron | | |
| Express | 23, 24 | G5646A | Intron | | |
| Express | 23, 24 | C5662T | Intron | | |
| Express | 23, 24 | C5662T | Intron | | |
| Express | 23, 24 | G5675A | Intron | | |
| Express | 23, 24 | G5675A | Intron | | |
| Express | 23, 24 | G5835A | Intron | | |
| Express | 23, 24 | C4960T | T410I | 4.8 | 0.25 |
| Express | 23, 24 | G4987A | G419D | 16.8 | 0.01 |
| Express | 23, 24 | G5185A | A456T | 13.3 | 0.11 |
| Express | 23, 24 | C5243T | S475F | 26.4 | 0 |
| Express | 23, 24 | C5255T | T479I | 9.8 | 0.55 |
| Express | 21, 22 | G2386A | G233D | | 0 |
| Express | 21, 22 | G2456A | K256= | | |
| Express | 21, 22 | G2464A | Intron | | |
| Express | 21, 22 | G2483A | Intron | | |
| Express | 21, 22 | C2509T | Intron | | |
| Express | 21, 22 | C2518T | Intron | | |
| Express | 21, 22 | G2606A | A279T | 3.1 | 0.14 |
| Express | 21, 22 | C2610T | P280L | 5.1 | 0.47 |
| Express | 21, 22 | G2613A | G281D | 2.7 | 0.36 |
| Express | 21, 22 | G2613A | G281D | 2.7 | 0.36 |
| Express | 21, 22 | C2648T | P293S | | 0.08 |
| Express | 21, 22 | G2661A | Intron | | |
| Express | 21, 22 | G2661A | Intron | | |
| Express | 21, 22 | G2689A | Intron | | |
| Express | 21, 22 | G2945A | Splice Junction | | |
| Express | 21, 22 | C2967T | P303S | 8.4 | 0.17 |
| Express | 21, 22 | C2967T | P303S | 8.4 | 0.17 |
| Express | 21, 22 | G2456A | K256= | | |
| Express | 21, 22 | C2518T | Intron | | |
| Express | 21, 22 | G2606A | A279T | 3.1 | 0.14 |
| Express | 21, 22 | G2606A | A279T | 3.1 | 0.14 |
| Express | 21, 22 | C2648T | P293S | | 0.08 |
| Express | 21, 22 | G2661A | Intron | | |
| Express | 21, 22 | C2967T | P303S | 8.4 | 0.17 |

In one embodiment, the invention relates to a polynucleotide of the SBEIIa gene in the B genome with one or more non-transgenic mutations listed in Table 2 and corresponding to SEQ ID NO: 3. In another embodiment, the polynucleotide with one or more non-transgenic mutations listed in Table 2 is 85%, 86%, 87%, 88%, 89%, 90%, 91%, 92%, 93%, 94%, 95%, 96%, 97%, 98%, 99% or greater than 99% identical to SEQ ID NO: 3. In yet another embodiment, the polynucleotide with one or more non-transgenic mutations listed in Table 2 is 85%, 86%, 87%, 88%, 89%, 90%, 91%, 92%, 93%, 94%, 95%, 96%, 97%, 98%, 99% or greater than 99% similar to SEQ ID NO: 3.

In still another embodiment, the polynucleotide with one or more non-transgenic mutation listed in Table 2 codes for a SBEIIa protein, wherein the SBEIIa protein comprises one or more non-transgenic mutations and is 85%, 86%, 87%, 88%, 89%, 90%, 91%, 92%, 93%, 94%, 95%, 96%, 97%, 98%, 99% or greater than 99% identical to SEQ ID NO: 4. In still another embodiment, the polynucleotide with one or more non-transgenic mutations listed in Table 2 codes for a SBEIIa protein, wherein the SBEIIa protein comprises one or more non-transgenic mutations and is 85%, 86%, 87%, 88%, 89%, 90%, 91%, 92%, 93%, 94%, 95%, 96%, 97%, 98%, 99% or greater than 99% similar to SEQ ID NO: 4.

Examples of mutations created and identified in SBEIIa in the D genome of wheat plants are provided in Table 3. Nucleotide and amino acid changes are identified according to their positions in SEQ ID NOs: 5 and 6, respectively.

TABLE 3

Representative mutations in SBEIIa gene in the D genome

| Variety | Primer SEQ IDs. | Nucleotide Mutation | A.A. Mutation | PSSM | SIFT |
|---|---|---|---|---|---|
| Express | 25, 26 | C1708T | P60S | 13.4 | 0.03 |
| Express | 25, 26 | G1721A | S64N | −16.8 | 0.76 |
| Express | 25, 26 | G1753A | E75K | | 0.74 |
| Express | 25, 26 | G1753A | E75K | | 0.74 |
| Express | 25, 26 | G1761A | Q77= | | |

TABLE 3-continued

Representative mutations in SBEIIa gene in the D genome

| Variety | Primer SEQ IDs. | Nucleotide Mutation | A.A. Mutation | PSSM | SIFT |
|---|---|---|---|---|---|
| Express | 25, 26 | G1761A | Q77= | | |
| Express | 25, 26 | G1762A | Splice Junction | | |
| Express | 25, 26 | G1762A | Splice Junction | | |
| Express | 25, 26 | G1780A | Intron | | |
| Express | 25, 26 | G1962A | Intron | | |
| Express | 25, 26 | G2037A | Splice Junction | | |
| Express | 25, 26 | G1962A | Intron | | |
| Express | 25, 26 | G2037A | Splice Junction | | |
| Express | 25, 26 | C1999T | Intron | | |
| Express | 25, 26 | G2185A | E127K | | 0.79 |
| Express | 25, 26 | C1999T | Intron | | |
| Express | 25, 26 | C2011T | Intron | | |
| Express | 25, 26 | C2028T | Intron | | |
| Express | 25, 26 | C2028T | Intron | | |
| Express | 25, 26 | C2032T | Intron | | |
| Express | 25, 26 | G2065A | A87T | | 0.59 |
| Express | 25, 26 | G2065A | A87T | | 0.59 |
| Express | 25, 26 | G2065A | A87T | | 0.59 |
| Express | 25, 26 | G2079A | M91I | | 0.76 |
| Express | 25, 26 | G2086A | G94R | | 0.15 |
| Express | 25, 26 | G2087A | G94E | | 0.43 |
| Express | 25, 26 | G2126A | G107D | | 0.53 |
| Express | 25, 26 | G2131A | V109M | | 0.14 |
| Express | 25, 26 | G2134A | E110K | | 0.64 |
| Express | 25, 26 | G2149A | G115S | | 0.37 |
| Express | 25, 26 | G2149A | G115S | | 0.37 |
| Express | 25, 26 | G2183A | G126E | | 1 |
| Express | 25, 26 | G2187A | E127= | | |
| Express | 25, 26 | G2220A | G138= | | |
| Express | 25, 26 | C2266T | H154Y | 16.9 | 0.03 |
| Express | 25, 26 | C2286T | Intron | | |
| Express | 25, 26 | C2303T | Intron | | |
| Express | 27, 28 | C3589T | S242= | | |
| Express | 27, 28 | C3602T | H247Y | 23.2 | 0 |
| Express | 27, 28 | C3607A | G248= | | |
| Express | 27, 28 | C3611G | R250G | 16 | 0.01 |
| Express | 27, 28 | G3649A | Intron | | |
| Express | 27, 28 | G3677A | Intron | | |
| Express | 27, 28 | G3677A | Intron | | |
| Express | 27, 28 | C3743T | S266F | 16.9 | 0 |
| Express | 27, 28 | C3753T | I269= | | |
| Express | 27, 28 | C3772T | P276S | 9.5 | 0.35 |
| Express | 27, 28 | G3793A | G283S | 10.9 | 0.08 |
| Express | 27, 28 | G3794A | G283D | 16.3 | 0.01 |
| Express | 27, 28 | G3824A | Intron | | |
| Express | 27, 28 | G4083A | Intron | | |
| Express | 27, 28 | C4119T | F296= | | |
| Express | 27, 28 | C4126T | P299S | 9 | 0.15 |
| Express | 27, 28 | C4127T | P299L | 18.1 | 0.01 |
| Express | 29, 30 | G4818A | E320K | 7.9 | 0.11 |
| Express | 29, 30 | G4839A | A327T | 9.2 | 0.24 |
| Express | 29, 30 | G4850A | R330= | | |
| Express | 29, 30 | G4850A | R330= | | |
| Express | 29, 30 | G4851A | D331N | 13 | 0.02 |
| Express | 29, 30 | G4939A | G360E | 24.5 | 0 |
| Express | 29, 30 | C5118T | Y361= | | |
| Express | 29, 30 | G5144A | S370N | 22.9 | 0 |
| Express | 29, 30 | G5156A | G374E | 24.5 | 0 |
| Express | 29, 30 | G5156A | G374E | 24.5 | 0 |
| Express | 29, 30 | G5166A | E377= | | |
| Express | 29, 30 | C5169T | D378= | | |
| Express | 29, 30 | G5204A | G390D | 22.8 | 0 |
| Express | 29, 30 | G5258A | Intron | | |
| Express | 29, 30 | C5267T | Intron | | |
| Express | 29, 30 | C5275T | Intron | | |
| Express | 29, 30 | G5299A | Intron | | |
| Express | 31, 32 | G6793A | A499T | 18.7 | 0 |
| Express | 31, 32 | C6163T | Intron | | |
| Express | 31, 32 | G6793A | A499T | 18.7 | 0 |
| Express | 31, 32 | C6163T | Intron | | |
| Express | 31, 32 | G6793A | A499T | 18.7 | 0 |
| Express | 31, 32 | C6163T | Intron | | |
| Express | 31, 32 | G6174A | Intron | | |
| Express | 31, 32 | C6183T | Intron | | |
| Express | 31, 32 | C6227T | T406= | | |
| Express | 31, 32 | G6258A | D417N | 6.8 | 0.15 |
| Express | 31, 32 | G6258A | D417N | 6.8 | 0.15 |
| Express | 31, 32 | C6275T | H422= | | |
| Express | 31, 32 | G6277A | G423D | 0.6 | 0.45 |
| Express | 31, 32 | G6277A | G423D | 0.6 | 0.45 |
| Express | 31, 32 | G6286A | R426H | 21.5 | 0 |
| Express | 31, 32 | G6286A | R426H | 21.5 | 0 |
| Express | 31, 32 | G6305A | W432* | | |
| Express | 31, 32 | G6306A | D433N | 20.1 | 0.01 |
| Express | 31, 32 | G6306A | D433N | 20.1 | 0.01 |
| Express | 31, 32 | C6320T | F437= | | |
| Express | 31, 32 | G6327A | G440R | 17.2 | 0 |
| Express | 31, 32 | G6328A | G440E | 17.3 | 0 |
| Express | 31, 32 | G6329A | G440= | | |
| Express | 31, 32 | G6335A | W442* | | |
| Express | 31, 32 | G6336A | E443K | 9.4 | 0.02 |
| Express | 31, 32 | C6418T | Intron | | |
| Express | 31, 32 | G6426A | Splice Junction | | |
| Express | 31, 32 | C6442T | L449= | | |
| Express | 31, 32 | C6442T | L449= | | |
| Express | 31, 32 | G6451A | A452T | 13.2 | 0.08 |
| Express | 31, 32 | G6459A | W454* | | |
| Express | 31, 32 | C6463T | L456F | 11.6 | 0.02 |
| Express | 31, 32 | C6496A | D467N | 23.2 | 0 |
| Express | 31, 32 | C6525T | H476= | | |
| Express | 31, 32 | C6526T | H477Y | 21.5 | 0 |
| Express | 31, 32 | G6538A | Splice Junction | | |
| Express | 31, 32 | G6761A | G488D | −0.9 | 0.32 |
| Express | 31, 32 | G6761A | G488D | −0.9 | 0.32 |
| Express | 31, 32 | G6793A | A499T | 18.7 | 0 |
| Express | 31, 32 | G6796A | V500I | 5.8 | 0.15 |
| Express | 31, 32 | G6844A | D516N | 1.2 | 0.42 |
| Express | 31, 32 | C6854T | S519F | 11.1 | 0 |
| Express | 31, 32 | G6860A | G521D | 15.5 | 0 |
| Express | 31, 32 | G6860A | G521D | 15.5 | 0 |
| Express | 31, 32 | G6862A | E522K | 20.2 | 0 |
| Express | 31, 32 | G6881A | Intron | | |
| Express | 31, 32 | C6898T | Intron | | |

In one embodiment, the invention relates to a polynucleotide of the SBEIIa gene of the D genome with one or more non-transgenic mutations listed in Table 3 and corresponding to SEQ ID NO: 5. In another embodiment, the polynucleotide with one or more non-transgenic mutations listed in Table 3 is 85%, 86%, 87%, 88%, 89%, 90%, 91%, 92%, 93%, 94%, 95%, 96%, 97%, 98%, 99% or greater than 99% identical to SEQ ID NO: 5. In yet another embodiment, the polynucleotide with one or more non-transgenic mutations listed in Table 3 is 85%, 86%, 87%, 88%, 89%, 90%, 91%, 92%, 93%, 94%, 95%, 96%, 97%, 98%, 99% or greater than 99% similar to SEQ ID NO: 5.

In still another embodiment, the polynucleotide with one or more non-transgenic mutation listed in Table 3 codes for a SBEIIa protein, wherein the SBEIIa protein comprises one or more non-transgenic mutations and is 85%, 86%, 87%, 88%, 89%, 90%, 91%, 92%, 93%, 94%, 95%, 96%, 97%, 98%, 99% or greater than 99% identical to SEQ ID NO: 6. In still another embodiment, the polynucleotide with one or more non-transgenic mutation listed in Table 3 codes for a SBEIIa protein, wherein the SBEIIa protein comprises one or more non-transgenic mutations and is 85%, 86%, 87%, 88%, 89%, 90%, 91%, 92%, 93%, 94%, 95%, 96%, 97%, 98%, 99% or greater than 99% similar to SEQ ID NO: 6.

2. SBEIIb Genes

In another embodiment, one or more non-transgenic mutations are in the SBEIIb gene. In one embodiment, the invention relates to multiple non-transgenic mutations in the SBEIIb gene including but not limited to 1, 2, 3, 4, 5, 6, 7, 8, 9, 10, and greater than 10 mutations.

In still another embodiment, one or more mutations are in the SBEIIb gene of the A genome. In another embodiment, one or more mutations are in the SBEIIb gene of the B genome. In still another embodiment, one or more mutations are in the SBEIIb gene of the D genome. In yet another embodiment, one or more mutations are in the SBEIIb genes of the A and B genomes. In still another embodiment, one or more mutations are in the SBEIIb genes of the A and D genomes. In another embodiment, one or more mutations are in the SBEIIb genes of the B and D genomes. In yet another embodiment, one or more mutations are in the SBEIIb genes of the A, B, and D genomes.

In one embodiment, one or more non-transgenic mutations are in both alleles of the SBEIIb gene in the A genome. In another embodiment, the non-transgenic mutations are identical in both alleles of the SBEIIb gene of the A genome.

In one embodiment, one or more non-transgenic mutations are in both alleles of the SBEIIb gene in the B genome. In another embodiment, the non-transgenic mutations are identical in both alleles of the SBEIIb gene of the B genome.

In one embodiment, one or more non-transgenic mutations are in both alleles of the SBEIIb gene in the D genome. In another embodiment, the non-transgenic mutations are identical in both alleles of the SBEIIb gene of the D genome.

Examples of mutations created and identified in SBEIIb in the A genome of wheat plants are provided in Table 4. Nucleotide and amino acid changes are identified according to their positions in SEQ ID NOs: 7 and 8, respectively.

TABLE 4

Representative Mutations in SBEIIb in the A genome

| Variety | Primer SEQ IDs. | Nucleotide Mutation | A.A. Mutation | PSSM | SIFT |
|---|---|---|---|---|---|
| Express | 33, 34 | G211A | Intron | | |
| Express | 33, 34 | G278A | W59* | | |
| Express | 33, 34 | G298A | G66D | 6.1 | 0.03 |
| Express | 33, 34 | G310A | G70E | 2.1 | 0.83 |
| Express | 33, 34 | G310A | G70E | 2.1 | 0.83 |
| Express | 33, 34 | C437T | Intron | | |
| Express | 33, 34 | G485A | Intron | | |
| Express | 33, 34 | G547A | V99I | | 0.84 |
| Express | 33, 34 | G565A | E105K | | 0.11 |
| Express | 33, 34 | G678A | T142= | | |
| Express | 33, 34 | G680A | G143E | | 1 |
| Express | 33, 34 | G709A | G153R | 8.6 | 0.03 |
| Express | 33, 34 | C739T | P163S | 10.2 | 0.09 |
| Express | 33, 34 | C743T | T164M | −3.4 | 0.21 |
| Express | 33, 34 | G769A | E173K | −4.1 | 0.56 |
| Express | 35, 36 | G1237A | E201K | 16.7 | 0.21 |
| Express | 35, 36 | C1307T | Intron | | |
| Express | 35, 36 | C1319T | Intron | | |
| Express | 35, 36 | C1322T | Intron | | |
| Express | 35, 36 | G1341A | G211S | 14.9 | 0.02 |
| Express | 35, 36 | G1356A | E216K | 22.3 | 0 |
| Express | 35, 36 | C1857T | Intron | | |
| Express | 37, 38 | C2021T | Intron | | |
| Express | 37, 38 | C2021T | Intron | | |
| Express | 35, 36 | G2031A | Intron | | |
| Express | 37, 38 | C2072T | Intron | | |
| Express | 37, 38 | C2124T | S259L | | 0.03 |
| Express | 37, 38 | C2126T | P260S | | 0.23 |
| Express | 37, 38 | G2142A | G265D | 3.6 | 0.17 |
| Express | 37, 38 | G2142A | G265D | 3.6 | 0.17 |
| Express | 37, 38 | G2142A | G265D | 3.6 | 0.17 |

TABLE 4-continued

Representative Mutations in SBEIIb in the A genome

| Variety | Primer SEQ IDs. | Nucleotide Mutation | A.A. Mutation | PSSM | SIFT |
|---|---|---|---|---|---|
| Express | 37, 38 | G2156A | Splice Junction | | |
| Express | 37, 38 | C2169T | Intron | | |
| Express | 37, 38 | C2174T | Intron | | |
| Express | 37, 38 | G2244A | G273S | 0.6 | 0.31 |
| Express | 37, 38 | G2245A | G273D | −9.5 | 1 |
| Express | 37, 38 | C2250T | P275S | 11.4 | 0.13 |
| Express | 37, 38 | G2282A | W285* | | |
| Express | 37, 38 | G2282A | W285* | | |
| Express | 37, 38 | G2282A | W285* | | |
| Express | 37, 38 | C2293T | S289F | 8.4 | 0.02 |
| Express | 37, 38 | C2340T | P305S | 15.8 | 0 |
| Express | 37, 38 | C2344T | P306L | 17.3 | 0 |
| Express | 37, 38 | C2344T | P306L | 17.3 | 0 |
| Express | 37, 38 | G2349A | E308K | | 0.07 |
| Express | 37, 38 | A2441T | Intron | | |
| Express | 37, 38 | C2484T | Intron | | |
| Express | 37, 38 | G2525A | Intron | | |
| Express | 37, 38 | G2535A | E309K | | 0.03 |
| Express | 37, 38 | G2540A | K310= | | |
| Express | 37, 38 | C2556T | P316S | 11.5 | 0.07 |
| Express | 37, 38 | C2606T | G332= | | |
| Express | 37, 38 | C2606T | G332= | | |
| Express | 37, 38 | C2617T | P336L | 18.2 | 0.01 |
| Express | 37, 38 | C2642T | Intron | | |
| Express | 37, 38 | G2697A | Intron | | |

In one embodiment, the invention relates to a polynucleotide of the SBEIIb gene of the A genome with one or more non-transgenic mutations listed in Table 4 and corresponding to SEQ ID NO: 7. In another embodiment, the polynucleotide with one or more non-transgenic mutations listed in Table 4 is 85%, 86%, 87%, 88%, 89%, 90%, 91%, 92%, 93%, 94%, 95%, 96%, 97%, 98%, 99% or greater than 99% identical to SEQ ID NO: 7. In yet another embodiment, the polynucleotide with one or more non-transgenic mutations listed in Table 4 is 85%, 86%, 87%, 88%, 89%, 90%, 91%, 92%, 93%, 94%, 95%, 96%, 97%, 98%, 99% or greater than 99% similar to SEQ ID NO: 7.

In still another embodiment, the polynucleotide with one or more non-transgenic mutation listed in Table 4 codes for a SBEIIb protein, wherein the SBEIIb protein comprises one or more non-transgenic mutations and is 85%, 86%, 87%, 88%, 89%, 90%, 91%, 92%, 93%, 94%, 95%, 96%, 97%, 98%, 99% or greater than 99% identical to SEQ ID NO: 8. In still another embodiment, the polynucleotide with one or more non-transgenic mutation listed in Table 4 codes for a SBEIIb protein, wherein the SBEIIb protein comprises one or more non-transgenic mutations and is 85%, 86%, 87%, 88%, 89%, 90%, 91%, 92%, 93%, 94%, 95%, 96%, 97%, 98%, 99% or greater than 99% similar to SEQ ID NO: 8.

Examples of mutations created and identified in SBEIIb in the B genome of wheat plants are provided in Table 5. Nucleotide and amino acid changes are identified according to their positions in SEQ ID NOs: 9 and 10, respectively.

TABLE 5

Representative mutations in the SBEIIb gene in the B genome

| Variety | Primer SEQ IDs. | Nucleotide Mutation | A.A. Mutation | PSSM | SIFT |
|---|---|---|---|---|---|
| Express | 41, 42 | G371A | G58R | | 0.26 |
| Express | 41, 42 | C422T | P75S | 20.4 | 0.02 |
| Express | 41, 42 | G435A | S79N | | 0.31 |

TABLE 5-continued

Representative mutations in the SBEIIb gene in the B genome

| Variety | Primer SEQ IDs. | Nucleotide Mutation | A.A. Mutation | PSSM | SIFT |
|---|---|---|---|---|---|
| Express | 41, 42 | C1033T | Intron | | |
| Express | 41, 42 | C1102T | Intron | | |
| Express | 41, 42 | C1102T | Intron | | |
| Express | 41, 42 | G1209A | D129N | 0.48 | |
| Express | 41, 42 | C1246T | S141F | | 0.07 |
| Express | 41, 42 | G1254A | E144K | | 0.91 |
| Express | 43, 44 | G1916A | S208N | | |
| Express | 43, 44 | C2196T | Intron | | |
| Express | 43, 44 | C2206T | Intron | | |
| Express | 43, 44 | G2221A | A225T | 6.9 | 0.21 |
| Express | 45, 46 | C2669T | Intron | | |
| Express | 45, 46 | C2776T | P260S | 10.4 | 0.21 |
| Express | 45, 46 | C2786T | P263L | 25.5 | 0.00 |
| Express | 45, 46 | C2786T | P263L | 25.5 | 0.00 |
| Express | 45, 46 | C2919T | S281L | 9.9 | 0.09 |
| Express | 45, 46 | C2786T | P263L | 25.5 | 0.00 |
| Express | 45, 46 | G3216A | K319= | | |
| Express | 45, 46 | C3232T | R325W | 27.3 | 0.00 |
| Express | 45, 46 | G3260A | S334N | 21.8 | 0.00 |
| Express | 47, 48 | C3478T | Intron | | |
| Express | 47, 48 | G3519A | Intron | | |
| Express | 47, 48 | G3678A | Intron | | |
| Express | 47, 48 | G3814A | Intron | | |
| Express | 47, 48 | C3884T | Intron | | |
| Express | 47, 48 | C3993T | L357F | 8.5 | 0.11 |
| Express | 47, 48 | G4087A | Intron | | |
| Express | 47, 48 | C4419T | Intron | | |
| Express | 47, 48 | G4280A | Intron | | |
| Express | 47, 48 | C4298T | Intron | | |
| Express | 47, 48 | C4374T | Intron | | |
| Express | 47, 48 | C4374T | Intron | | |
| Express | 47, 48 | C4422T | Intron | | |
| Express | 47, 48 | C4489T | Intron | | |

In one embodiment, the invention relates to a polynucleotide of the SBEIIb gene of the B genome with one or more non-transgenic mutations listed in Table 5 and corresponding to SEQ ID NO: 9. In another embodiment, the polynucleotide with one or more non-transgenic mutations listed in Table 5 is 85%, 86%, 87%, 88%, 89%, 90%, 91%, 92%, 93%, 94%, 95%, 96%, 97%, 98%, 99% or greater than 99% identical to SEQ ID NO: 9. In yet another embodiment, the polynucleotide with one or more non-transgenic mutations listed in Table 5 is 85%, 86%, 87%, 88%, 89%, 90%, 91%, 92%, 93%, 94%, 95%, 96%, 97%, 98%, 99% or greater than 99% similar to SEQ ID NO: 9.

In still another embodiment, the polynucleotide with one or more non-transgenic mutation listed in Table 5 codes for a SBEIIb protein, wherein the SBEIIb protein comprises one or more non-transgenic mutations and is 85%, 86%, 87%, 88%, 89%, 90%, 91%, 92%, 93%, 94%, 95%, 96%, 97%, 98%, 99% or greater than 99% identical to SEQ ID NO: 10. In still another embodiment, the SBEIIb protein with one or more non-transgenic mutations is 85%, 86%, 87%, 88%, 89%, 90%, 91%, 92%, 93%, 94%, 95%, 96%, 97%, 98%, 99% or greater than 99% similar to SEQ ID NO: 10.

Examples of mutations created and identified in SBEIIb in the D genome of wheat plants are provided in Table 6. Nucleotide and amino acid changes are identified according to their positions in SEQ ID NOs: 11 and 12, respectively.

TABLE 6

Representative mutations in SBEIIb in the D genome

| Variety | Primer SEQ IDs. | Nucleotide Mutation | A.A. Mutation | PSSM | SIFT |
|---|---|---|---|---|---|
| Express | 49, 50 | G1691A | G58E | | 0.76 |
| Express | 49, 50 | C1742T | P75L | 17 | 0.01 |
| Express | 49, 50 | A1753G | S79G | 8.8 | 0.17 |
| Express | 49, 50 | T1770C | P84= | | |
| Express | 49, 50 | C1784T | P89L | | 0.28 |
| Express | 49, 50 | C1831T | Intron | | |
| Express | 49, 50 | G1840A | Intron | | |
| Express | 49, 50 | C1844T | Intron | | |
| Express | 49, 50 | C1844T | Intron | | |
| Express | 49, 50 | C2438T | Intron | | |
| Express | 49, 50 | C2438T | Intron | | |
| Express | 49, 50 | C2463T | Intron | | |
| Express | 49, 50 | C2479T | P100S | | 0.32 |
| Express | 49, 50 | T2511A | D110E | | 0.98 |
| Express | 49, 50 | C2548T | Q123* | | |
| Express | 49, 50 | G2575A | D132N | | 0.39 |
| Express | 49, 50 | G2649A | Q156= | | |
| Express | 49, 50 | C2672T | T164M | −5.3 | 0.46 |
| Express | 49, 50 | C2676T | L165= | | |
| Express | 51, 52 | C3142T | Intron | | |
| Express | 51, 52 | C3146T | Intron | | |
| Express | 51, 52 | G3159A | Intron | | |
| Express | 51, 52 | G3185A | R180K | | 1 |
| Express | 51, 52 | G3188A | R181K | | 0.81 |
| Express | 51, 52 | G3226A | D194N | 7 | 0.07 |
| Express | 51, 52 | G3226A | D194N | 7 | 0.07 |
| Express | 51, 52 | G3226A | D194N | 7 | 0.07 |
| Express | 51, 52 | G3229A | V195I | 5.1 | 0.13 |
| Express | 51, 52 | C3237T | S197= | | |
| Express | 51, 52 | C3246T | Y200= | | |
| Express | 51, 52 | G3266A | R207H | 8.9 | 0.52 |
| Express | 51, 52 | G3270A | Splice Junction | | |
| Express | 51, 52 | C3279T | Intron | | |
| Express | 51, 52 | C3292T | Intron | | |
| Express | 51, 52 | C3303T | Intron | | |
| Express | 51, 52 | C3318T | Intron | | |
| Express | 51, 52 | C3330T | Intron | | |
| Express | 51, 52 | C3332T | Intron | | |
| Express | 51, 52 | G3345A | A209T | 5.3 | 0.49 |
| Express | 51, 52 | G3345A | A209T | 5.3 | 0.49 |
| Express | 51, 52 | C3346T | A209V | 9.8 | 0.25 |
| Express | 51, 52 | C3346T | A209V | 9.8 | 0.25 |
| Express | 51, 52 | C3346T | A209V | 9.8 | 0.25 |
| Express | 51, 52 | G3364A | R215Q | 17.7 | 0.01 |
| Express | 51, 52 | C3410T | Intron | | |
| Express | 51, 52 | C3410T | Intron | | |
| Express | 51, 52 | C3416T | Intron | | |
| Express | 51, 52 | G3571A | A224T | 16.7 | 0.01 |
| Express | 51, 52 | G3599A | W233* | | |
| Express | 51, 52 | G3628A | Splice Junction | | |
| Express | 51, 52 | C3662T | Intron | | |
| Express | 51, 52 | C3662T | Intron | | |
| Express | 53, 54 | C4138T | G265= | | |
| Express | 53, 54 | C4060T | Intron | | |
| Express | 53, 54 | G4080A | G246D | | 0 |
| Express | 53, 54 | C4124T | P261S | | 0.07 |
| Express | 53, 54 | C4142T | R267W | 18 | 0 |
| Express | 53, 54 | G4144A | R267= | | |
| Express | 53, 54 | C4159T | Intron | | |
| Express | 53, 54 | C4197A | Intron | | |
| Express | 53, 54 | C4213T | Intron | | |
| Express | 53, 54 | G4229A | Splice Junction | | |
| Express | 53, 54 | G4229A | Splice Junction | | |
| Express | 53, 54 | C4246T | P275L | 16.1 | 0.05 |
| Express | 53, 54 | C4246T | P275L | 16.1 | 0.05 |
| Express | 53, 54 | G4260A | D280N | 15.8 | 0.07 |
| Express | 53, 54 | C4280T | I286= | | |
| Express | 53, 54 | G4290A | V290M | 13.3 | 0.01 |
| Express | 53, 54 | C4299T | P293S | 8.1 | 0.29 |
| Express | 53, 54 | G4303A | G294E | 4 | 0.25 |
| Express | 53, 54 | C4311T | P297S | 17.3 | 0.07 |

TABLE 6-continued

Representative mutations in SBEIIb in the D genome

| Variety | Primer SEQ IDs. | Nucleotide Mutation | A.A. Mutation | PSSM | SIFT |
|---|---|---|---|---|---|
| Express | 53, 54 | G4347A | Splice Junction | | |
| Express | 53, 54 | C4361T | Intron | | |
| Express | 53, 54 | G4515A | Intron | | |
| Express | 53, 54 | C4546T | P316S | 9.2 | 0.13 |
| Express | 53, 54 | C4546T | P316S | 9.2 | 0.13 |
| Express | 53, 54 | C4546T | P316S | 9.2 | 0.13 |
| Express | 53, 54 | C4546T | P316S | 9.2 | 0.13 |
| Express | 53, 54 | C4547T | P316L | 18.1 | 0.01 |
| Express | 53, 54 | C4573T | R325W | 22.1 | 0 |
| Express | 53, 54 | C4605T | S335= | | |
| Express | 53, 54 | G4609A | Splice Junction | | |
| Express | 53, 54 | G4609A | Splice Junction | | |
| Express | 53, 54 | C4618T | Intron | | |
| Express | 57, 58 | C7427T | D425= | | |
| Express | 57, 58 | C7450T | T433M | 12.8 | 0 |
| Express | 57, 58 | G7471A | G440D | 2.1 | 0.26 |
| Express | 57, 58 | C7488T | H446Y | 23.3 | 0 |
| Express | 57, 58 | C7506T | R452C | 25.4 | 0 |
| Express | 57, 58 | C7506T | R452C | 25.4 | 0 |
| Express | 57, 58 | G7537A | Intron | | |
| Express | 57, 58 | C7597T | Intron | | |
| Express | 57, 58 | G7635A | R463= | | |
| Express | 57, 58 | G7655A | R470K | 13.6 | 0.05 |
| Express | 57, 58 | G7669A | E475K | 17.2 | 0 |
| Express | 57, 58 | G7685A | G480D | 26 | 0 |
| Express | 57, 58 | C7689T | F481= | | |
| Express | 57, 58 | G7700A | G485D | 26 | 0 |
| Express | 57, 58 | G7702A | A486T | 5.3 | 0 |
| Express | 57, 58 | C7758T | Intron | | |
| Express | 57, 58 | C7886T | Intron | | |
| Express | 57, 58 | G7897A | V498I | | 0.13 |
| Express | 57, 58 | C7917T | Y504= | | |
| Express | 57, 58 | C7952T | A516V | 18.5 | 0 |
| Express | 57, 58 | G7968A | M521I | 18.9 | 0 |
| Express | 57, 58 | G8056A | Intron | | |

In one embodiment, the invention relates to a polynucleotide of the SBEIIb gene of the D genome with one or more non-transgenic mutations listed in Table 6 and corresponding to SEQ ID NO: 11. In another embodiment, the polynucleotide with one or more non-transgenic mutations listed in Table 6 is 85%, 86%, 87%, 88%, 89%, 90%, 91%, 92%, 93%, 94%, 95%, 96%, 97%, 98%, 99% or greater than 99% identical to SEQ ID NO: 11. In yet another embodiment, the polynucleotide with one or more non-transgenic mutations listed in Table 6 is 85%, 86%, 87%, 88%, 89%, 90%, 91%, 92%, 93%, 94%, 95%, 96%, 97%, 98%, 99% or greater than 99% similar to SEQ ID NO: 11.

In still another embodiment, the polynucleotide with one or more non-transgenic mutation listed in Table 6 codes for a SBEIIb protein, wherein the SBEIIb protein comprises one or more non-transgenic mutations and is 85%, 86%, 87%, 88%, 89%, 90%, 91%, 92%, 93%, 94%, 95%, 96%, 97%, 98%, 99% or greater than 99% identical to SEQ ID NO: 12. In still another embodiment, the SBEIIb protein with one or more non-transgenic mutations is 85%, 86%, 87%, 88%, 89%, 90%, 91%, 92%, 93%, 94%, 95%, 96%, 97%, 98%, 99% or greater than 99% similar to SEQ ID NO: 12.

3. Mutations in Both SBEIIa and SBEIIb Genes

In one embodiment, the invention relates to multiple non-transgenic mutations in the SBEIIa gene including but not limited to 1, 2, 3, 4, 5, 6, 7, 8, 9, 10, and greater than 10 mutations and multiple non-transgenic mutations in the SBEIIb gene including but not limited to 1, 2, 3, 4, 5, 6, 7, 8, 9, 10, and greater than 10 mutations.

In still another embodiment, one or more mutations are in each of the SBEIIa and SBEIIb genes of the A genome. In one embodiment, the invention relates to multiple non-transgenic mutations in the SBEIIa gene including but not limited to 1, 2, 3, 4, 5, 6, 7, 8, 9, 10, and greater than 10 mutations and multiple non-transgenic mutations in the SBEIIb gene including but not limited to 1, 2, 3, 4, 5, 6, 7, 8, 9, 10, and greater than 10 mutations.

In another embodiment, one or more mutations are in each of the SBEIIa and SBEIIb genes of the B genome. In still another embodiment, one or more mutations are in each of the SBEIIa and SBEIIb genes of the D genome. In yet another embodiment, one or more mutations are in each of the SBEIIa and SBEIIb genes of the A and B genomes. In still another embodiment, one or more mutations are in each of the SBEIIa and SBEIIb genes of the A and D genomes. In another embodiment, one or more mutations are in each of the SBEIIa and SBEIIb genes of the B and D genomes. In yet another embodiment, one or more mutations are in each of the SBEIIa and SBEIIb genes of the A, B, and D genomes. In yet another embodiment, one or more mutations are in each of the SBEIIa genes of the A, B, and D genomes and additional mutations are in more or more of the SBEIIb genes of the A, B, and D genomes.

B. SBEII Proteins

Starch is a mixture of amylose and amylopectin, both of which are Glc polymers. Amylose is a mostly linear polymer of 200 to 2000 α-1,4-bonded Glc moieties with rare α-1,6 branch points (for reviews, see Martin and Smith, 1995; Ball et al., 1996). Amylopectin is highly α-1,6-branched, with a complex structure of $10^6$ to $10^8$ $M_r$ and up to $3 \times 10^6$ Glc subunits, making it one of the largest biological molecules in nature.

In the plant, starch is deposited as starch granules in chloroplasts of photosynthetic tissues or in amyloplasts of endosperm, embryos, tubers, and roots. In most plants, starch consists of 20% to 30% amylose and 70% to 80% amylopectin. In photosynthetic and nonphotosynthetic tissues the Glc moiety of ADP-Glc is incorporated in the growing amylose polymer with the help of starch synthases. The formation of α-1,6 linkages in amylopectin is catalyzed by SBEs.

In yet another embodiment, the invention relates to one or more non-trangenic mutations in the SBEII gene (as discussed above in the section entitled SBEII Mutations) that result in an SBEII protein with one or more mutations as compared to wild type SBEII protein. In one embodiment, the non-trangenic mutations include but are not limited to the mutations recited in Tables 1-6 and 8-12, corresponding mutations in homoeologues, and combinations thereof.

In another embodiment, the invention relates to one or more non-transgenic mutations in the SBEII gene that inhibits production of the SBEII protein. In some embodiments, a mutation in the SBEII gene inhibits expression of the SBEII protein. In other embodiments, a mutation in the SBEII gene creates an unstable or reduced function SBEII protein.

In another embodiment, the expression level of SBEII protein with one or more mutations disclosed herein is reduced to 0-2%, 2-5%, 5-7%, 7-10%, 10-15%, 15-20%, 20-25%, 25-30%, 30-35%, 35-40%, 40-45%, 45-50%, 50-60%, 60-70%, 70-80%, 80-90%, 90-95%, and 95-99% of the expression level of the wild type SBEII protein.

In yet another embodiment, the expression level of SBEIIa protein with one or more mutations disclosed herein is reduced to 0-2%, 2-5%, 5-7%, 7-10%, 10-15%, 15-20%, 20-25%, 25-30%, 30-35%, 35-40%, 40-45%, 45-50%, 50-60%, 60-70%, 70-80%, 80-90%, 90-95%, and 95-99% of the expression level of the wild type SBEIIa protein.

In still another embodiment, the expression level of SBEIIb protein with one or more mutations disclosed herein is reduced to 0-2%, 2-5%, 5-7%, 7-10%, 10-15%, 15-20%, 20-25%, 25-30%, 30-35%, 35-40%, 40-45%, 45-50%, 50-60%, 60-70%, 70-80%, 80-90%, 90-95%, and 95-99% of the expression level of the wild type SBEIIb protein.

In yet another embodiment, the activity of the SBEII protein with one or more mutations disclosed herein is reduced to 0-1, 1, 2, 3, 4, 5, 6, 7, 8, 9, 10, 11, 1.2, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 69, 69, 70, 71, 72, 73, 74, 75, 76, 77, 78, 79, 80, 81, 82, 83, 84, 85, 86, 87, 88, 89, 90, 91, 92, 93, 94, 95, 86, 97, 98, 99% and greater than 99% of the activity level of the wild type SBEII protein. In another embodiment, the SBEII protein with one or more mutations disclosed herein has no activity or zero activity as compared to wild type SBEII protein.

In still another embodiment, the activity of the SBEIIa protein with one or more mutations disclosed herein is reduced to 0-1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 69, 69, 70, 71, 72, 73, 74, 75, 76, 77, 78, 79, 80, 81, 82, 83, 84, 85, 86, 87, 88, 89, 90, 91, 92, 93, 94, 95, 86, 97, 98, 99% and greater than 99% of the activity level of the wild type SBEIIa protein. In another embodiment, the SBEIIa protein with one or more mutations disclosed herein has no activity or zero activity as compared to wild type SBEIIa protein.

In yet another embodiment, the activity of the SBEIIb protein with one or more mutations disclosed herein is reduced to 0-1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 69, 69, 70, 71, 72, 73, 74, 75, 76, 77, 78, 79, 80, 81, 82, 83, 84, 85, 86, 87, 88, 89, 90, 91, 92, 93, 94, 95, 86, 97, 98, 99% and greater than 99% of the activity level of the wild type SBEIIb protein. In another embodiment, the SBEIIb protein with one or more mutations disclosed herein has no activity or zero activity as compared to wild type SBEIIb protein.

C. Wheat Cultivars

In one embodiment, a wheat cultivar having at least one SBEII gene that is diploid, polyploid, tertraploid, and hexaploid may be used.

In another embodiment, the wheat is *Triticum aestivum*.

In one embodiment, any cultivar of wheat can be used to create mutations in an SBEII gene. In one embodiment, any cultivar of wheat can be used to create mutations in an SBEIIa gene. In another embodiment, any cultivar of wheat can be used to create mutations in an SBEIIb gene.

In one embodiment, any cultivar of wheat can be used as lines to cross SBEII mutations into different cultivars. In still another embodiment, any cultivar of wheat can be used as lines to cross SBEIIa mutations into different cultivars. In another embodiment, any cultivar of wheat can be used as lines to cross SBEIIb mutations into different cultivars.

In another embodiment, any cultivar of wheat having at least one SBEII gene may be used including but not limited to hard red spring wheat, hard white wheat, durum wheat, soft white spring wheat, soft white winter wheat, hard red winter wheat, common wheat, splelt wheat, emmer wheat, pasta wheat and *turgidum* wheat.

In one embodiment, hard red spring wheat includes but is not limited to Bullseye, Cabernet, Cal Rojo, Hank, Joaquin, Kelse, Lariat, Lassik, Malbec, Mika, PR 1404, Redwing, Summit 515, SY 314, Triple IV, Ultra, WB-Patron, WB-Rockland, Yecora Rojo, Accord, Aim, Anza, Baker, Beth Hashita, Bonus, Borah, Brim, Brooks, Buck Pronto, Butte 86, Cavalier, Challenger, Chief, Ciano T79, Colusa, Companion, Copper, Cuyama, Dash 12, Eldon, Enano, Express, Expresso, Jefferson, Genero F81, Grandin, Helena 554, Hollis, Imuris T79, Inia 66R, Jerome, Kern, Len, Marshall, McKay, Nomad, Northwest 10, Oslo, Pavon F76, Pegasus, Pitic 62, Poco Red, Powell, Probrand 711, Probrand 751, Probrand 771, Probrand 775, Probred, Prointa Queguay, Prointa Quintal, Rich, RSI 5, Sagittario, Scarlet, Serra, Shasta, Solano, Spillman, Sprite, Stander, Stellar, Stoa, Success, Summit, Sunstar 2, Sunstar King, Tadinia, Tammy, Tanori 71, Tara 2000, Tempo, Tesia T79, Topic, UI Winchester, Vance, Vandal, W444, Wampum, Wared, WB-Fuzion, Westbred 906R, Westbred 911, Westbred 926, Westbred 936, Westbred Discovery, Westbred Rambo, Yolo, and Zeke.

In another embodiment, hard white wheat includes but is not limited to Blanca Fuerte, Blanca Grande 515, Blanca Royale, Clear White, Patwin, Patwin 515, WB-Cristallo, WB-Paloma, WB-Perla, Alta Blanca, Blanca Grande, Delano, Golden Spike, ID377S, Klasic, Lochsa, Lolo, Macon, Otis, Phoenix, Pima 77, Plata, Pristine, Ramona 50, Siete Cerros 66, Vaiolet, and Winsome.

In yet another embodiment, durum wheat includes but is not limited to Crown, Desert King, Desert King HP, Duraking, Fortissimo, Havasu, Kronos, Maestrale, Normanno, Orita, Platinum, Q-Max, RSI 59, Saragolla, Tango, Tipai, Topper, Utopia, Volante, WB-Mead, Westmore, Aldente, Aldura, Altar 84, Aruba, Bittern, Bravadur, Candura, Cortez, Deluxe, Desert Titan, Durex, Durfort, Eddie, Germains 5003D, Imperial, Kofa, Levante, Matt, Mead, Mexicali 75, Minos, Modoc, Mohawk, Nudura, Ocotillo, Produra, Reva, Ria, Septre, Sky, Tacna, Titan, Trump, Ward, Westbred 803, Westbred 881, Westbred 883, Westbred 1000D, Westbred Laker, Westbred Turbo, and Yavaros 79.

In another embodiment, soft white spring wheat includes but is not limited to Alpowa, Alturas, Babe, Diva, JD, New Dirkwin, Nick, Twin, Whit, Blanca, Bliss, Calorwa, Centennial, Challis, Dirkwin, Eden, Edwall, Fielder, Fieldwin, Jubilee, Louise, Owens, Penawawa, Pomerelle, Sterling, Sunstar Promise, Super Dirkwin, Treasure, UI Cataldo, UI Pettit, Urquie, Vanna, Waduel, Waduel 94, Wakanz, Walladay, Wawawai, Whitebird, and Zak.

In still another embodiment, soft white winter wheat includes but is not limited to AP Badger, AP Legacy, Brundage 96, Bruneau, Cara, Goetze, Legion, Mary, Skiles, Stephens, SY Ovation, Tubbs, WB-Junction, WB-528, Xerpha, Yamhill, Barbee, Basin, Bitterroot, Bruehl, Castan, Chukar, Coda, Daws, Edwin, Eltan, Faro, Finch, Foote, Gene, Hill 81, Hiller, Hubbard, Hyak, Hyslop, Idaho 587, Kmor, Lambert, Lewjain, MacVicar, Madsen, Malcolm, Masami, McDermid, Moro, Nugaines, ORCF-101, ORCF-102, ORCF-103, Rod, Rohde, Rulo, Simon, Salute, Temple, Tres, Tubbs 06, UICF-Brundage, WB-523, and Weatherford.

In another embodiment, hard red winter wheat includes but is not limited to Andrews, Archer, Batum, Blizzard, Bonneville, Boundary, Declo, Deloris, Finley, Garland, Hatton, Hoff, Longhorn, Manning, Meridian, Promontory, Vona, Wanser, Winridge.

In another embodiment, common wheat (hexaploid, free threshing), *Triticum aestivum* ssp *aestivum* includes but is not limited to Sonora, Wit Wolkoring, Chiddam Blanc De Mars, India-Jammu, Foisy.

In still another embodiment, spelt wheat (hexaploid, not free threshing), *Triticum aestivum* ssp *spelta* includes but is not limited to Spanish Spelt, Swiss Spelt.

In yet another embodiment, Emmer Wheat (tetraploid), *Triticum turgidum* ssp. *dicoccum* includes but is not limited to Ethiopian Blue Tinge.

In another embodiment, pasta wheat (tetraploid, free threshing), *Triticum turgidum* ssp durum includes but is not limited to Blue Beard, Durum-Iraq.

In yet another embodiment, *Turgidum* Wheat (tetraploid, free threshing), *Triticum turgidum* ssp *turgidum* includes but is not limited to Akmolinka, Maparcha.

In one embodiment, a cultivar of wheat having at least one SBEII gene with substantial percent identity to SEQ ID NO: 1, SEQ ID NO: 3, SEQ ID NO: 5, SEQ ID NO: 7, SEQ ID NO: 9, or SEQ ID NO: 11 may be used in the invention.

As used herein with regard to the wheat cultivars, "substantial percent identity" means that the DNA sequence of the gene is sufficiently similar to SEQ ID NO: 1, 3, 5, 7, 9, or 11 at the nucleotide level to code for a substantially similar protein, allowing for allelic differences (or alternate mRNA splicing) between cultivars. In accordance with one embodiment of the invention, "substantial percent identity" may be present when the percent identity in the coding region between the SBEII gene and SEQ ID NO: 1, 3, 5, 7, 9, or 11 is as low as about 85%, provided that the percent identity in the conserved regions of the gene is higher (e.g., at least about 90%). Preferably the percent identity in the coding region is 85-90%, more preferably 90-95%, and optimally, it is above 95%. Thus, one of skill in the art may prefer to utilize a wheat cultivar having commercial popularity or one having specific desired characteristics in which to create the SBEII-mutated wheat plants, without deviating from the scope and intent of the present invention. Alternatively, one of skill in the art may prefer to utilize a wheat cultivar having few polymorphisms, such as an in-bred cultivar, in order to facilitate screening for mutations within one or more SBEII genes in accordance with the present invention.

Representative Methodology for Identification of SBEII Mutations

In order to create and identify the SBEII mutations and wheat plants of the invention, a method known as TILLING was utilized. See McCallum et al., *Nature Biotechnology* 18:455-457, 2000; McCallum et al., *Plant Physiology*, 123: 439-442, 2000; U.S. Publication No. 20040053236; and U.S. Pat. No. 5,994,075, all of which are incorporated herein by reference. In the basic TILLING methodology, plant materials, such as seeds, are subjected to chemical mutagenesis, which creates a series of mutations within the genomes of the seeds' cells. The mutagenized seeds are grown into adult M1 plants and self-pollinated. DNA samples from the resulting M2 plants are pooled and are then screened for mutations in a gene of interest. Once a mutation is identified in a gene of interest, the seeds of the M2 plant carrying that mutation are grown into adult M3 plants and screened for the phenotypic characteristics associated with the gene of interest.

The hexaploid cultivar Express and the tetraploid cultivar Kronos were used.

In one embodiment, seeds from wheat are mutagenized and then grown into M1 plants. The M1 plants are then allowed to self-pollinate and seeds from the M1 plant are grown into M2 plants, which are then screened for mutations in their SBEII loci. While M1 plants can be screened for mutations in accordance with alternative embodiments of the invention, one advantage of screening the M2 plants is that all somatic mutations correspond to germline mutations.

One of skill in the art will understand that a variety of wheat plant materials, including, but not limited to, seeds, pollen, plant tissue or plant cells, may be mutagenized in order to create the SBEII-mutated wheat plants of the invention. However, the type of plant material mutagenized may affect when the plant DNA is screened for mutations. For example, when pollen is subjected to mutagenesis prior to pollination of a non-mutagenized plant, the seeds resulting from that pollination are grown into M1 plants. Every cell of the M1 plants will contain mutations created in the pollen, thus these M1 plants may then be screened for SBEII mutations instead of waiting until the M2 generation.

Mutagens that create primarily point mutations and short deletions (about 1 to about 30 nucleotides), insertions, transversions, and or transitions, such as chemical mutagens or radiation, may be used to create the mutations. Mutagens conforming with the method of the invention include, but are not limited to, ethyl methanesulfonate (EMS), methylmethane sulfonate (MMS), N-ethyl-N-nitrosourea (ENU), triethylmelamine (TEM), N-methyl-N-nitrosourea (MNU), procarbazine, chlorambucil, cyclophosphamide, diethyl sulfate, acrylamide monomer, melphalan, nitrogen mustard, vincristine, dimethylnitrosamine, N-methyl-N'-nitro-Nitrosoguanidine (MNNG), nitrosoguanidine, 2-aminopurine, 7, 12 dimethyl-benz(a)anthracene (DMBA), ethylene oxide, hexamethylphosphoramide, bisulfan, diepoxyalkanes (diepoxyoctane (DEO), diepoxybutane (BEB), and the like), 2-methoxy-6-chloro-9[3-(ethyl-2-chloro-ethyl)aminopropylamino] acridine dihydrochloride (ICR-170), and formaldehyde. Spontaneous mutations in an SBEII gene that may not have been directly caused by the mutagen can also be identified.

Any suitable method of plant DNA preparation now known or hereafter devised may be used to prepare the wheat plant DNA for SBEIIa and SBEIIb mutation screening. For example, see Chen & Ronald, *Plant Molecular Biology Reporter* 17:53-57, 1999; Stewart and Via, *Bio Techniques* 14:748-749, 1993. Additionally, several commercial kits designed for this purpose are available, including kits from Qiagen (Valencia, Calif.) and Qbiogene (Carlsbad, Calif.).

In one embodiment, prepared DNA from individual wheat plants are pooled in order to expedite screening for mutations in one or more SBEII genes of the entire population of plants originating from the mutagenized plant tissue. The size of the pooled group may be dependent upon the sensitivity of the screening method used. Preferably, groups of two or more individual wheat plants are pooled.

In another embodiment, after the DNA samples are pooled, the pools are subjected to SBEIIa or SBEIIb sequence-specific amplification techniques, such as Polymerase Chain Reaction (PCR). For a general overview of PCR, see *PCR Protocols: A Guide to Methods and Applications* (Innis, Gelfand, Sninsky, and White, eds.), Academic Press, San Diego, 1990.

Any primer specific to an SBEIIa locus or an SBEIIb locus or the sequences immediately adjacent to one of these loci may be utilized to amplify the SBEII sequences within the pooled DNA sample. Preferably, the primer is designed to amplify the regions of the SBEII locus where useful mutations are most likely to arise. Most preferably, the primer is designed to detect exonic regions of one or more SBEII genes. Additionally, it is preferable for the primer to target known polymorphic sites to design genome specific primers in order to ease screening for point mutations in a particular genome. To facilitate detection of PCR products on a gel, the PCR primer may be labeled using any conventional or hereafter devised labeling method.

In one embodiment, primers are designed based upon the SBEIIa and SBEIIb homoeologs (SEQ ID NOs: 1, 3, 5, 7, 9, and 11). Exemplary primers (SEQ ID NOs: 13-58) that have proven useful in identifying useful mutations within the SBEIIa and SBEIIb sequences are shown below in Table 1. These primers are also detailed in the Sequence Listing appended hereto.

TABLE 7

Exemplary Primers

| SEQ ID NO | Region Screened | Sequence |
| --- | --- | --- |
| 13 | Sbe2a_A_Exon2-3 | ACGGCTTTGATCATCTCCTCCCA |
| 14 | Sbe2a_A_Exon2-3 | TTTGTCTCTTTGATGTTCCCCAAAT |
| 15 | Sbe2a_A_Exon7-9 | TATGACCAGAGTATGTCTACAGCTTGGCAAT |
| 16 | Sbe2a_A_Exon7-9 | TGCATCCTAAGTGGGAAACCCTAACCA |
| 17 | Sbe2a_A_Exon12-14 | TCAATTTGGATCAGAGGGGATAGTCCA |
| 18 | Sbe2a_A_Exon12-14 | TGACAAGGTTGCCCATTTCTAATGCAA |
| 19 | Sbe2a_B_Exon2-3 | GATAGCTGGATTAGGCGATCGCCTCAGG |
| 20 | Sbe2a_B_Exon2-3 | TTGGTAGAGGAATTAGCAAAGTAAAATCCA |
| 21 | Sbe2a_B_Exon7-9 | GGTAGAACCTTTTGCATTATGTGTGCTTTTCC |
| 22 | Sbe2a_B_Exon7-9 | GCTACCTCGAAATGCAATGGAAATCTTAGAGAC |
| 23 | Sbe2a_B_Exon12-14 | CCAAGGAGGGAGTGAGGAGCTTGACTT |
| 24 | Sbe2a_B_Exon12-14 | TGTCAGCTTGAATGCCCTTGCACTTCT |
| 25 | Sbe2a_D_Exon2-3 | GATCGCGCTTCCTGAACCTGTAT |
| 26 | Sbe2a_D_Exon2-3 | CTCAGACCACGAAGGGATCTGTATG |
| 27 | Sbe2a_D_Exon7-9 | ATGAATACGTGCAACACTCCCATCTGC |
| 28 | Sbe2a_D_Exon7-9 | GGAAGCAAAGTTTTGCACTTGCCAATATG |
| 29 | Sbe2a_D_Exon10-11 | CGTCTCCAGCAAGCCATTTCCTACCTTA |
| 30 | Sbe2a_D_Exon10-11 | TTTTGCCACTAGTTTTTGCCAATTTTCC |
| 31 | Sbe2a_D_Exon12-14 | TCAATCAATTTGGATCAGAGGGAACATCA |

TABLE 7-continued

Exemplary Primers

| SEQ ID NO | Region Screened | Sequence |
| --- | --- | --- |
| 32 | Sbe2a_D_Exon12-14 | TAGCAGTGCAGGAATTTAAGTTAAACCACTATTACA |
| 33 | Sbe2b_A_Exon2-3 | CTCCCATTCTCGTTTATTCGTAGC |
| 34 | Sbe2b_A_Exon2-3 | GTTCGGTTACCATGTCACCTCAGAGC |
| 35 | Sbe2b_A_Exon4-7 | GCCAATTGAACAACAATGCCACTTCATT |
| 36 | Sbe2b_A_Exon4-7 | GAGTACCCATTCGCACCTAGATGT |
| 37 | Sbe2b_A_Exon7-9 | GCCTGTTGCACGAGCCCATTAATTACT |
| 38 | Sbe2b_A_Exon7-9 | TTCGAACAAATGGACACCAGCTTTTGAT |
| 39 | Sbe2b_A_Exon10-11 | TTATATATCAACTTATGAATCCTGAACG |
| 40 | Sbe2b_A_Exon10-11 | GTAAAGTGTTCTTTTAGCAATTTATACAAAC |
| 41 | Sbe2b_B_Exon1-3 | GCCTCCTCATTTCGCTCGCGTGGGTTTAAG |
| 42 | Sbe2b_B_Exon1-3 | AGTGACTATGAACTTCAAGAATTTCGTGATACATCA |
| 43 | Sbe2b_B_Exon4-6 | CTACAAAAAATTGAACAACGATGCCACTTCAT |
| 44 | Sbe2b_B_Exon4-6 | CCAACTATATTTACAGCTCAACTCTGG |
| 45 | Sbe2b_B_Exon7-9 | ACTGATTTTGTTCTTGCAAGACATTCA |
| 46 | Sbe2b_B_Exon7-9 | CAAATGGACACCAGCTTTTGATGC |
| 47 | Sbe2b_B_Exon10-11 | AAAGTTAGCTATATGCAGTTTAAGTTAATTTACAGGT |
| 48 | Sbe2b_B_Exon10-11 | TGTAAGATGTTCTTTCAGCAATTTATACTA |
| 49 | Sbe2b_D_Exon2-3 | ACGACGCGTGCCGATTCCGTAT |
| 50 | Sbe2a_D_Exon2-3 | GCCATTCACATCTTATCAAAGACTGTAAATTGTTT |
| 51 | Sbe2b_D_Exon4-7 | ATCCTACAAAAAATTGAACAACAATGCCACTTTC |
| 52 | Sbe2b_D_Exon4-7 | ACATGGAGCTACAGTTCAGATGTGC |
| 53 | Sbe2b_D_Exon7-9 | GCCTGTTGCACGAGCCCATTACTAGAT |
| 54 | Sbe2b_D_Exon7-9 | GGCAATTACTTGTTTCTTTGTGCAATTACTTGTT |
| 55 | Sbe2b_D_Exon10-11 | GTTTTGAATGCTCAAGAGAAGTACTAGT |
| 56 | Sbe2b_D_Exon10-11 | TGTAAGATGTTCTTTCAGCAATTTATACTA |

TABLE 7-continued

Exemplary Primers

| SEQ ID NO | Region Screened | Sequence |
|---|---|---|
| 57 | Sbe2b_D_Exon12-14 | TTATGTCTTGGTCCAAAGCCCCT TTTTG |
| 58 | Sbe2b_D_Exon12-14 | TCCACGTCAGGAACTTAGACATG CAACTAT |

In another embodiment, the PCR amplification products may be screened for SBEII mutations using any method that identifies nucleotide differences between wild type and mutant sequences. These may include, for example, without limitation, sequencing, denaturing high pressure liquid chromatography (dHPLC), constant denaturant capillary electrophoresis (CDCE), temperature gradient capillary electrophoresis (TGCE) (see Li et al., Electrophoresis 23(10):1499-1511, 2002), or by fragmentation using enzymatic cleavage, such as used in the high throughput method described by Colbert et al., Plant Physiology 126:480-484, 2001. Preferably, the PCR amplification products are incubated with an endonuclease that preferentially cleaves mismatches in heteroduplexes between wild type and mutant sequences.

In another embodiment, cleavage products are electrophoresed using an automated sequencing gel apparatus, and gel images are analyzed with the aid of a standard commercial image-processing program.

In yet another embodiment, once an M2 plant having a mutated SBEII gene sequence is identified, the mutations are analyzed to determine their effect on the expression, translation, and/or activity of an SBEII enzyme. In one embodiment, the PCR fragment containing the mutation is sequenced, using standard sequencing techniques, in order to determine the exact location of the mutation in relation to the overall SBEII sequence. Each mutation is evaluated in order to predict its impact on protein function (i.e., from completely tolerated to causing loss-of-function) using bioinformatics tools such as SIFT (Sorting Intolerant from Tolerant; Ng and Henikoff, Nucleic Acids Research 31:3812-3814, 2003), PSSM (Position-Specific Scoring Matrix; Henikoff and Henikoff, Computer Applications in the Biosciences 12:135-143, 1996) and PARSESNP (Taylor and Greene, Nucleic Acids Research 31:3808-3811, 2003). For example, a SIFT score that is less than 0.05 and a large change in PSSM score (e.g., roughly 10 or above) indicate a mutation that is likely to have a deleterious effect on protein function. These programs are known to be predictive, and it is understood by those skilled in the art that the predicted outcomes are not always accurate.

In another embodiment, if the initial assessment of a mutation in the M2 plant indicates it to be of a useful nature and in a useful position within an SBEII gene, then further phenotypic analysis of the wheat plant containing that mutation may be pursued. In hexaploid wheat, mutations in each of the A, B and D genomes usually must be combined before a phenotype can be detected. In tetraploid wheat, A and B genome mutations are combined. In addition, the mutation containing plant can be backcrossed or outcrossed two times or more in order to eliminate background mutations at any generation. Then the backcrossed or outcrossed plant can be self-pollinated or crossed in order to create plants that are homozygous for the SBEII mutations.

Several physical characteristics of these homozygous SBEII mutant plants are assessed to determine if the mutation results in a useful phenotypic change in the wheat plant without resulting in undesirable negative effects, such as significantly reduced seed yields.

Methods of Producing a Wheat Plant

In another embodiment, the invention relates to a method for producing a wheat plant with increased resistant starch levels. In another embodiment, the invention relates to a method for producing a wheat plant with an increased proportion of amylose in the starch.

In another embodiment, the invention relates to a method of out-crossing SBEII gene mutations to wild type wheat. In another embodiment, the invention relates to a method of out-crossing SBEIIa gene mutations to wild type wheat. In another embodiment, the invention relates to a method of out-crossing SBEIIb gene mutations to wild type wheat.

In another embodiment, the invention relates to a method for producing a wheat plant having increased amylose content. In still another embodiment, the invention relates to a method for producing a wheat plant having reduced activity of one or more SBEII enzymes compared to the wild type wheat plants.

In one embodiment, the method comprises inducing at least one non-transgenic mutation in at least one copy of an SBEII gene in plant material or plant parts from a parent wheat plant; growing or using the mutagenized plant material to produce progeny wheat plants; analyzing mutagenized plant material and/or progeny wheat plants to detect at least one mutation in at least one copy of a SBEII gene; and selecting progeny wheat plants that have at least one mutation in at least one copy of an SBEII gene.

In another embodiment, the method further comprises crossing progeny wheat plants that have at least one mutation in at least one copy of an SBEII gene with other progeny wheat plants that have at least one mutation in a different copy of an SBEII gene. The process of identifying progeny wheat plants with mutations and crossing said progeny wheat plants with other progeny wheat plants, which have mutations, can be repeated to produce progeny wheat plants with reduced SBEII enzyme activity.

In another embodiment, the level of activity of the SBEII protein in the wheat plant is reduced and selected from the group consisting of 0-2%, 2-5%, 5-7%, 7-10%, 10-15%, 15-20%, 20-25%, 25-30%, 30-35%, 35-40%, 40-45%, 45-50%, 50-60%, 60-70%, 70-80%, 80-90%, 90-95%, 95-99% of the level of activity of the SBEII protein in the wild type plant.

In still another embodiment, the level of activity of the SBEIIa protein in the wheat plant is reduced compared to the wild type plant and is selected from the group consisting of 0-2%, 2-5%, 5-7%, 7-10%, 10-15%, 15-20%, 20-25%, 25-30%, 30-35%, 35-40%, 40-45%, 45-50%, 50-60%, 60-70%, 70-80%, 80-90%, 90-95%, 95-99% of the level of activity of the SBEIIa protein in the wild type plant.

In yet another embodiment, the level of activity of the SBEIIb protein in the wheat plant is reduced and selected from the group consisting of 0-2% 2-5%, 5-7%, 7-10%, 10-15%, 15-20%, 20-25%, 25-30%, 30-35%, 35-40%, 40-45%, 45-50%, 50-60%, 60-70%, 70-80%, 80-90%, 90-95%, 95-99% of the level of activity of the SBEIIb protein in the wild type plant.

A. Methods of Producing a Wheat Plant with One or More Mutations in the SBEIIa Gene in More than One Genome In still another embodiment, the invention relates to a method for producing a wheat plant comprising inducing at least one non-transgenic mutation in at least one copy of an SBEIIa gene in plant material from a parent wheat plant that comprises a mutation in an SBEIIa gene; growing or using the mutagenized plant material to produce progeny wheat plants; and selecting progeny wheat plants that have at least one mutation in at least two copies of an SBEIIa gene.

For example, the parent wheat plant may have a mutation in an SBEIIa gene of the A genome. The selected progeny wheat plants may have a mutation in an SBEIIa gene of the A genome and one or more mutations in the SBEIIa gene of the B genome. This example is provided merely for clarification and should not limit the methods disclosed herein.

In yet another embodiment, the invention relates to a method for producing a wheat plant comprising inducing at least one non-transgenic mutation in at least one copy of an SBEIIa gene in plant material from a parent wheat plant that comprises at least one mutation in two SBEIIa genes; growing or using the mutagenized plant material to produce progeny wheat plants; and selecting progeny wheat plants that have at least one mutation in three copies of an SBEIIa gene. In this embodiment, there would be at least one mutation in the SBEIIa gene of the A, B and D genomes.

In another embodiment, the invention relates to a method for producing a wheat plant comprising crossing a first wheat plant that has at least one non-transgenic mutation in a first SBEIIa gene with a second wheat plant that has at least one non-transgenic mutation in a second SBEIIa gene; and selecting progeny wheat plants that have at least one mutation in at least two copies of an SBEIIa gene.

In another embodiment, the invention relates to a method for producing a wheat plant comprising crossing a first wheat plant that has at least one non-transgenic mutation in a first and second SBEIIa gene with a second wheat plant that has at least one non-transgenic mutation in a third SBEIIa gene; and selecting progeny wheat plants that have at least one mutation in all three copies of an SBEIIa gene. In this embodiment, there would be at least one mutation in the SBEIIa gene of the A, B and D genomes.

In another embodiment, the grain of the wheat plant produced according to the methods disclosed herein comprises starch, and the proportion of amylose in the starch is selected from the group consisting of at least 30%, 30-35%, 35-40%, 40-45%, 45-50%, 50-55%, 55-60%, and 60-65% (w/w). In one embodiment, the proportion of amylose in the starch is 47-60% (w/w).

B. Methods of Producing a Wheat Plant with Mutations in the SBEIIb Gene in More than One Genome In still another embodiment, the invention relates to a method for producing a wheat plant comprising inducing at least one non-transgenic mutation in at least one copy of an SBEIIb gene in plant material from a parent wheat plant that comprises a mutation in an SBEIIb gene; growing or using the mutagenized plant material to produce progeny wheat plants; and selecting progeny wheat plants that have at least one mutation in at least two copies of an SBEIIb gene.

For example, the parent wheat plant may have a mutation in an SBEIIb gene of the A genome. The selected progeny wheat plants may have a mutation in an SBEIIb gene of the A genome and one or more mutations in the SBEIIb gene of the B genome. This example is provided merely for clarification and should not limit the methods disclosed herein.

In yet another embodiment, the invention relates to a method for producing a wheat plant comprising inducing at least one non-transgenic mutation in at least one copy of an SBEIIb gene in plant material from a parent wheat plant that comprises at least one mutation in two SBEIIb genes; growing or using the mutagenized plant material to produce progeny wheat plants; and selecting progeny wheat plants that have at least one mutation in three copies of an SBEIIb gene. In this embodiment, there would be at least one mutation in the SBEIIb gene of the A, B and D genomes.

In another embodiment, the invention relates to a method for producing a wheat plant comprising crossing a first wheat plant that has at least one non-transgenic mutation in a first SBEIIb gene with a second wheat plant that has at least one non-transgenic mutation in a second SBEIIb gene; and selecting progeny wheat plants that have at least one mutation in at least two copies of an SBEIIb gene.

In another embodiment, the invention relates to a method for producing a wheat plant comprising crossing a first wheat plant that has at least one non-transgenic mutation in a first and second SBEIIb gene with a second wheat plant that has at least one non-transgenic mutation in a third SBEIIb gene; and selecting progeny wheat plants that have at least one mutation in all three copies of an SBEIIb gene. In this embodiment, there would be at least one mutation in the SBEIIb gene of the A, B and D genomes.

In another embodiment, the grain of the wheat plant produced according to the methods disclosed herein comprises starch, and the proportion of amylose in the starch is selected from the group consisting of at least 30%, 30-35%, 35-40%, 40-45%, 45-50%, 55-60%, 60-65%, 65-70%, 70-75%, 75-80%, 80-85%, 85-90%, 90-95%, and greater than 95% (w/w).

C. Methods of Producing a Wheat Plant with One or More Mutations in the SBEIIa Gene and SBEIIb Gene in More than One Genome In one embodiment, the invention relates to a method of producing a wheat plant with one or more mutations in the SBEIIa gene and one or more mutations in the SBEIIb gene in one or more than one genome.

In one embodiment, the wheat plant may comprise one mutation in the SBEIIa gene and 1, 2, 3, 4, 5, 6, 7, 8, 9, 10, or more than 10 mutations in the SBEIIb gene. In one embodiment, the wheat plant may comprise 2 mutations in the SBEIIa gene and 1, 2, 3, 4, 5, 6, 7, 8, 9, 10, or more than 10 mutations in the SBEIIb gene.

In one embodiment, the wheat plant may comprise 3 mutations in the SBEIIa gene and 1, 2, 3, 4, 5, 6, 7, 8, 9, 10, or more than 10 mutations in the SBEIIb gene. In one embodiment, the wheat plant may comprise 4 mutations in the SBEIIa gene and 1, 2, 3, 4, 5, 6, 7, 8, 9, 10, or more than 10 mutations in the SBEIIb gene. In one embodiment, the wheat plant may comprise 5 mutations in the SBEIIa gene and 1, 2, 3, 4, 5, 6, 7, 8, 9, 10, or more than 10 mutations in the SBEIIb gene. In one embodiment, the wheat plant may comprise 6 mutations in the SBEIIa gene and 1, 2, 3, 4, 5, 6, 7, 8, 9, 10, or more than 10 mutations in the SBEIIb gene.

In one embodiment, the wheat plant may comprise 7 mutations in the SBEIIa gene and 1, 2, 3, 4, 5, 6, 7, 8, 9, 10, or more than 10 mutations in the SBEIIb gene. In one embodiment, the wheat plant may comprise 8 mutations in the SBEIIa gene and 1, 2, 3, 4, 5, 6, 7, 8, 9, 10, or more than 10 mutations in the SBEIIb gene. In one embodiment, the wheat plant may comprise 9 mutations in the SBEIIa gene and 1, 2, 3, 4, 5, 6, 7, 8, 9, 10, or more than 10 mutations in the SBEIIb gene. In one embodiment, the wheat plant may comprise 10 mutations in the SBEIIa gene and 1, 2, 3, 4, 5, 6, 7, 8, 9, 10, or more than 10 mutations in the SBEIIb gene.

In one embodiment, the invention relates to a method for producing a wheat plant comprising inducing at least one non-transgenic mutation in at least one copy of an SBEIIa and SBEIIb gene in plant material from a parent wheat plant that comprises a mutation in an SBEIIa and SBEIIb genes; growing or using the mutagenized plant material to produce progeny wheat plants; and selecting progeny wheat plants that have at least one mutation in at least two SBEIIa genes and at least one mutation in at least two SBEIIb genes.

For example, the parent wheat plant may have a mutation in SBEIIa and SBEIIb genes of the A genome. The selected progeny wheat plants may have a mutation in an SBEIIa and SBEIIb gene of the A genome and one or more mutations in the SBEIIa and SBEIIb genes of the B genome. This example is provided merely for clarification and should not limit the methods disclosed herein.

In yet another embodiment, the invention relates to a method for producing a wheat plant comprising inducing at least one non-transgenic mutation in at least one copy of SBEIIa and SBEIIb genes in plant material from a parent wheat plant that comprises at least one mutation in two SBEIIa genes and at least one mutation in two SBEIIb genes; growing or using the mutagenized plant material to produce progeny wheat plants; and selecting progeny wheat plants that have at least one mutation in three copies of an SBEIIa gene and at least one mutation in three copies of an SBEIIb gene. In this embodiment, there would be at least one mutation in the SBEIIa gene of the A, B and D genomes and at least one mutation in the SBEIIb gene of the A, B and D genomes.

In another embodiment, the invention relates to a method for producing a wheat plant comprising crossing a first wheat plant that has at least one non-transgenic mutation in a first SBEIIa gene and a first SBEIIb gene with a second wheat plant that has at least one non-transgenic mutation in a second SBEIIa gene and a second SBEIIb gene; and selecting progeny wheat plants that have at least one mutation in at least two copies of an SBEIIa and SBEIIb gene.

In another embodiment, the invention relates to a method for producing a wheat plant comprising crossing a first wheat plant that has at least one non-transgenic mutation in a first and second SBEIIa gene and at least one non-transgenic mutation in a first and second SBEIIb gene with a second wheat plant that has at least one non-transgenic mutation in a third SBEIIa and at least one non-transgenic mutation in a third SBEIIb gene; and selecting progeny wheat plants that have at least one mutation in all three copies of an SBEIIa and SBEIIb gene. In this embodiment, there would be at least one mutation in the SBEIIb gene of the A, B and D genomes.

In another embodiment, the grain of the wheat plant produced according to the methods disclosed herein comprises starch, and the proportion of amylose in the starch is selected from the group consisting of at least 30%, 30-35%, 35-40%, 40-45%, 45-50%, and 50-55% (w/w).

Wheat Plant, Wheat Seed and Parts of Wheat Plant

In one embodiment, a wheat plant is produced according to the methods disclosed herein. In another embodiment, the wheat plant, wheat seed or parts of a wheat plant have one or more mutations in an SBEII gene. In another embodiment, the wheat plant, wheat seed or parts of a wheat plant have one or more mutations in SBEII genes.

In another embodiment, the invention relates to a wheat plant, wheat seed or parts of a wheat plant comprising one or more non-transgenic mutations in the SBEIIa gene. In another embodiment, the invention relates to a wheat plant, wheat seed or parts of a wheat plant comprising at least one non-transgenic mutation in the SBEIIa gene in each of two genomes. In still another embodiment, the invention relates to a wheat plant, wheat seed or parts of a wheat plant comprising at least one non-transgenic mutation in the SBEIIa gene in each of three genomes.

In one embodiment, the wheat plant, wheat seed or parts of a wheat plant comprises one or more non-transgenic mutations in both alleles of the SBEIIa gene in the A genome. In another embodiment, the non-transgenic mutations are identical in both alleles of the SBEIIa gene of the A genome.

In one embodiment, the wheat plant, wheat seed or parts of a wheat plant comprises one or more non-transgenic mutations in both alleles of the SBEIIa gene in the B genome. In another embodiment, the non-transgenic mutations are identical in both alleles of the SBEIIa gene of the B genome.

In one embodiment, the wheat plant, wheat seed or parts of a wheat plant comprises one or more non-transgenic mutations in both alleles of the SBEIIa gene in the D genome. In another embodiment, the non-transgenic mutations are identical in both alleles of the SBEIIa gene of the D genome.

In one embodiment, the invention relates to a wheat plant, wheat seed or parts of a wheat plant comprising a polynucleotide of the SBEIIa gene in the A genome with one or more non-transgenic mutations listed in Table 1 and corresponding to SEQ ID NO: 1. In another embodiment, the wheat plant, wheat seed or parts of the wheat plant comprise a polynucleotide with one or more non-transgenic mutations listed in Table 1 and is 85%, 86%, 87%, 88%, 89%, 90%, 91%, 92%, 93%, 94%, 95%, 96%, 97%, 98%, 99% or greater than 99% identical or similar to SEQ ID NO: 1.

In still another embodiment, the wheat plant, wheat seed or parts of a wheat plant comprise a polynucleotide with one or more non-transgenic mutations listed in Table 1 that codes for a SBEIIa protein, wherein the SBEIIa protein comprises one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 2.

In one embodiment, the invention relates to a wheat plant, wheat seed or parts of a wheat plant comprising a polynucleotide of the SBEIIa gene in the B genome with one or more non-transgenic mutations listed in Table 2 and corresponding to SEQ ID NO: 3. In another embodiment, the wheat plant, wheat seed or parts of a wheat plant comprises a polynucleotide with one or more non-transgenic mutations listed in Table 2 is 85%, 86%, 87%, 88%, 89%, 90%, 91%, 92%, 93%, 94%, 95%, 96%, 97%, 98%, 99% or greater than 99% identical or similar to SEQ ID NO: 3.

In still another embodiment, wheat plant, wheat seed or parts of a wheat plant comprises a polynucleotide with one or more non-transgenic mutations listed in Table 2 and codes for a SBEIIa protein, wherein the SBEIIa protein comprises one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 4.

In one embodiment, the invention relates to a wheat plant, wheat seed or parts of a wheat plant comprising a polynucleotide of the SBEIIa gene of the D genome with one or more non-transgenic mutations listed in Table 3 and corresponding to SEQ ID NO: 5. In another embodiment, the wheat plant, wheat seed or parts of a wheat plant comprise a polynucleotide with one or more non-transgenic mutations listed in Table 3 and is 85%, 86%, 87%, 88%, 89%, 90%, 91%, 92%, 93%, 94%, 95%, 96%, 97%, 98%, 99% or greater than 99% identical or similar to SEQ ID NO: 5.

In still another embodiment, the wheat plant, wheat seed or parts of a wheat plant comprises a polynucleotide with one or more non-transgenic mutations listed in Table 3 and codes for a SBEIIa protein, wherein the SBEIIa protein comprises one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 6.

In still another embodiment, the invention relates to a wheat plant, wheat seed or parts of a wheat plant comprising one or more non-transgenic mutations in the SBEIIb gene. In another embodiment, the invention relates to a wheat plant, wheat seed or parts of a wheat plant comprising at least one non-transgenic mutation in the SBEIIb gene in each of two genomes. In still another embodiment, the invention relates to a wheat plant, wheat seed or parts of a wheat plant comprising at least one non-transgenic mutation in the SBEIIb gene in each of three genomes.

In one embodiment, the wheat plant, wheat seed or parts of a wheat plant comprises one or more non-transgenic mutations in both alleles of the SBEIIb gene. In one embodiment, the wheat plant, wheat seed or parts of a wheat plant comprises one or more non-transgenic mutations in both alleles of the SBEIIb gene of the A genome. In another embodiment, the non-transgenic mutations are identical in both alleles of the SBEIIb gene of the A genome.

In one embodiment, the wheat plant, wheat seed or parts of a wheat plant comprises one or more non-transgenic mutations in both alleles of the SBEIIb gene of the B genome. In another embodiment, the non-transgenic mutations are identical in both alleles of the SBEIIb gene of the B genome.

In one embodiment, the wheat plant, wheat seed or parts of a wheat plant comprises one or more non-transgenic mutations in both alleles of the SBEIIb gene of the D genome. In another embodiment, the non-transgenic mutations are identical in both alleles of the SBEIIb gene of the D genome.

In one embodiment, the invention relates to a wheat plant, wheat seed or parts of a wheat plant comprising a polynucleotide of the SBEIIb gene of the A genome with one or more non-transgenic mutations listed in Table 4 and corresponding to SEQ ID NO: 7. In another embodiment, the wheat plant, wheat seed or parts of a wheat plant comprises a polynucleotide with one or more non-transgenic mutations listed in Table 4 and is 85%, 86%, 87%, 88%, 89%, 90%, 91%, 92%, 93%, 94%, 95%, 96%, 97%, 98%, 99% or greater than 99% identical or similar to SEQ ID NO: 7.

In still another embodiment, the wheat plant, wheat seed or parts of a wheat plant comprise a polynucleotide with one or more non-transgenic mutations listed in Table 4 that codes for a SBEIIb protein, wherein the SBEIIb protein comprises one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 8.

In one embodiment, the invention relates to a wheat plant, wheat seed or parts of a wheat plant comprising a polynucleotide of the SBEIIb gene of the B genome with one or more non-transgenic mutations listed in Table 5 and corresponding to SEQ ID NO: 9. In another embodiment, the wheat plant, wheat seed or parts of a wheat plant comprise a polynucleotide with one or more non-transgenic mutations listed in Table 5 and is 85%, 86%, 87%, 88%, 89%, 90%, 91%, 92%, 93%, 94%, 95%, 96%, 97%, 98%, 99% or greater than 99% identical or similar to SEQ ID NO: 9.

In still another embodiment, the wheat plant, wheat seed or parts of a wheat plant comprise a polynucleotide with one or more non-transgenic mutations listed in Table 5 that codes for a SBEIIb protein, wherein the SBEIIb protein comprises one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 10.

In one embodiment, the invention relates to wheat plant, wheat seed or parts of a wheat plant comprising a polynucleotide of the SBEIIb gene of the D genome with one or more non-transgenic mutations listed in Table 6 and corresponding to SEQ ID NO: 11. In another embodiment, the wheat plant, wheat seed or parts of a wheat plant comprise a polynucleotide with one or more non-transgenic mutations listed in Table 6 and is 85%, 86%, 87%, 88%, 89%, 90%, 91%, 92%, 93%, 94%, 95%, 96%, 97%, 98%, 99% or greater than 99% identical or similar to SEQ ID NO: 11.

In still another embodiment, the wheat plant, wheat seed or parts of a wheat plant comprise a polynucleotide with one or more non-transgenic mutations listed in Table 6 that codes for a SBEIIb protein, wherein the SBEIIb protein comprises one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 12.

In another embodiment, the invention relates to a wheat plant, wheat seed or parts of a wheat plant comprising one or more non-transgenic mutations in the SBEIIa and SBEIIb genes. In another embodiment, the invention relates to a wheat plant, wheat seed or parts of a wheat plant comprising at least one non-transgenic mutation in the SBEIIa and SBEIIb genes in each of two genomes. In still another embodiment, the invention relates to a wheat plant, wheat seed or parts of a wheat plant comprising at least one non-transgenic mutation in the SBEIIa and SBEIIb genes in each of three genomes.

In still another embodiment, the invention relates to a wheat plant, wheat seed or parts of a wheat plant comprising at least one non-transgenic mutation in the SBEIIa gene in each of three genomes and one or more non-transgenic mutation in the SBEIIb gene.

In another embodiment, the wheat plant, wheat seed or parts of a wheat plant has one or more mutations in the SBEII gene including but not limited to one or more mutations enumerated in Tables 1-6 and 8-12 and corresponding mutations in the homoeologues. A wheat plant, wheat seed or parts of a wheat plant can be generated having 1, 2, 3, 4, 5, 6, 7, 8, 9, 10, 11, 12, 13, 14, 15, 16, 17, 18, 19, 20, 21, 22, 23, 24, 25 or greater than 25 of the mutations disclosed herein including but not limited to the mutations disclosed in Tables 1-6 and 8-12, as well as mutations in the corresponding homoeologues.

In another embodiment, a wheat plant, wheat seed or parts of a wheat plant comprising one or more non-transgenic mutations in an SBEII gene, including but not limited to the mutation listed in Tables 1-6 and 8-12 and the mutations in the corresponding homoeologues, has an increased proportion of amylose in starch as compared to the same wheat cultivar without the mutations in the SBEII gene. In yet another embodiment, the proportion of amylose in the starch is selected from the group consisting of at least 10-15%, 16-20%, 21-25%, 26-30%, 31-35%, 36-40%, 41-45%, 46-50%, 51-55%, 56-60%, 61-65%, 66-70%, 71-75%, 76-80%, 81-85%, 86-90%, 91-95%, 96%, 97%, 98%, 99%, and greater than 99% (w/w).

Grain, Flour and Starch

In another embodiment, the invention relates to a wheat grain, flour or starch comprising one or more non-transgenic mutations in the SBEII gene. In another embodiment, the invention relates to wheat grain comprising an embryo, wherein the embryo comprises one or more non-transgenic mutations in an SBEII gene.

In another embodiment, the wheat grain, flour or starch comprises one or more non-transgenic mutations in the SBEIIa and/or the SBEIIb genes including but not limited to the mutations recited in Tables 1-6 and 8-12 and the corresponding mutations in homoeologues.

In still another embodiment, the invention relates to a wheat grain, flour or starch comprising one or more non-transgenic mutations in the SBEIIa gene. In another embodiment, the invention relates to a wheat grain or flour comprising at least one non-transgenic mutation in the SBEIIa gene in each of two genomes. In still another embodiment, the invention relates to a wheat grain or flour comprising at least one non-transgenic mutation in the SBEIIa gene in each of three genomes.

In one embodiment, the wheat grain, flour or starch comprises one or more non-transgenic mutations in both alleles of the SBEIIa gene in the A genome. In another embodiment, the non-transgenic mutations are identical in both alleles of the SBEIIa gene of the A genome.

In one embodiment, the wheat grain, flour or starch comprises one or more non-transgenic mutations in both alleles of the SBEIIa gene in the B genome. In another embodiment, the non-transgenic mutations are identical in both alleles of the SBEIIa gene of the B genome.

In one embodiment, the wheat grain, flour or starch comprises one or more non-transgenic mutations in both alleles of the SBEIIa gene in the D genome. In another embodiment, the non-transgenic mutations are identical in both alleles of the SBEIIa gene of the D genome.

In one embodiment, the invention relates to wheat grain, wheat flour or starch comprising a polynucleotide of the SBEIIa gene in the A genome with one or more non-transgenic mutations listed in Table 1 and corresponding to SEQ ID NO: 1. In another embodiment, the wheat grain or wheat flour comprise a polynucleotide with one or more non-transgenic mutations listed in Table 1 and is 85%, 86%, 87%, 88%, 89%, 90%, 91%, 92%, 93%, 94%, 95%, 96%, 97%, 98%, 99% or greater than 99% identical or similar to SEQ ID NO: 1.

In still another embodiment, wheat grain, wheat flour or starch comprise a polynucleotide with one or more non-transgenic mutations listed in Table 1 that codes for a SBEIIa protein, wherein the SBEIIa protein comprises one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 2.

In one embodiment, the invention relates to wheat grain, wheat flour or starch comprising a polynucleotide of the SBEIIa gene in the B genome with one or more non-transgenic mutations listed in Table 2 and corresponding to SEQ ID NO: 3. In another embodiment, the wheat grain or wheat flour comprises a polynucleotide with one or more non-transgenic mutations listed in Table 2 is 85%, 86%, 87%, 88%, 89%, 90%, 91%, 92%, 93%, 94%, 95%, 96%, 97%, 98%, 99% or greater than 99% identical or similar to SEQ ID NO: 3.

In still another embodiment, wheat grain, wheat flour or starch comprise a polynucleotide with one or more non-transgenic mutations listed in Table 2 and codes for a SBEIIa protein, wherein the SBEIIa protein comprises one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 4.

In one embodiment, the invention relates to wheat grain, wheat flour or starch comprising a polynucleotide of the SBEIIa gene of the D genome with one or more non-transgenic mutations listed in Table 3 and corresponding to SEQ ID NO: 5. In another embodiment, the wheat grain or wheat flour comprise a polynucleotide with one or more non-transgenic mutations listed in Table 3 and is 85%, 86%, 87%, 88%, 89%, 90%, 91%, 92%, 93%, 94%, 95%, 96%, 97%, 98%, 99% or greater than 99% identical or similar to SEQ ID NO: 5.

In still another embodiment, wheat grain, wheat flour or starch comprise a polynucleotide with one or more non-transgenic mutations listed in Table 3 and codes for a SBEIIa protein, wherein the SBEIIa protein comprises one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 6.

In still another embodiment, the invention relates to a wheat grain, flour or starch comprising one or more non-transgenic mutations in the SBEIIb gene. In another embodiment, the invention relates to a wheat plant comprising at least one non-transgenic mutation in the SBEIIb gene in each of two genomes. In still another embodiment, the invention relates to a wheat plant comprising at least one non-transgenic mutation in the SBEIIb gene in each of three genomes.

In one embodiment, the wheat grain, flour or starch comprises one or more non-transgenic mutations in both alleles of the SBEIIb gene. In one embodiment, the wheat grain, flour or starch comprises one or more non-transgenic mutations in both alleles of the SBEIIb gene in each of two genomes. In one embodiment, the wheat grain, flour or starch comprises one or more non-transgenic mutations in both alleles of the SBEIIb gene in each of three genomes.

In one embodiment, the wheat grain, flour or starch comprises one or more non-transgenic mutations in both alleles of the SBEIIb gene. In one embodiment, the wheat grain, flour or starch comprises one or more non-transgenic mutations in both alleles of the SBEIIb gene of the A genome. In another embodiment, the non-transgenic mutations are identical in both alleles of the SBEIIb gene of the A genome.

In one embodiment, the wheat grain, flour or starch comprises one or more non-transgenic mutations in both alleles of the SBEIIb gene of the B genome. In another embodiment, the non-transgenic mutations are identical in both alleles of the SBEIIb gene of the B genome.

In one embodiment, the wheat grain, flour or starch comprises one or more non-transgenic mutations in both alleles of the SBEIIb gene of the D genome. In another embodiment, the non-transgenic mutations are identical in both alleles of the SBEIIb gene of the D genome.

In one embodiment, the invention relates to a wheat grain, wheat flour or starch comprising a polynucleotide of the SBEIIb gene of the A genome with one or more non-transgenic mutations listed in Table 4 and corresponding to SEQ ID NO: 7. In another embodiment, the wheat grain, wheat flour or starch comprises a polynucleotide with one or more non-transgenic mutations listed in Table 4 and is 85%, 86%, 87%, 88%, 89%, 90%, 91%, 92%, 93%, 94%, 95%, 96%, 97%, 98%, 99% or greater than 99% identical or similar to SEQ ID NO: 7.

In still another embodiment, the wheat grain, wheat flour or starch comprise a polynucleotide with one or more non-transgenic mutations listed in Table 4 that codes for a SBEIIb protein, wherein the SBEIIb protein comprises one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 8.

In one embodiment, the invention relates to wheat grain, wheat flour or starch comprising a polynucleotide of the SBEIIb gene of the B genome with one or more non-transgenic mutations listed in Table 5 and corresponding to SEQ ID NO: 9. In another embodiment, the wheat grain, wheat flour or starch comprise a polynucleotide with one or more non-transgenic mutations listed in Table 5 and is 85%, 86%, 87%, 88%, 89%, 90%, 91%, 92%, 93%, 94%, 95%, 96%, 97%, 98%, 99% or greater than 99% identical or similar to SEQ ID NO: 9.

In still another embodiment, the wheat grain, wheat flour or starch comprise a polynucleotide with one or more non-transgenic mutations listed in Table 5 that codes for a SBEIIb protein, wherein the SBEIIb protein comprises one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 10.

In one embodiment, the invention relates to wheat grain, wheat flour or starch comprising a polynucleotide of the SBEIIb gene of the D genome with one or more non-transgenic mutations listed in Table 6 and corresponding to SEQ ID NO: 11. In another embodiment, the wheat grain, wheat flour or starch comprise a polynucleotide with one or more non-transgenic mutations listed in Table 6 and is 85%, 86%, 87%, 88%, 89%, 90%, 91%, 92%, 93%, 94%, 95%, 96%, 97%, 98%, 99% or greater than 99% identical or similar to SEQ ID NO: 11.

In still another embodiment, the wheat grain, wheat flour or starch comprise a polynucleotide with one or more non-transgenic mutations listed in Table 6 that codes for a SBEIIb protein, wherein the SBEIIb protein comprises one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 12.

In another embodiment, the invention relates to a wheat grain, flour or starch comprising one or more non-transgenic mutations in the SBEIIa gene and one or more non-transgenic mutations in the SBEIIb genes. In another embodiment, the invention relates to a wheat grain, flour or starch comprising at least one non-transgenic mutation in the SBEIIa and SBEIIb genes in each of two genomes. In still another embodiment, the invention relates to a wheat grain, flour or starch comprising at least one non-transgenic mutation in the SBEIIa and SBEIIb genes in each of three genomes.

In still another embodiment, the invention relates to a wheat grain, flour or starch comprising at least one non-transgenic mutation in the SBEIIa gene in each of three genomes and one or more non-transgenic mutation in the SBEIIb gene.

In one embodiment, the wheat grain, flour or starch comprises one or more non-transgenic mutations in both alleles of the SBEIIa gene and the SBEIIb gene of the A genome. In another embodiment, the non-transgenic mutations are identical in both alleles of the SBEIIa gene and the SBEIIb gene of the A genome.

In one embodiment, the wheat grain, flour or starch comprises one or more non-transgenic mutations in both alleles of the SBEIIa gene and the SBEIIb gene of the B genome. In another embodiment, the non-transgenic mutations are identical in both alleles of the SBEIIa gene and the SBEIIb gene of the B genome.

In one embodiment, the wheat grain, flour or starch comprises one or more non-transgenic mutations in both alleles of the SBEIIa gene and the SBEIIb gene of the D genome. In another embodiment, the non-transgenic mutations are identical in both alleles of the SBEIIa gene and the SBEIIb gene of the D genome.

In still another embodiment, the invention relates to wheat grain or flour comprising an endosperm and a reduced gene expression level, activity or expression level and activity of the SBEII gene as compared to wild type wheat grain or flour.

In still another embodiment, the invention relates to wheat grain or flour comprising an endosperm and a reduced expression level, activity or expression level and activity of the SBEII protein as compared to wild type wheat grain or flour. In still another embodiment, the invention relates to wheat grain or flour comprising an endosperm and a reduced expression level, activity or expression level and activity of the SBEIIa protein as compared to wild type wheat grain or flour. In yet another embodiment, the invention relates to wheat grain or flour comprising an endosperm and a reduced expression level, activity or expression level and activity of the SBEIIb protein as compared to wild type wheat grain or flour.

In yet another embodiment, the invention relates to wheat grain or flour comprising an altered starch component as compared to starch from wild type wheat grain or flour. In another embodiment, the wheat grain or flour comprises starch with a percentage of amylose selected from the group consisting of: 25-30%, 30-35%, 35-40%, 45-50%, 50-55%, 55-60%, 60-65%, 65-70%, 70-75%, 75-80%, 80-85%, 85-90%, 90-95%, and greater than 95% as compared to wild type grain or flour.

Food Products

In one embodiment, the invention is directed to a flour or other product produced from the grain or flour discussed above. In another embodiments, the flour, the coarse fraction or purified starch may be a component of a food product.

The food product includes but is not limited to a bagel, a biscuit, a bread, a bun, a croissant, a dumpling, an English muffin, a muffin, a pita bread, a quickbread, a refrigerated/frozen dough products, dough, baked beans, a burrito, chili, a taco, a tamale, a tortilla, a pot pie, a ready to eat cereal, a ready to eat meal, stuffing, a microwaveable meal, a brownie, a cake, a cheesecake, a coffee cake, a cookie, a dessert, a pastry, a sweet roll, a candy bar, a pie crust, pie filling, baby food, a baking mix, a batter, a breading, a gravy mix, a meat extender, a meat substitute, a seasoning mix, a soup mix, a gravy, a roux, a salad dressing, a soup, sour cream, a noodle, a pasta, ramen noodles, chow mein noodles, lo mein noodles, an ice cream inclusion, an ice cream bar, an ice cream cone, an ice cream sandwich, a cracker, a crouton, a doughnut, an egg roll, an extruded snack, a fruit and grain bar, a microwaveable snack product, a nutritional bar, a pancake, a par-baked bakery product, a pretzel, a pudding, a granola-based product, a snack chip, a snack food, a snack mix, a waffle, a pizza crust, animal food or pet food.

In one embodiment, the flour is a whole grain flour (ex.—an ultrafine-milled whole grain flour, such as an ultrafine-milled whole grain wheat flour). In one embodiment, the whole grain flour includes a refined flour constituent (ex.—refined wheat flour or refined flour) and a coarse fraction (ex.—an ultrafine-milled coarse fraction). Refined wheat flour may be flour which is prepared, for example, by grinding and bolting (sifting) cleaned wheat. The Food and Drug Administration (FDA) requires flour to meet certain particle size standards in order to be included in the category of refined wheat flour. The particle size of refined wheat flour is described as flour in which not less than 98% passes through a cloth having openings not larger than those of woven wire cloth designated "212 micrometers (U.S. Wire 70)."

In another embodiment, the coarse fraction includes at least one of: bran and germ. For instance, the germ is an embryonic plant found within the wheat kernel. The germ includes lipids, fiber, vitamins, protein, minerals and phytonutrients, such as flavonoids. The bran may include several cell layers and has a significant amount of lipids, fiber, vitamins, protein, minerals and phytonutrients, such as flavonoids.

For example, the coarse fraction or whole grain flour or refined flour of the present invention may be used in various amounts to replace refined or whole grain flour in baked goods, snack products, and food products. The whole grain flour (i.e.—ultrafine-milled whole grain flour) may also be marketed directly to consumers for use in their homemade baked products. In an exemplary embodiment, a granulation profile of the whole grain flour is such that 98% of particles by weight of the whole grain flour are less than 212 micrometers.

In another embodiment, the whole grain flour or coarse fraction or refined flour may be a component of a nutritional supplement. The nutritional supplement may be a product that is added to the diet containing one or more ingredients, typically including: vitamins, minerals, herbs, amino acids, enzymes, antioxidants, herbs, spices, probiotics, extracts, prebiotics and fiber.

In a further embodiment, the nutritional supplement may include any known nutritional ingredients that will aid in the overall health of an individual, examples include but are not limited to vitamins, minerals, other fiber components, fatty acids, antioxidants, amino acids, peptides, proteins, lutein, ribose, omega-3 fatty acids, and/or other nutritional ingredients. Because of the high nutritional content of the endosperm of the present invention, there may be many uses that confer numerous benefits to an individual, including, delivery of fiber and other essential nutrients, increased digestive function and health, weight management, blood sugar management, heart health, diabetes risk reduction, potential arthritis risk reduction, and overall health and wellness for an individual.

In still another embodiments, the whole grain flour or coarse fraction or refined flour may be a component of a dietary supplement. The Code of Federal Regulations defines a dietary supplement as a product that is intended to supplement the diet and contains one or more dietary ingredients including: vitamins, minerals, herbs, botanicals, amino acids, and other substances or their constituents; is intended to be taken by mouth as a pill, capsule, tablet, or liquid; and is labeled on the front panel as being a dietary supplement.

In yet another embodiment, the whole grain flour or coarse fraction or refined flour may be a fiber supplement or a component thereof. The fiber supplement may be delivered in, but is not limited to the following forms: instant beverage mixes, ready-to-drink beverages, nutritional bars, wafers, cookies, crackers, gel shots, capsules, chews, chewable tablets, and pills. One embodiment delivers the fiber supplement in the form of a flavored shake or malt type beverage.

In another embodiment, the whole grain flour or coarse fraction or refined flour may be included as a component of a digestive supplement. The whole grain flour or coarse fraction or refined flour may be a component of a digestive supplement alone or in combination with one or more prebiotic compounds and/or probiotic organisms. Prebiotic compounds are non-digestible food ingredients that may beneficially affect the host by selectively stimulating the growth and/or the activity of a limited number of microorganisms in the colon. Examples of prebiotic compounds within the scope of the invention, may include, but are not limited to: oligosaccharides and inulins.

Probiotics are microorganisms which, when administered in adequate amounts, confer a health benefit on the host. Probiotic organisms include, but are not limited to: *Lactobacillus, Bifidobacteria, Escherichia, Clostridium, Lactococcus, Streptococcus, Enterococcus*, and *Saccharomyces*.

In yet another embodiment, the whole grain flour or coarse fraction or refined flour may be included as a component of a functional food. The Institute of Food Technologists defines functional foods as, foods and food components that provide a health benefit beyond basic nutrition. This includes conventional foods, fortified, enriched, or enhanced foods, and dietary supplements. The whole grain flour and coarse fraction or refined flour include numerous vitamins and minerals, have high oxygen radical absorption capacities, and are high in fiber, making them ideally suited for use in/as a functional food.

In another embodiment, the whole grain flour or coarse fraction or refined flour may be used in medical foods. Medical food is defined as a food that is formulated to be consumed or administered entirely under the supervision of a physician and which is intended for the specific dietary management of a disease or condition for which distinctive nutritional requirements, based on recognized scientific principles, are established by medical evaluation. The nutrient contents and antioxidant capacities of the whole grain flour and coarse fraction or refined flour make them ideal for use in medical foods.

In yet another embodiment, the whole grain flour or coarse fraction or refined flour may also be used in pharmaceuticals. The whole grain flour and coarse fraction or refined flour are high in fiber and have a very fine granulation making them suitable for use as a carrier in pharmaceuticals.

In still another embodiment, delivery of the whole grain flour or coarse fraction or refined flour as a nutritional supplement, dietary supplement or digestive supplement is contemplated via delivery mechanisms where the whole grain flour or coarse fraction is the single ingredient or one of many nutritional ingredients. Examples of delivery mechanisms include but are not limited to: instant beverage mixes, ready-to-drink beverages, nutritional bars, wafers, cookies, crackers, gel shots, capsules, and chews.

In yet another embodiment, a milling process may be used to make a multi-wheat flour, or a multi-grain coarse fraction. In one embodiment, bran and germ from one type of wheat may be ground and blended with ground endosperm or whole grain wheat flour of another type of wheat. Alternatively bran and germ of one type of grain may be ground and blended with ground endosperm or whole grain flour of another type of grain.

In still another embodiment, bran and germ from a first type of wheat or grain may be blended with bran and germ from a second type of wheat or grain to produce a multi-grain coarse fraction. It is contemplated that the invention encompasses mixing any combination of one or more of bran, germ, endosperm, and whole grain flour of one or more grains. This multi-grain, multi-wheat approach may be used to make custom flour and capitalize on the qualities and nutritional contents of multiple types of grains or wheats to make one flour.

The whole grain flour of the invention may be produced via a variety of milling processes. One exemplary process involves grinding grain in a single stream without separating endosperm, bran, and germ of the grain into separate streams. Clean and tempered grain is conveyed to a first passage grinder, such as a hammermill, roller mill, pin mill, impact mill, disc mill, air attrition mill, gap mill, or the like.

After grinding, the grain is discharged and conveyed to a sifter. Any sifter known in the art for sifting a ground particle may be used. Material passing through the screen of the sifter is the whole grain flour of the invention and requires no further processing. Material that remains on the screen is referred to as a second fraction. The second fraction requires additional particle reduction. Thus, this second fraction may be conveyed to a second passage grinder.

After grinding, the second fraction may be conveyed to a second sifter. Material passing through the screen of the second sifter is the whole grain flour. The material that remains on the screen is referred to as the fourth fraction and requires further processing to reduce the particle size. The fourth fraction on the screen of the second sifter is conveyed back into either the first passage grinder or the second passage grinder for further processing via a feedback loop.

It is contemplated that the whole grain flour, coarse fraction, purified starch and/or grain products of the invention may be produced by a number of milling processes known in the art.

Plant Breeding

In another embodiment, this invention is directed to methods for plant breeding using wheat plants and plant parts with one or more non-transgenic mutations in the SBEII gene.

One such embodiment is the method of crossing wheat variety with one or more non-transgenic mutations in the SBEII gene with another variety of wheat to form a first generation population of F1 plants. The population of first generation F1 plants produced by this method is also an embodiment of the invention. This first generation population of F1 plants will comprise an essentially complete set of the alleles of wheat variety with one or more non-transgenic mutations in the SBEII gene. One of ordinary skill in the art can utilize either breeder books or molecular methods to identify a particular F1 plant produced using wheat variety with one or more non-transgenic mutations in the SBEII gene, and any such individual plant is also encompassed by this invention. These embodiments also cover use of transgenic or backcross conversions of wheat varieties with one or more mutations in the SBEII gene to produce first generation F1 plants.

In another embodiment, the invention relates to a method of developing a progeny wheat plant. A method of developing a progeny wheat plant comprises crossing a wheat variety with one or more non-transgenic mutations in the SBEII gene with a second wheat plant and performing a breeding method. A specific method for producing a line derived from wheat variety with one or more non-transgenic mutations in the SBEII gene is as follows.

One of ordinary skill in the art would cross wheat variety with one or more non-transgenic mutations in the SBEII gene with another variety of wheat, such as an elite variety. The F1 seed derived from this cross would be grown to form a homogeneous population. The F1 seed would contain one set of the alleles from wheat variety with one or more non-transgenic mutations in the SBEII gene and one set of the alleles from the other wheat variety.

The F1 genome would be made-up of 50% wheat variety with one or more non-transgenic mutations in the SBEII gene and 50% of the other elite variety. The F1 seed would be grown to form F2 seed. The F1 seed could be allowed to self, or bred with another wheat cultivar.

On average the F2 seed would have derived 50% of its alleles from wheat variety with one or more non-transgenic mutations in the SBEII gene and 50% from the other wheat variety, but various individual plants from the population would have a much greater percentage of their alleles derived from wheat variety with one or more non-transgenic mutations in the SBEII gene (Wang J. and R. Bernardo, 2000, Crop Sci. 40:659-665 and Bernardo, R. and A. L. Kahler, 2001, Theor. Appl. Genet. 102:986-992).

The F2 seed would be grown and selection of plants would be made based on visual observation and/or measurement of traits and/or marker assisted selection. The wheat variety with one or more non-transgenic mutations in the SBEII gene-derived progeny that exhibit one or more of the desired wheat variety with one or more non-transgenic mutations in the SBEII gene-derived traits would be selected and each plant would be harvested separately. This F3 seed from each plant would be grown in individual rows and allowed to self. Then selected rows or plants from the rows would be harvested and threshed individually. The selections would again be based on visual observation and/or measurements for desirable traits of the plants, such as one or more of the desirable wheat variety with one or more non-transgenic mutations in the SBEII gene-derived traits.

The process of growing and selection would be repeated any number of times until a homozygous wheat variety with one or more non-transgenic mutations in the SBEII gene-derived wheat plant is obtained. The homozygous wheat variety with one or more non-transgenic mutations in the SBEII gene-derived wheat plant would contain desirable traits derived from wheat variety with one or more non-transgenic mutations in the SBEII gene, some of which may not have been expressed by the other original wheat variety to which wheat variety with one or more non-transgenic mutations in the SBEII gene was crossed and some of which may have been expressed by both wheat varieties but now would be at a level equal to or greater than the level expressed in wheat variety with one or more non-transgenic mutations in the SBEII gene.

The breeding process, of crossing, selfing, and selection may be repeated to produce another population of wheat variety with one or more non-transgenic mutations in the SBEII gene-derived wheat plants with, on average, 25% of their genes derived from wheat variety with one or more non-transgenic mutations in the SBEII gene, but various individual plants from the population would have a much greater percentage of their alleles derived from wheat variety with one or more non-transgenic mutations in the SBEII gene. Another embodiment of the invention is a homozygous wheat variety with one or more non-transgenic mutations in the SBEII gene-derived wheat plant that has received wheat variety with one or more non-transgenic mutations in the SBEII gene-derived traits.

The invention is further described by the following paragraphs.

1. A polynucleotide encoding an SBEIIa polypeptide comprising a tryptophan to a stop mutation at an amino acid corresponding to amino acid position 436 of SEQ ID NO: 2.

2. The polynucleotide of paragraph 1, wherein the SBEIIa polypeptide further comprises an amino acid sequence having at least 95% identity or similarity to SEQ ID NO: 2.

3. The polynucleotide of any of paragraphs 1-2, wherein the SBEIIa polypeptide further comprises an amino acid sequence having at least 97% identity or similarity to SEQ ID NO: 2.

4. The polynucleotide of any of paragraphs 1-3, wherein the SBEIIa polypeptide further comprises an amino acid sequence having at least 99% identity or similarity to SEQ ID NO: 2.

5. The polynucleotide of any of paragraphs 1-4 comprising a guanine to adenine mutation at a nucleotide position corresponding to nucleotide position 5267 of SEQ ID NO: 1.

6. The polynucleotide of any of paragraphs 1-5 further comprising at least 95% identity or similarity to SEQ ID NO: 1.

7. The polynucleotide of any of paragraphs 1-6 further comprising at least 97% identity or similarity to SEQ ID NO: 1.

8. The polynucleotide o any of paragraphs 1-7 further comprising at least 99% identity or similarity to SEQ ID NO: 1.

9. A polypeptide comprising an amino acid sequence having at least 95% identity or similarity to SEQ ID NO:2, wherein the polypeptide further comprises a tryptophan to a stop mutation at amino acid position 436 of SEQ ID NO: 2.

10. The polypeptide of paragraph 9 further comprising an amino acid sequence having at least 97% sequence identity or similarity to SEQ ID NO:2.

11. The polypeptide of any of paragraphs 9-10 further comprising an amino acid sequence having at least 99% sequence identity or similarity to SEQ ID NO:2.

12. The polypeptide of any of paragraphs 9-11 further comprising an amino acid sequence of SEQ ID NO:2 with a tryptophan to a stop mutation at amino acid position 436 or a fragment thereof having starch branching enzyme activity.

13. The polypeptide of any of paragraphs 1-12 further comprising an amino acid sequence of SEQ ID NO:2 with a tryptophan to a stop mutation at amino acid position 436.

14. A polynucleotide encoding an SBEIIa polypeptide comprising a tryptophan to a stop mutation at an amino acid corresponding to amino acid position 436 of SEQ ID NO: 4.

15. The polynucleotide of paragraph 14, wherein the SBEIIa polypeptide further comprises an amino acid sequence having at least 95% identity or similarity to SEQ ID NO: 4.

16. The polynucleotide of any of paragraphs 14-15, wherein the SBEIIa polypeptide further comprises an amino acid sequence having at least 97% identity or similarity to SEQ ID NO: 4.

17. The polynucleotide of any of paragraphs 14-16, wherein the SBEIIa polypeptide further comprises an amino acid sequence having at least 99% identity or similarity to SEQ ID NO: 4.

18. The polynucleotide of any of paragraphs 14-17 comprising a guanine to adenine mutation at a nucleotide position corresponding to nucleotide position 5038 of SEQ ID NO: 3.

19. The polynucleotide of any of paragraphs 14-18 further comprising at least 95% identity or similarity to SEQ ID NO: 3.

20. The polynucleotide of any of paragraphs 14-19 further comprising at least 97% identity or similarity to SEQ ID NO: 3.

21. The polynucleotide of any of paragraphs 14-20 further comprising at least 99% identity or similarity to SEQ ID NO: 3.

22. A polypeptide comprising an amino acid sequence having at least 95% identity or similarity to SEQ ID NO:4, wherein the polypeptide further comprises a tryptophan to a stop mutation at amino acid position 436 of SEQ ID NO: 4.

23. The polypeptide of paragraph 22 further comprising an amino acid sequence having at least 97% sequence identity or similarity to SEQ ID NO:4.

24. The polypeptide of any of paragraphs 22-23 further comprising an amino acid sequence having at least 99% sequence identity or similarity to SEQ ID NO:4.

25. The polypeptide of any of paragraphs 22-24 comprising an amino acid sequence of SEQ ID NO:4 with a tryptophan to a stop mutation at amino acid position 436 or a fragment thereof having starch branching enzyme activity.

26. The polypeptide of any of paragraphs 22-25 comprising an amino acid sequence of SEQ ID NO:4 with a tryptophan to a stop mutation at amino acid position 436.

27. A polynucleotide encoding an SBEIIa polypeptide comprising a tryptophan to a stop mutation at an amino acid corresponding to amino acid position 432 of SEQ ID NO: 6.

28. The polynucleotide of paragraph 27, wherein the SBEIIa polypeptide further comprises an amino acid sequence having at least 95% identity or similarity to SEQ ID NO: 6.

29. The polynucleotide of any of paragraphs 27-28, wherein the SBEIIa polypeptide further comprises an amino acid sequence having at least 97% identity or similarity to SEQ ID NO: 6.

30. The polynucleotide of any of paragraphs 27-29, wherein the SBEIIa polypeptide further comprises an amino acid sequence having at least 99% identity or similarity to SEQ ID NO: 6.

31. The polynucleotide of any of paragraphs 27-30 comprising a guanine to adenine mutation at a nucleotide position corresponding to nucleotide position 6305 of SEQ ID NO: 5.

32. The polynucleotide of any of paragraphs 27-31 further comprising at least 95% identity or similarity to SEQ ID NO: 5.

33. The polynucleotide of any of paragraphs 27-32 further comprising at least 97% identity or similarity to SEQ ID NO: 5.

34. The polynucleotide of any of paragraphs 27-33 further comprising at least 99% identity or similarity to SEQ ID NO: 5.

35. A polypeptide comprising an amino acid sequence having at least 95% identity or similarity to SEQ ID NO:6, wherein the polypeptide further comprises a tryptophan to a stop mutation at amino acid position 432 of SEQ ID NO: 6.

36. The polypeptide of paragraph 35 further comprising an amino acid sequence having at least 97% sequence identity or similarity to SEQ ID NO:6.

37. The polypeptide of any of paragraphs 35-36 further comprising an amino acid sequence having at least 99% sequence identity or similarity to SEQ ID NO:6.

38. The polypeptide of any of paragraphs 35-37 comprising an amino acid sequence of SEQ ID NO:6 with a tryptophan to a stop mutation at amino acid position 432 or a fragment thereof having starch branching enzyme activity.

39. The polypeptide of any of paragraphs 35-38 comprising an amino acid sequence of SEQ ID NO:6 with a tryptophan to a stop mutation at amino acid position 432.

40. A polynucleotide encoding an SBEIIa polypeptide comprising a tryptophan to a stop mutation at an amino acid corresponding to amino acid position 446 of SEQ ID NO: 4.

41. The polynucleotide of paragraph 40, wherein the SBEIIa polypeptide further comprises an amino acid sequence having at least 95% identity or similarity to SEQ ID NO: 4.

42. The polynucleotide of any of paragraphs 40-41, wherein the SBEIIa polypeptide further comprises an amino acid sequence having at least 97% identity or similarity to SEQ ID NO: 4.

43. The polynucleotide of any of paragraphs 40-42, wherein the SBEIIa polypeptide further comprises an amino acid sequence having at least 99% identity or similarity to SEQ ID NO: 4.

44. The polynucleotide of any of paragraphs 40-43 comprising a guanine to adenine mutation at a nucleotide position corresponding to nucleotide position 5069 of SEQ ID NO: 3.

45. The polynucleotide of any of paragraphs 40-44 further comprising at least 95% identity or similarity to SEQ ID NO: 3.

46. The polynucleotide of any of paragraphs 40-45 further comprising at least 97% identity or similarity to SEQ ID NO: 3.

47. The polynucleotide of any of paragraphs 40-46 further comprising at least 99% identity or similarity to SEQ ID NO: 3.

48. A polypeptide comprising an amino acid sequence having at least 95% identity or similarity to SEQ ID NO:4, wherein the polypeptide further comprises a tryptophan to a stop mutation at amino acid position 446 of SEQ ID NO: 4.

49. The polypeptide of paragraph 48 further comprising an amino acid sequence having at least 97% sequence identity or similarity to SEQ ID NO:4.

50. The polypeptide of paragraphs 48-49 further comprising an amino acid sequence having at least 99% sequence identity or similarity to SEQ ID NO:4.

51. The polypeptide of any of paragraphs 48-50 comprising an amino acid sequence of SEQ ID NO:4 with a tryptophan to a stop mutation at amino acid position 446 or a fragment thereof having starch branching enzyme activity.

52. The polypeptide of any of paragraphs 48-51 comprising an amino acid sequence of SEQ ID NO:4 with a tryptophan to a stop mutation at amino acid position 446.

53. An SBEIIa polynucleotide comprising a guanine to adenine mutation at a nucleotide position corresponding to nucleotide position 5073 of SEQ ID NO: 3.

54. The polynucleotide of paragraph 53 further comprising at least 95% identity or similarity to SEQ ID NO: 3.

55. The polynucleotide of any of paragraph 53-54 further comprising at least 97% identity or similarity to SEQ ID NO: 3.

56. The polynucleotide of any of paragraphs 53-55 further comprising at least 99% identity or similarity to SEQ ID NO: 3.

57. A polynucleotide encoding an SBEIIa polypeptide comprising a glycine to a glutamate mutation at an amino acid corresponding to amino acid position 467 of SEQ ID NO: 4.

58. The polynucleotide of paragraph 57, wherein the SBEIIa polypeptide further comprises an amino acid sequence having at least 95% identity or similarity to SEQ ID NO: 4.

59. The polynucleotide of any of paragraphs 57-58, wherein the SBEIIa polypeptide further comprises an amino acid sequence having at least 97% identity or similarity to SEQ ID NO: 4.

60. The polynucleotide of any of paragraphs 57-59, wherein the SBEIIa polypeptide further comprises an amino acid sequence having at least 99% identity or similarity to SEQ ID NO: 4.

61. The polynucleotide of any of paragraphs 57-60 comprising a guanine to adenine mutation at a nucleotide position corresponding to nucleotide position 5219 of SEQ ID NO: 3.

62. The polynucleotide of any of paragraphs 57-61 further comprising at least 95% identity or similarity to SEQ ID NO: 3.

63. The polynucleotide of any of paragraphs 57-62 further comprising at least 97% identity or similarity to SEQ ID NO: 3.

64. The polynucleotide of any of paragraphs 57-63 further comprising at least 99% identity or similarity to SEQ ID NO: 3.

65. A polypeptide comprising an amino acid sequence having at least 95% identity or similarity to SEQ ID NO:4, wherein the polypeptide further comprises a glycine to a glutamate mutation at amino acid position 467 of SEQ ID NO: 4.

66. The polypeptide of paragraph 65 further comprising an amino acid sequence having at least 97% sequence identity or similarity to SEQ ID NO:4.

67. The polypeptide of any of paragraphs 65-66 further comprising an amino acid sequence having at least 99% sequence identity or similarity to SEQ ID NO:4.

68. The polypeptide of any of paragraphs 65-67 comprising an amino acid sequence of SEQ ID NO:4 with a glycine to a glutamate mutation at amino acid position 467 or a fragment thereof having starch branching enzyme activity.

69. The polypeptide of any of paragraphs 65-68 comprising an amino acid sequence of SEQ ID NO:4 with a glycine to a glutamate mutation at amino acid position 467.

70. A polynucleotide encoding an SBEIIa polypeptide comprising a tryptophan to a stop mutation at an amino acid corresponding to amino acid position 442 of SEQ ID NO: 6.

71. The polynucleotide of paragraph 70, wherein the SBEIIa polypeptide further comprises an amino acid sequence having at least 95% identity or similarity to SEQ ID NO: 6.

72. The polynucleotide of any of paragraphs 70-71, wherein the SBEIIa polypeptide further comprises an amino acid sequence having at least 97% identity or similarity to SEQ ID NO: 6.

73. The polynucleotide of any of paragraphs 70-72, wherein the SBEIIa polypeptide further comprises an amino acid sequence having at least 99% identity or similarity to SEQ ID NO: 6.

74. The polynucleotide of any of paragraphs 70-73 comprising a guanine to adenine mutation at a nucleotide position corresponding to nucleotide position 6335 of SEQ ID NO: 5.

75. The polynucleotide of any of paragraphs 70-74 further comprising at least 95% identity or similarity to SEQ ID NO: 5.

76. The polynucleotide of any of paragraphs 70-75 further comprising at least 97% identity or similarity to SEQ ID NO: 5.

77. The polynucleotide of any of paragraphs 70-76 further comprising at least 99% identity or similarity to SEQ ID NO: 5.

78. A polypeptide comprising an amino acid sequence having at least 95% identity or similarity to SEQ ID NO:6, wherein the polypeptide further comprises a tryptophan to a stop mutation at amino acid position 442 of SEQ ID NO: 6.

79. The polypeptide of paragraph 78 further comprising an amino acid sequence having at least 97% sequence identity or similarity to SEQ ID NO:6.

80. The polypeptide of any of paragraphs 78-79 further comprising an amino acid sequence having at least 99% sequence identity or similarity to SEQ ID NO:6.

81. The polypeptide of any of paragraphs 78-80 further comprising an amino acid sequence of SEQ ID NO:6 with a tryptophan to a stop mutation at amino acid position 442 or a fragment thereof having starch branching enzyme activity.

82. The polypeptide of any of paragraphs 78-81 comprising an amino acid sequence of SEQ ID NO:6 with a tryptophan to a stop mutation at amino acid position 442.

83. A polynucleotide encoding an SBEIIb polypeptide comprising a tryptophan to a stop mutation at an amino acid corresponding to amino acid position 285 of SEQ ID NO: 8.

84. The polynucleotide of paragraph 83, wherein the SBEIIb polypeptide further comprises an amino acid sequence having at least 95% identity or similarity to SEQ ID NO: 8.

85. The polynucleotide of any of paragraphs 83-84, wherein the SBEIIb polypeptide further comprises an amino acid sequence having at least 97% identity or similarity to SEQ ID NO: 8.

86. The polynucleotide of any of paragraphs 83-85, wherein the SBEIIb polypeptide further comprises an amino acid sequence having at least 99% identity or similarity to SEQ ID NO: 8.

87. The polynucleotide of any of paragraphs 83-86 comprising a guanine to adenine mutation at a nucleotide position corresponding to nucleotide position 2282 of SEQ ID NO: 7.

88. The polynucleotide of any of paragraphs 83-87 further comprising at least 95% identity or similarity to SEQ ID NO: 7.

89. The polynucleotide of any of paragraphs 83-88 further comprising at least 97% identity or similarity to SEQ ID NO: 7.

90. The polynucleotide of any of paragraphs 83-89 further comprising at least 99% identity or similarity to SEQ ID NO: 7.

91. A polypeptide comprising an amino acid sequence having at least 95% identity or similarity to SEQ ID NO:8, wherein the polypeptide further comprises a tryptophan to a stop mutation at amino acid position 285 of SEQ ID NO: 8.

92. The polypeptide of paragraph 91 further comprising an amino acid sequence having at least 97% sequence identity or similarity to SEQ ID NO:8.

93. The polypeptide of any of paragraphs 91-92 further comprising an amino acid sequence having at least 99% sequence identity or similarity to SEQ ID NO:8.

94. The polypeptide of any of paragraphs 91-93 further comprising an amino acid sequence of SEQ ID NO:8 with a tryptophan to a stop mutation at amino acid position 285 or a fragment thereof having starch branching enzyme activity.

95. The polypeptide of any of paragraphs 91-94 comprising an amino acid sequence of SEQ ID NO:8 with a tryptophan to a stop mutation at amino acid position 285.

96. A wheat plant comprising a polynucleotide of any of paragraphs 1-8, 14-21, 27-34, 40-47, 53-56, 57-64, 70-77, and 83-90.

97. A wheat plant comprising at least two non-transgenic mutations in an SBEII gene, wherein at least one mutation is in the SBEIIa gene as recited in any of paragraphs 1-8, 14-21, 27-34, 40-47, 53-56, 57-64, and 70-77.

98. The wheat plant of any of paragraphs 96-97, wherein a second non-transgenic mutation is in the SBEIIb gene. The SBEIIb mutations may be as recited in paragraphs 83-90.

99. The wheat plant of any of paragraphs 96-98, wherein the first and second mutations are in the SBEIIa gene.

100. The wheat plant of any of paragraphs 96-99, wherein the first and second mutations are in the same genome.

101. The wheat plant of any of paragraphs 96-100, wherein the first and second mutations are in different genomes.

102. The wheat plant of any of paragraphs 96-101, further comprising at least three non-transgenic mutations in the SBEII gene.

103. The wheat plant of any of paragraphs 96-102, wherein two mutations are in the same genome.

104. The wheat plant of any of paragraphs 96-103, wherein three mutations are in different genomes.

105. The wheat plant of any of paragraphs 96-104, wherein the three mutations are in each of the A genome, B genome and D genome. Any number of mutations are possible including 1, 2, 3, 4, 5, 6, 7, 8, 9, 10, and greater than 10 mutations in the SBEIIa gene and including 1, 2, 3, 4, 5, 6, 7, 8, 9, 10, and greater than 10 mutations in the SBEIIb gene.

106. A wheat plant comprising at least two polynucleotides as recited in any of paragraphs 1-8, 14-21, 27-34, 40-47, 53-56, 57-64, 70-77, and 83-90

107. A wheat plant comprising a polypeptide of any of paragraphs 9-13, 22-26, 35-39, 48-52, 65-69, 78-82, and 91-95.

108. The wheat plant of any of paragraphs 96-107, wherein the wheat is diploid, tetraploid or hexaploid.

109. A hexaploid wheat plant comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5308 of SEQ ID NO: 3; and wherein the mutation in the SBEIIa gene of the D genome corresponds to a guanine to adenine mutation at nucleotide position 6305 of SEQ ID NO: 5.

110. A hexaploid wheat plant comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5069 of SEQ ID NO: 3; and wherein the mutation in the SBEIIa gene of the D genome corresponds to a guanine to adenine mutation at nucleotide position 6335 of SEQ ID NO: 5.

111. A hexaploid wheat plant comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5193 of SEQ ID NO: 3; and wherein the mutation in the SBEIIa gene of the D genome corresponds to a guanine to adenine mutation at nucleotide position 6305 of SEQ ID NO: 5.

112. A wheat plant comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5073 of SEQ ID NO: 3.

113. A wheat plant comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5219 of SEQ ID NO: 3.

114. A wheat plant comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5033 of SEQ ID NO: 3.

115. A wheat seed comprising a polynucleotide of any of paragraphs 1-8, 14-21, 27-34, 40-47, 53-56, 57-64, 70-77, and 83-90.

116. A wheat seed comprising at least two non-transgenic mutations in an SBEII gene, wherein at least one mutation is in the SBEIIa gene as recited in any of paragraphs 1-8, 14-21, 27-34, 40-47, 53-56, 57-64, 70-77, and 83-90.

117. The wheat seed of any of paragraphs 115-115, wherein a second non-transgenic mutation is in the SBEIIb gene.

118. The wheat seed of any of paragraphs 115-117, wherein the first and second mutations are in the SBEIIa gene.

119. The wheat seed of any of paragraphs 115-118, wherein the first and second mutations are in the same genome.

120. The wheat seed of any of paragraphs 115-119, wherein the first and second mutations are in different genomes.

121. The wheat seed of any of paragraphs 115-120 further comprising at least three non-transgenic mutations in the SBEII gene.

122. The wheat seed of any of paragraphs 115-121, wherein three mutations are in the same genome.

123. The wheat seed of any of paragraphs 115-122, wherein three mutations are in different genomes.

124. The wheat seed of any of paragraphs 115-123, wherein the three mutations are in each of the A genome, B genome and D genome.

125. A wheat seed comprising at least two polynucleotides as recited in any of paragraphs 1-8, 14-21, 27-34, 40-47, 53-56, 57-64, 70-77, and 83-90.

126. A wheat seed comprising a polypeptide of any of paragraphs 9-13, 22-26, 35-39, 48-52, 65-69, 78-82, and 91-95.

127. The wheat seed of any of paragraphs 115-126, wherein the wheat is diploid, tetraploid or hexaploid.

128. A hexaploid wheat seed comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5308 of SEQ ID NO: 3; and wherein the mutation in the SBEIIa gene of the D genome corresponds to a guanine to adenine mutation at nucleotide position 6305 of SEQ ID NO: 5.

129. A hexaploid wheat seed comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5069 of SEQ ID NO: 3; and wherein the mutation in the SBEIIa gene of the D genome corresponds to a guanine to adenine mutation at nucleotide position 6335 of SEQ ID NO: 5.

130. A hexaploid wheat seed comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5193 of SEQ ID NO: 3; and wherein the mutation in the SBEIIa gene of the D genome corresponds to a guanine to adenine mutation at nucleotide position 6305 of SEQ ID NO: 5.

131. A wheat seed comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5073 of SEQ ID NO: 3.

132. A wheat seed comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5219 of SEQ ID NO: 3.

133. A wheat seed comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5033 of SEQ ID NO: 3.

134. Wheat grain comprising a polynucleotide of any of paragraphs 1-8, 14-21, 27-34, 40-47, 53-56, 57-64, 70-77, and 83-90.

135. Wheat grain comprising at least two non-transgenic mutations in an SBEII gene, wherein one mutation is in the SBEIIa gene as recited in any of paragraphs 1-8, 14-21, 27-34, 40-47, 53-56, 57-64, 70-77, and 83-90.

136. The wheat grain of any of paragraphs 134-135, wherein a second non-transgenic mutation is in the SBEIIb gene.

137. The wheat grain of any of paragraphs 134-136, wherein the first and second mutations are in the SBEIIa gene.

138. The wheat grain of any of paragraphs 134-137, wherein the first and second mutations are in the same genome.

139. The wheat grain of any of paragraphs 134-138, wherein the first and second mutations are in different genomes.

140. The wheat grain of any of paragraphs 134-139, further comprising at least three non-transgenic mutations in the SBEII gene.

141. The wheat grain of any of paragraphs 134-140, wherein the three mutations are in the same genome.

142. The wheat grain of any of paragraphs 134-141, wherein the three mutations are in different genomes.

143. The wheat grain of any of paragraphs 134-142, wherein the three mutations are in each of the A genome, B genome and D genome.

144. Wheat grain comprising at least two polynucleotides as recited in any of paragraphs 1-8, 14-21, 27-34, 40-47, 53-56, 57-64, 70-77, and 83-90.

145. Wheat grain comprising a polypeptide of any of paragraphs 9-13, 22-26, 35-39, 48-52, 65-69, 78-82, and 91-95.

146. Wheat grain of any of paragraphs 134-145, wherein the wheat is diploid, tetraploid or hexaploid.

147. A hexaploid wheat grain comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5308 of SEQ ID NO: 3; and wherein the mutation in the SBEIIa gene of the D genome corresponds to a guanine to adenine mutation at nucleotide position 6305 of SEQ ID NO: 5.

148. A hexaploid wheat grain comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5069 of SEQ ID NO: 3; and wherein the mutation in the SBEIIa gene of the D genome corresponds to a guanine to adenine mutation at nucleotide position 6335 of SEQ ID NO: 5.

149. A hexaploid wheat grain comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5193 of SEQ ID NO: 3; and wherein the mutation in the SBEIIa gene of the D genome corresponds to a guanine to adenine mutation at nucleotide position 6305 of SEQ ID NO: 5.

150. A wheat grain comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5073 of SEQ ID NO: 3.

151. A wheat grain comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5219 of SEQ ID NO: 3.

152. A wheat grain comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5033 of SEQ ID NO: 3.

153. Wheat flour comprising a polynucleotide of any of paragraphs 1-8, 14-21, 27-34, 40-47, 53-56, 57-64, 70-77, and 83-90.

154. Wheat flour comprising at least two non-transgenic mutations in an SBEII gene, wherein one mutation is in the SBEIIa gene as recited in any of paragraphs 1-8, 14-21, 27-34, 40-47, 53-56, 57-64, 70-77, and 83-90.

155. The wheat flour of any of paragraphs 153-154, wherein a second non-transgenic mutation is in the SBEIIb gene.

156. The wheat flour of any of paragraphs 153-155, wherein the first and second mutations are in the SBEIIa gene.

157. The wheat flour of any of paragraphs 153-156, wherein the first and second mutations are in the same genome.

158. The wheat flour of any of paragraphs 153-157, wherein the first and second mutations are in different genomes.

159. The wheat flour of any of paragraphs 153-158, further comprising at least three non-transgenic mutations in the SBEII gene.

160. The wheat flour of any of paragraphs 153-159, wherein the three mutations are in the same genome.

161. The wheat flour of any of paragraphs 153-160, wherein the three mutations are in different genomes.

162. The wheat flour of any of paragraphs 153-161, wherein the three mutations are in each of the A genome, B genome and D genome.

163. Wheat flour comprising at least two polynucleotides as recited in any of paragraphs 1-8, 14-21, 27-34, 40-47, 53-56, 57-64, 70-77, and 83-90.

164. Wheat flour comprising a polypeptide of any of paragraphs 9-13, 22-26, 35-39, 48-52, 65-69, 78-82, and 91-95.

165. Wheat flour of any of paragraphs 153-164, wherein the wheat is diploid, tetraploid or hexaploid.

166. A hexaploid wheat flour comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5308 of SEQ ID NO: 3; and wherein the mutation in the SBEIIa gene of the D genome corresponds to a guanine to adenine mutation at nucleotide position 6305 of SEQ ID NO: 5.

167. A hexaploid wheat flour comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5069 of SEQ ID NO: 3; and wherein the mutation in the SBEIIa gene of the D genome corresponds to a guanine to adenine mutation at nucleotide position 6335 of SEQ ID NO: 5.

168. A hexaploid wheat flour comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5193 of SEQ ID NO: 3; and wherein the mutation in the SBEIIa gene of the D genome corresponds to a guanine to adenine mutation at nucleotide position 6305 of SEQ ID NO: 5.

169. A wheat flour comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5073 of SEQ ID NO: 3.

170. A wheat flour comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5219 of SEQ ID NO: 3.

171. A wheat flour comprising at least one mutation in each SBEIIa gene, wherein the mutation in the SBEIIa gene of the A genome corresponds to a guanine to adenine mutation at nucleotide position 5267 of SEQ ID NO: 1, wherein the mutation in the SBEIIa gene of the B genome corresponds to a guanine to adenine mutation at nucleotide position 5033 of SEQ ID NO: 3.

172. A food product comprising the wheat grain of any of paragraphs 134-152.

173. A food product comprising the wheat flour of any of paragraphs 153-171.

174. Use of a polynucleotide according to any of paragraphs 1-8, 14-21, 27-34, 40-47, 53-56, 57-64, 70-77, and 83-90 for the production of wheat having increased amylose levels compared to wild type wheat, wherein said polynucleotide contributes to the increased amylose levels.

175. Use of a polynucleotide according to any of paragraphs 1-8, 14-21, 27-34, 40-47, 53-56, 57-64, 70-77, and 83-90 for the selection of wheat having increased amylose levels compared to wild type wheat, wherein genomic DNA is isolated from the wheat and a segment of said SBEII gene is amplified and the presence of said gene is detected.

176. Use of a polypeptide according to any of paragraphs 9-13, 22-26, 35-39, 48-52, 65-69, 78-82, and 91-95 for the production of wheat having increased amylose levels compared to wild type wheat, wherein said polynucleotide contributes to the increased amylose levels.

177. Use of a polypeptide according to any of paragraphs 9-13, 22-26, 35-39, 48-52, 65-69, 78-82, and 91-95 for the selection of wheat having increased amylose levels compared to wild type wheat, wherein genomic DNA is isolated from the wheat and a segment of said SBEII gene is amplified and the presence of said gene is detected.

EXAMPLE 1

Mutagenesis

In accordance with one exemplary embodiment of the present invention, wheat seeds of the hexaploid cultivar (*Triticum aestivum*) Express and of the tetraploid cultivar (*Triticum turgidum*, Durum) Kronos were vacuum infiltrated in $H_2O$ (approximately 1,000 seeds/100 ml $H_2O$ for approximately 4 minutes). The seeds were then placed on a shaker (45 rpm) in a fume hood at room temperature. The mutagen ethyl methanesulfonate (EMS) was added to the imbibing seeds to final concentrations ranging from about 0.75% to about 1.2% (v/v). Following an 18-hour incubation period, the EMS solution was replaced 4 times with fresh $H_2O$. The seeds were then rinsed under running water for about 4-8 hours. Finally, the mutagenized seeds were planted (96/tray) in potting soil and allowed to germinate indoors. Plants that were four to six weeks old were transferred to the field to grow to fully mature M1 plants. The mature M1 plants were allowed to self-pollinate and then seeds from the M1 plant were collected and planted to produce M2 plants.

DNA Preparation

DNA from the M2 plants produced in accordance with the above description was extracted and prepared in order to identify which M2 plants carried a mutation at one or more of their SBEII loci. The M2 plant DNA was prepared using the methods and reagents contained in the Qiagen® (Valencia, Calif.) DNeasy® 96 Plant Kit. Approximately 50 mg of frozen plant sample was placed in a sample tube with a tungsten bead, frozen in liquid nitrogen and ground 2 times for 1 minute each at 20 Hz using the Retsch® Mixer Mill MM 300. Next, 400 µl of solution AP1 [Buffer AP1, solution DX and RNAse (100 mg/ml)] at 80° C. was added to the sample. The tube was sealed and shaken for 15 seconds. Following the addition of 130 µl Buffer AP2, the tube was shaken for 15 seconds. The samples were placed in a freezer at minus 20° C. for at least 1 hour. The samples were then centrifuged for 20 minutes at 5,600×g. A 400 µl aliquot of supernatant was transferred to another sample tube. Following the addition of 600 µl of Buffer AP3/E, this sample tube was capped and shaken for 15 seconds. A filter plate was placed on a square well block and 1 ml of the sample solution was applied to each well and the plate was sealed. The plate and block were centrifuged for 4 minutes at 5,600×g. Next, 800 µl of Buffer AW was added to each well of the filter plate, sealed and spun for 15 minutes at 5,600×g in the square well block. The filter plate was then placed on a new set of sample tubes and 80 µl of Buffer AE was applied to the filter. It was capped and incubated at room temperature for 1 minute and then spun for 2 minutes at 5600×g. This step was repeated with an additional 80 µl Buffer AE. The filter plate was removed and the tubes containing the pooled filtrates were capped. The individual samples were then normalized to a DNA concentration of 5 to 10 ng/µl.

Tilling

The M2 DNA was pooled into groups of two individual plants. The DNA concentration for each individual within the pool was approximately 0.8 ng/µl with a final concentration of 1.6 ng/µl for the entire pool. Then, 5 µl of the pooled DNA samples (or 8 ng wheat DNA) was arrayed on microtiter plates and subjected to gene-specific PCR.

PCR amplification was performed in 15 µl volumes containing 2.5 ng pooled DNA, 0.75× ExTaq buffer (Panvera®, Madison, Wis.), 2.6 mM $MgCl_2$, 0.3 mM dNTPs, 0.3 µM primers, and 0.05U Ex-Taq (Panvera®) DNA polymerase. PCR amplification was performed using an MJ Research® thermal cycler as follows: 95° C. for 2 minutes; 8 cycles of "touchdown PCR" (94° C. for 20 second, followed by annealing step starting at 70-68° C. for 30 seconds and decreasing 1° C. per cycle, then a temperature ramp of 0.5° C. per second to 72° C. followed by 72° C. for 1 minute); 25-45 cycles of 94° C. for 20 seconds, 63-61° C. for 30 seconds, ramp 0.5° C./sec to 72° C., 72° C. for 1 minute; 72° C. for 8 minutes; 98° C. for 8 minutes; 80° C. for 20 seconds; 60 cycles of 80° C. for 7 seconds-0.3 degrees/cycle.

The PCR primers (MWG Biotech, Inc., High Point, N.C.) were mixed as follows:

2.5 µl 100 µM IRD-700 labeled left primer
7.5 µl 100 µM left primer
9.0 µl 100 µM IRD-800 labeled right primer
1.0 µl 100 µM right primer A label can be attached to each primer as described or to only one of the primers. Alternatively, Cy5.5 modified primers could be used. The label was coupled to the oligonucleotide using conventional phosphoramidite chemistry.

PCR products (15 µl) were digested in 96-well plates. Next, 30 µl of a solution containing 10 mM HEPES [4-(2-hydroxyethyl)-1-piperazineethanesulfonic acid] (pH 7.5), 10 mM $MgSO_4$, 0.002% (w/v) Triton® X-100, 20 ng/ml of bovine serum albumin, and Surveyor® endonuclease (Transgenomic®, Inc.; 1:100,000 dilution) was added with mixing on ice, and the plate was incubated at 45° C. for 15 minutes. The specific activity of the Surveyor enzyme was 800 units/µl, where a unit was defined by the manufacturer as the amount of enzyme required to produce 1 ng of acid-soluble material from sheared, heat denatured calf thymus DNA at pH 8.5 in one minute at 37° C. Reactions were stopped by addition of 10 µl of a 2.5 M NaCl solution with 0.5 mg/ml blue dextran and 75 mM EDTA, followed by the addition of 80 µl isopropanol. The reactions were precipitated at room temperature, spun at 4,000 rpm for 30 minutes in an Eppendorf Centrifuge 5810. Pellets were resuspended in 8 µl of 33% formamide with 0.017% bromophenol blue dye, heated at 80° C. for 7 minutes and then at 95° C. for 2 minutes. Samples were transferred to a membrane comb using a comb-loading robot (MWG Biotech). The comb was inserted into a slab acrylamide gel (6.5%), electrophoresed for 10 min, and removed. Electrophoresis was continued for 4 hours at 1,500-V, 40-W, and 40-mA limits at 50° C.

During electrophoresis, the gel was imaged using a LI-COR® (Lincoln, Nebr.) scanner which was set at a channel capable of detecting the IR Dye 700 and 800 labels. The gel image showed sequence-specific pattern of background bands common to all 96 lanes. Rare events, such as mutations, create new bands that stand out above the background pattern. Plants with bands indicative of mutations of interest were evaluated by TILLING individual members of a pool mixed with wild type DNA and then sequencing individual PCR products. Plants carrying mutations confirmed by sequencing were grown up as described above (e.g., the M2 plant could be backcrossed or outcrossed twice in order to eliminate background mutations and self-pollinated in order to create a plant that was homozygous for the mutation) or crossed to another plant containing SBEII mutations in a different homoeolog.

Plants that were identified with severe mutations in SBEIIa of the A, B, or D genome were crossed with other plants that contained severe mutations in SBEIIa in other genomes. Severe mutations included those mutations that were predicted to have a deleterious effect on protein function by their SIFT and PSSM, as well as those mutations that resulted in the introduction of a stop codon (truncation mutation) or a mutation at a splice junction. Table 8 shows examples of crosses that were made.

With regard to Tables 8-12, nucleic acid designations of the mutations in SBEIIa of the A genome correspond to the position in the reference sequence SEQ ID NO: 1. Amino acid designations of the SBEIIa polypeptide of the A genome correspond to the amino acid position of reference sequence SEQ ID NO: 2. Nucleic acid designations of the mutations in SBEIIa of the B genome correspond to the position in the reference sequence SEQ ID NO: 3. Amino acid designations of the SBEIIa polypeptide of the B genome correspond to the amino acid position of reference sequence SEQ ID NO: 4. Nucleic acid designations of the mutations in SBEIIa of the D genome correspond to the position in the reference sequence SEQ ID NO: 5. Amino acid designations of the SBEIIa polypeptide of the A genome correspond to the amino acid position of reference sequence SEQ ID NO: 6. Nucleic acid designations of the mutations in SBEIIb of the A genome correspond to the position in the reference sequence SEQ ID NO: 7. Amino acid designations of the SBEIIb polypeptide of the A genome correspond to the amino acid position of reference sequence SEQ ID NO: 8. Nucleic acid designations of the mutations in SBEIIb of the B genome correspond to the position in the reference sequence SEQ ID NO: 9. Amino acid designations of the SBEIIb polypeptide of the B genome correspond to the amino acid position of reference sequence SEQ ID NO: 10. Nucleic acid designations of the mutations in SBEIIb of the D genome correspond to the position in the reference sequence SEQ ID NO: 11. Amino acid designations of the SBEIIb polypeptide of the A genome correspond to the amino acid position of reference sequence SEQ ID NO: 12.

TABLE 8

Examples of wheat plants identified which had a mutation in SBEIIa that was predicted to be severe and the crosses that were made to plants with severe SBEIIa mutations in a different genome.

| Cross | Variety | Gene | Nucleotide Mutation | A.A. Mutation |
|---|---|---|---|---|
| 1 | Express | SBEIIaA | G5267A | W436* |
|   | Express | SBEIIaB | G5038A | W436* |
|   | Express | SBEIIaD | G6305A | W432* |
| 2 | Express | SBEIIaA | G5267A | W436* |
|   | Express | SBEIIaB | G5069A | W446* |
|   | Express | SBEIIaD | G6335A | W442* |
| 3 | Express | SBEIIaA | G5267A | W436* |
|   | Express | SBEIIaB | G5193A | W458* |
|   | Express | SBEIIaD | G6305A | W432* |
| 4 | Kronos | SBEIIaA | G5267A | W436* |
|   | Kronos | SBEIIaB | G5073A | Splice Junction |
| 5 | Kronos | SBEIIaA | G5267A | W436* |
|   | Kronos | SBEIIaB | G5219A | G467E |
| 6 | Kronos | SBEIIaA | G5267A | W436* |
|   | Kronos | SBEIIaB | G5033A | W434* |

Additionally, Express wheat plants identified as containing mutations in SBEIIa were rescreened for mutations in SBEIIb of the same genome using homoeologue specific primers. Plants with mutations in both SBEIIa and SBEIIb of each genome were sequenced and the plants containing severe mutations in both linked genes of the same genome were grown up and self-pollinated to obtain homozygous lines and confirm linkage of the mutations in SBEIIa and SBEIIb. Plants with mutations in both SBEIIa and SBEIIb in the same genome were crossed to plants with linked SBEII mutations in other genomes to obtain wheat lines with linked mutations in all three genomes.

TABLE 9: Examples of twelve Express wheat plants identified which had severe mutations in both SBEIIa and SBEIIb of the same genome (i.e., linked mutations) are shown in Table 9. The SBEIIa and SBEIIb genes are located close together on the chromosome and mutation segregation studies showed that these mutations were linked and were not inherited independently. It would be obvious to one skilled in the art that an alternative approach to identify linked mutations in both genes would be to first identify plants with mutations in their SBEIIb genomes and then rescreen these individuals for mutations in their SBEIIa genomes. It would also be obvious to one skilled in the art that an alternative approach to obtain linked mutations in both genes would be to identify plants in which recombination has occurred between mutations in SBEIIa and SBEIIb.

TABLE 9

Wheat plants with mutations in both SBEIIa and SBEIIb of the same genome

| Plant | Gene | Nucleotide Mutation | A.A. Mutation | Gene | Nucleotide Mutation | A.A. Mutation |
|---|---|---|---|---|---|---|
| 1 | SBEIIaA | C5804T | P519S | SBEIIbA | C2617T | P336L |
| 2 | SBEIIaA | G5463A | G472E | SBEIIbA | G2282A | W285* |
| 3 | SBEIIaA | G5463A | G472E | SBEIIbA | G2282A | W285* |

TABLE 9-continued

Wheat plants with mutations in both SBEIIa and SBEIIb of the same genome

| Plant | Gene | Nucleotide Mutation | A.A. Mutation | Gene | Nucleotide Mutation | A.A. Mutation |
|---|---|---|---|---|---|---|
| 4 | SBEIIaA | G5463A | G472E | SBEIIbA | G2282A | W285* |
| 5 | SBEIIaA | G2605A | G264D | SBEIIbA | G1356A | E216K |
| 6 | SBEIIaA | C5757T | A503V | SBEIIbA | G278A | W59* |
| 7 | SBEIIaD | G6306A | D433N | SBEIIbD | C4573T | R325W |
| 8 | SBEIIaD | G5156A | G374E | SBEIIbD | C4246T | P275L |
| 9 | SBEIIaD | G5156A | G374E | SBEIIbD | C4246T | P275L |
| 10 | SBEIIaD | C3743T | S266F | SBEIIbD | G4290A | V290M |
| 11 | SBEIIaB | G5219A | G467E | SBEIIbB | C3232T | R325W |
| 12 | SBEIIaB | G2386A | G233D | SBEIIbB | C2786T | P263L |

Plants that were homozygous for severe linked mutations (SBEIIa and SBEIIb) in each genome were crossed with plants containing severe linked mutations in other genomes to create plants that had linked SBEIIa and SBEIIb mutations in all three genomes. Multiple combinations of mutations within genomes were produced during the crossing.

TABLE 10

Examples of wheat plants identified that had a severe mutation in SBEIIa and SBEIIb of each genome and crosses to achieve plants with mutations in both SBEIIa and SBEIIb of all three genomes.

| Cross | Gene | Nucleotide Mutation | A.A. Mutation | Gene | Nucleotide Mutation | A.A. Mutation |
|---|---|---|---|---|---|---|
| 1 | SBEIIaA | G2605A | G264D | SBEIIbA | G1356A | E216K |
|   | SBEIIaB | G2386A | G233D | SBEIIbB | C2786T | P263L |
|   | SBEIIaD | G6306A | D433N | SBEIIbD | C4573T | R325W |
| 2 | SBEIIaA | G2605A | G264D | SBEIIbA | G1356A | E216K |
|   | SBEIIaB | G2386A | G233D | SBEIIbB | C2786T | P263L |
|   | SBEIIaD | G5156A | G374E | SBEIIbD | C4246T | P275L |
| 3 | SBEIIaA | G2605A | G264D | SBEIIbA | G1356A | E216K |
|   | SBEIIaB | G2386A | G233D | SBEIIbB | C2786T | P263L |
|   | SBEIIaD | C3743T | S266F | SBEIIbD | G4290A | V290M |
| 4 | SBEIIaA | C5804T | P519S | SBEIIbA | C2617T | P336L |
|   | SBEIIaB | G2386A | G233D | SBEIIbB | C2786T | P263L |
|   | SBEIIaD | G6306A | D433N | SBEIIbD | C4573T | R325W |
| 5 | SBEIIaA | C5804T | P519S | SBEIIbA | C2617T | P336L |
|   | SBEIIaB | G2386A | G233D | SBEIIbB | C2786T | P263L |
|   | SBEIIaD | G5156A | G374E | SBEIIbD | C4246T | P275L |
| 6 | SBEIIaA | C5804T | P519S | SBEIIbA | C2617T | P336L |
|   | SBEIIaB | G2386A | G233D | SBEIIbB | C2786T | P263L |
|   | SBEIIaD | C3743T | S266F | SBEIIbD | G4290A | V290M |
| 7 | SBEIIaA | G5463A | G472E | SBEIIbA | G2282A | W285* |
|   | SBEIIaB | G2386A | G233D | SBEIIbB | C2786T | P263L |
|   | SBEIIaD | G6306A | D433N | SBEIIbD | C4573T | R325W |
| 8 | SBEIIaA | G5463A | G472E | SBEIIbA | G2282A | W285* |
|   | SBEIIaB | G2386A | G233D | SBEIIbB | C2786T | P263L |
|   | SBEIIaD | G5156A | G374E | SBEIIbD | C4246T | P275L |
| 9 | SBEIIaA | G5463A | G472E | SBEIIbA | G2282A | W285* |
|   | SBEIIaB | G2386A | G233D | SBEIIbB | C2786T | P263L |
|   | SBEIIaD | C3743T | S266F | SBEIIbD | G4290A | V290M |
| 10 | SBEIIaA | C5757T | A503V | SBEIIbA | G278A | W59* |
|    | SBEIIaB | G2386A | G233D | SBEIIbB | C2786T | P263L |
|    | SBEIIaD | G6306A | D433N | SBEIIbD | C4573T | R325W |
| 11 | SBEIIaA | C5757T | A503V | SBEIIbA | G278A | W59* |
|    | SBEIIaB | G2386A | G233D | SBEIIbB | C2786T | P263L |
|    | SBEIIaD | G5156A | G374E | SBEIIbD | C4246T | P275L |
| 12 | SBEIIaA | C5757T | A503V | SBEIIbA | G278A | W59* |
|    | SBEIIaB | G2386A | G233D | SBEIIbB | C2786T | P263L |
|    | SBEIIaD | C3743T | S266F | SBEIIbD | G4290A | V290M |
| 13 | SBEIIaA | G2605A | G264D | SBEIIbA | G1356A | E216K |
|    | SBEIIaB | G5219A | G467E | SBEIIbB | C3232T | R325W |
|    | SBEIIaD | G6306A | D433N | SBEIIbD | C4573T | R325W |
| 14 | SBEIIaA | G2605A | G264D | SBEIIbA | G1356A | E216K |
|    | SBEIIaB | G5219A | G467E | SBEIIbB | C3232T | R325W |
|    | SBEIIaD | G5156A | G374E | SBEIIbD | C4246T | P275L |
| 15 | SBEIIaA | G2605A | G264D | SBEIIbA | G1356A | E216K |
|    | SBEIIaB | G5219A | G467E | SBEIIbB | C3232T | R325W |
|    | SBEIIaD | C3743T | S266F | SBEIIbD | G4290A | V290M |
| 16 | SBEIIaA | C5804T | P519S | SBEIIbA | C2617T | P336L |
|    | SBEIIaB | G5219A | G467E | SBEIIbB | C3232T | R325W |
|    | SBEIIaD | G6306A | D433N | SBEIIbD | C4573T | R325W |
| 17 | SBEIIaA | C5804T | P519S | SBEIIbA | C2617T | P336L |
|    | SBEIIaB | G5219A | G467E | SBEIIbB | C3232T | R325W |
|    | SBEIIaD | G5156A | G374E | SBEIIbD | C4246T | P275L |
| 18 | SBEIIaA | C5804T | P519S | SBEIIbA | C2617T | P336L |
|    | SBEIIaB | G5219A | G467E | SBEIIbB | C3232T | R325W |
|    | SBEIIaD | C3743T | S266F | SBEIIbD | G4290A | V290M |
| 19 | SBEIIaA | G5463A | G472E | SBEIIbA | G2282A | W285* |
|    | SBEIIaB | G5219A | G467E | SBEIIbB | C3232T | R325W |
|    | SBEIIaD | G6306A | D433N | SBEIIbD | C4573T | R325W |
| 20 | SBEIIaA | G5463A | G472E | SBEIIbA | G2282A | W285* |
|    | SBEIIaB | G5219A | G467E | SBEIIbB | C3232T | R325W |
|    | SBEIIaD | G5156A | G374E | SBEIIbD | C4246T | P275L |
| 21 | SBEIIaA | G5463A | G472E | SBEIIbA | G2282A | W285* |
|    | SBEIIaB | G5219A | G467E | SBEIIbB | C3232T | R325W |
|    | SBEIIaD | C3743T | S266F | SBEIIbD | G4290A | V290M |
| 22 | SBEIIaA | C5757T | A503V | SBEIIbA | G278A | W59* |
|    | SBEIIaB | G5219A | G467E | SBEIIbB | C3232T | R325W |
|    | SBEIIaD | G6306A | D433N | SBEIIbD | C4573T | R325W |
| 23 | SBEIIaA | C5757T | A503V | SBEIIbA | G278A | W59* |
|    | SBEIIaB | G5219A | G467E | SBEIIbB | C3232T | R325W |
|    | SBEIIaD | G5156A | G374E | SBEIIbD | C4246T | P275L |
| 24 | SBEIIaA | C5757T | A503V | SBEIIbA | G278A | W59* |
|    | SBEIIaB | G5219A | G467E | SBEIIbB | C3232T | R325W |
|    | SBEIIaD | C3743T | S266F | SBEIIbD | G4290A | V290M |

TABLE 11

Three examples of wheat plants with other combinations of mutations of SBEIIa and SBEIIb of multiple genomes.

| Type | Gene | Nucleotide Mutation | A.A. Mutation | Gene | Nucleotide Mutation | A.A. Mutation |
|---|---|---|---|---|---|---|
| SBEIIa Only | SBEIIaA | G5267A | W436* | | | |
| LinkedSBEIIa & IIb | SBEIIaB | G2386A | G233D | SBEIIbB | C2786T | P263L |
| LinkedSBEIIa & IIb | SBEIIaD | G6306A | D433N | SBEIIbD | C4573T | R325W |
| LinkedSBEIIa & IIb | SBEIIaA | G2605A | G264D | SBEIIbA | G1668A | E216K |
| SBEIIa Only | SBEIIaA | G5038A | W436* | | | |
| LinkedSBEIIa & IIb | SBEIIaD | G6306A | D433N | SBEIIbD | C4573T | R325W |
| LinkedSBEIIa & IIb | SBEIIaA | G2605A | G264D | SBEIIbA | G1668A | E216K |
| LinkedSBEIIa & IIb | SBEIIaB | G2386A | G233D | SBEIIbB | C2786T | P263L |
| SBEIIa Only | SBEIIaD | G6305A | W432* | | | |

TABLE 12

Additional examples of wheat plants with other combinations of mutations of SBEIIa and SBEIIb of multiple genomes.

| Combo | Type | Gene | Nucleotide Mutation | A.A. Mutation | Gene | Nucleotide Mutation | A.A. Mutation |
|---|---|---|---|---|---|---|---|
| 1 | LinkedSBEIIa & IIb | SBEIIaA | G5267A | W436* | SBEIIbA | G2282A | W285* |
|  | LinkedSBEIIa & IIb | SBEIIaB | G5038A | W436* | SBEIIbB | G1916A | S208N |
|  | LinkedSBEIIa & IIb | SBEIIaD | G6305A | W432* | SBEIIbD | G3599A | W233* |
| 2 | SBEIIa Only | SBEIIaA | G5267A | W436* | SBEIIbA |  |  |
|  | LinkedSBEIIa & IIb | SBEIIaB | G5038A | W436* | SBEIIbB | G1916A | S208N |
|  | LinkedSBEIIa & IIb | SBEIIaD | G6305A | W432* | SBEIIbD | G3599A | W233* |
| 3 | LinkedSBEIIa & IIb | SBEIIaA | G5267A | W436* | SBEIIbA | G2282A | W285* |
|  | SBEIIa Only | SBEIIaB | G5038A | W436* | SBEIIbB |  |  |
|  | LinkedSBEIIa & IIb | SBEIIaD | G6305A | W432* | SBEIIbD | G3599A | W233* |
| 4 | LinkedSBEIIa & IIb | SBEIIaA | G5267A | W436* | SBEIIbA | G2282A | W285* |
|  | LinkedSBEIIa & IIb | SBEIIaB | G5038A | W436* | SBEIIbB | G1916A | S208N |
|  | SBEIIa Only | SBEIIaD | G6305A | W432* | SBEIIbD |  |  |
| 5 | SBEIIa Only | SBEIIaA | G5267A | W436* | SBEIIbA |  |  |
|  | SBEIIa Only | SBEIIaB | G5038A | W436* | SBEIIbB |  |  |
|  | LinkedSBEIIa & IIb | SBEIIaD | G6305A | W432* | SBEIIbD | G3599A | W233* |
| 6 | LinkedSBEIIa & IIb | SBEIIaA | G5267A | W436* | SBEIIbA | G2282A | W285* |
|  | SBEIIa Only | SBEIIaB | G5038A | W436* | SBEIIbB |  |  |
|  | SBEIIa Only | SBEIIaD | G6305A | W432* | SBEIIbD |  |  |
| 7 | SBEIIa Only | SBEIIaA | G5267A | W436* | SBEIIbA |  |  |
|  | LinkedSBEIIa & IIb | SBEIIaB | G5038A | W436* | SBEIIbB | G1916A | S208N |
|  | SBEIIa Only | SBEIIaD | G6305A | W432* | SBEIIbD |  |  |
| 8 | LinkedSBEIIa & IIb | SBEIIaA | G5267A | W436* | SBEIIbA | G2156A | Splice Junction |
|  | LinkedSBEIIa & IIb | SBEIIaB | G5038A | W436* | SBEIIbB | C3232T | R325W |
|  | LinkedSBEIIa & IIb | SBEIIaD | G6305A | W432* | SBEIIbD | C4573T | R325W |
| 9 | SBEIIa Only | SBEIIaA | G5267A | W436* | SBEIIbA |  |  |
|  | LinkedSBEIIa & IIb | SBEIIaB | G5038A | W436* | SBEIIbB | C3232T | R325W |
|  | LinkedSBEIIa & IIb | SBEIIaD | G6305A | W432* | SBEIIbD | C4573T | R325W |
| 10 | LinkedSBEIIa & IIb | SBEIIaA | G5267A | W436* | SBEIIbA | G2156A | Splice Junction |
|  | SBEIIa Only | SBEIIaB | G5038A | W436* | SBEIIbB |  |  |
|  | LinkedSBEIIa & IIb | SBEIIaD | G6305A | W432* | SBEIIbD | C4573T | R325W |
| 11 | LinkedSBEIIa & IIb | SBEIIaA | G5267A | W436* | SBEIIbA | G2156A | Splice Junction |
|  | LinkedSBEIIa & IIb | SBEIIaB | G5038A | W436* | SBEIIbB | C3232T | R325W |
|  | SBEIIa Only | SBEIIaD | G6305A | W432* | SBEIIbD |  |  |
| 12 | SBEIIa Only | SBEIIaA | G5267A | W436* | SBEIIbA |  |  |
|  | SBEIIa Only | SBEIIaB | G5038A | W436* | SBEIIbB |  |  |
|  | LinkedSBEIIa & IIb | SBEIIaD | G6305A | W432* | SBEIIbD | C4573T | R325W |
| 13 | LinkedSBEIIa & IIb | SBEIIaA | G5267A | W436* | SBEIIbA | G2156A | Splice Junction |
|  | SBEIIa Only | SBEIIaB | G5038A | W436* | SBEIIbB |  |  |
|  | SBEIIa Only | SBEIIaD | G6305A | W432* | SBEIIbD |  |  |
| 14 | SBEIIa Only | SBEIIaA | G5267A | W436* | SBEIIbA |  |  |
|  | LinkedSBEIIa & IIb | SBEIIaB | G5038A | W436* | SBEIIbB | C3232T | R325W |
|  | SBEIIa Only | SBEIIaD | G6305A | W432* | SBEIIbD |  |  |
| 15 | LinkedSBEIIa & IIb | SBEIIaA | G5267A | W436* | SBEIIbA | G2282A | W285* |
|  | LinkedSBEIIa & IIb | SBEIIaB | G5038A | W436* | SBEIIbB | C3232T | R325W |
|  | LinkedSBEIIa & IIb | SBEIIaD | G6305A | W432* | SBEIIbD | C4573T | R325W |
| 16 | LinkedSBEIIa & IIb | SBEIIaA | G5267A | W436* | SBEIIbA | G2282A | W285* |
|  | LinkedSBEIIa & IIb | SBEIIaB | G5038A | W436* | SBEIIbB | C3232T | R325W |
|  | LinkedSBEIIa & IIb | SBEIIaD | G6305A | W432* | SBEIIbD | G3599A | W233* |
| 17 | LinkedSBEIIa & IIb | SBEIIaA | G5267A | W436* | SBEIIbA | G2282A | W285* |
|  | LinkedSBEIIa & IIb | SBEIIaB | G5038A | W436* | SBEIIbB | G1916A | S208N |
|  | LinkedSBEIIa & IIb | SBEIIaD | G6305A | W432* | SBEIIbD | C4573T | R325W |
| 18 | SBEIIa Only | SBEIIaA | G5267A | W436* | SBEIIbA |  |  |
|  | LinkedSBEIIa & IIb | SBEIIaB | G5038A | W436* | SBEIIbB | C3232T | R325W |
|  | LinkedSBEIIa & IIb | SBEIIaD | G6305A | W432* | SBEIIbD | G3599A | W233* |
| 19 | SBEIIa Only | SBEIIaA | G5267A | W436* | SBEIIbA |  |  |
|  | LinkedSBEIIa & IIb | SBEIIaB | G5038A | W436* | SBEIIbB | G1916A | S208N |
|  | LinkedSBEIIa & IIb | SBEIIaD | G6305A | W432* | SBEIIbD | G3599A | W233* |
| 20 | SBEIIa Only | SBEIIaA | G5267A | W436* | SBEIIbA |  |  |
|  | LinkedSBEIIa & IIb | SBEIIaB | G5038A | W436* | SBEIIbB | G1916A | S208N |
|  | LinkedSBEIIa & IIb | SBEIIaD | G6305A | W432* | SBEIIbD | C4573T | R325W |
| 21 | LinkedSBEIIa & IIb | SBEIIaA | G5267A | W436* | SBEIIbA | G2282A | W285* |
|  | SBEIIa Only | SBEIIaB | G5038A | W436* | SBEIIbB |  |  |
|  | LinkedSBEIIa & IIb | SBEIIaD | G6305A | W432* | SBEIIbD | C4573T | R325W |
| 22 | LinkedSBEIIa & IIb | SBEIIaA | G5267A | W436* | SBEIIbA | G2156A | Splice Junction |
|  | SBEIIa Only | SBEIIaB | G5038A | W436* | SBEIIbB |  |  |
|  | LinkedSBEIIa & IIb | SBEIIaD | G6305A | W432* | SBEIIbD | G3599A | W233* |
| 23 | LinkedSBEIIa & IIb | SBEIIaA | G5267A | W436* | SBEIIbA | G2282A | W285* |
|  | LinkedSBEIIa & IIb | SBEIIaB | G5038A | W436* | SBEIIbB | C3232T | R325W |
|  | SBEIIa Only | SBEIIaD | G6305A | W432* | SBEIIbD |  |  |
| 24 | LinkedSBEIIa & IIb | SBEIIaA | G5267A | W436* | SBEIIbA | G2156A | Splice Junction |
|  | LinkedSBEIIa & IIb | SBEIIaB | G5038A | W436* | SBEIIbB | G1916A | S208N |
|  | SBEIIa Only | SBEIIaD | G6305A | W432* | SBEIIbD |  |  |

Mutations in SBEIIa increase amylose content and resistant starch levels in wheat seeds from (1) double homozygous Kronos wheat plants with a stop mutation in SBEIIaA (G5267A/W436*) and a splice junction mutation in SBEIIaB (G5073A/splice junction), and (2) double homozygous Kronos wheat plants with a stop mutation in SBEIIaA (G5267A/W436*) and a missense mutation in SBEIIaB (G5219A/G467E) were evaluated for amylose content using the K-AMYL kit from Megazyme (Ireland) and controls of known amylose amounts. The amylose content of whole seed milled starch was an average of 40-49% for the double homozygous mutant seeds compared to seeds from their wild type sibling controls whose amylose content was 20-25%.

Seeds from (1) triple homozygous Express wheat plants with a stop mutation in SBEIIaA (G5267A/W436*), SBEIIaB (G5038A/W436*), and SBEIIaD (G6305A/W432*), and (2) triple homozygous Express wheat plants with a stop mutation in SBEIIaA (G5267A/W436*), SBEIIaB (G5069A/W446*), and SBEIIaD (G6335A/W442*) were evaluated for amylose content using the K-AMYL kit from Megazyme (Ireland) and a controls of known amylose amounts. The amylose content of whole seed milled starch was 50-60% for the triple homozygous mutant seeds compared to seeds from their wild type sibling controls whose amylose content was 20-25%.

Flour milled from the triple homozygous mutant seed had 12-15% resistant starch content compared to flour from the wild type sibling controls, which had approximately 1% resistant starch. Bread made from the triple homozygous mutant flour had increased resistant starch levels of 6% compared to bread made from flour of wild type sibling and parental controls, which had less than 1% resistant starch. Bread made from a 50:50 blend with standard wheat flour had increased resistant starch levels of 4% compared to bread made from a 50:50 blend with sibling control flour that had resistant starch levels less than 1%.

Seeds from (1) quadruple homozygous Express wheat plants with a linked mutation in SBEIIaA (G5463A/G472E)- and SBEIIbA (G2282A/W285*), combined with a stop mutation in SBEIIaB (G5038A/W436*), and SBEIIaD (G6305A/W432) was evaluated for amylose content using the K-AMYL kit from Megazyme (Ireland) and controls of known amylose amounts. The amylose content of whole seed milled starch was 58% for the quadruple homozygous mutant seeds compared to seeds from their wild type sibling controls whose amylose content was 20-25%.

Seeds from (2) quadruple homozygous Express wheat plants with a stop mutation in SBEIIaA (G5267A/W436*), combined with a stop mutation in SBEIIaB (G5038A/W436*), and a linked mutation in SBEIIaD (G6306A/D433N)- and SBEIIbD (C4573T/R325W) was evaluated for amylose content using the K-AMYL kit from Megazyme (Ireland) and controls of known amylose amounts. The amylose content of whole seed milled starch was 38% for the quadruple homozygous mutant seeds compared to seeds from their wild type sibling controls whose amylose content was 23%.

Seeds from (3) quadruple homozygous Express wheat plants with a stop mutation in SBEIIaA (G5267A/W436*), combined with a linked mutation in SBEIIaB (G5219A/G467E)- and SBEIIbB (C3232T/R325W), and a stop mutation in SBEIIaD (G6305A/W432*) were evaluated for amylose content using the K-AMYL kit from Megazyme (Ireland) and controls of known amylose amounts. The amylose content of whole seed milled starch was 38% for the quadruple homozygous mutant seeds compared to seeds from their wild type sibling controls whose amylose content was 24%.

Seeds from a sextuple homozygous Express wheat plants with linked mutations in SBEIIaA (G5463A/G472E) and SBEIIbA (G2282A/W285*), combined with linked mutations in SBEIIaB (G5219A/G467E) and SBEIIbB (C3232T/R325W), and linked mutations in SBEIIaD (G6306A/D433N) and SBEIIbD (C4573T/R325W) were evaluated for amylose content using the K-AMYL kit from Megazyme (Ireland) and controls of known amylose amounts. The amylose content of whole seed milled starch was 25-30% for the sextuple homozygous mutant seeds compared to seeds from their wild type sibling controls whose amylose content was 16%.

The above examples are provided to illustrate the invention but not limit its scope. Other variants of the invention will be readily apparent to one of ordinary skill in the art and are encompassed by the appended claims and all their equivalents. The examples above used TILLING technology to create and identify mutations in one or more SBEII genes of wheat that increase amylose levels in wheat seeds, but one of ordinary skill in the art would understand that other methods such as targeted mutagenesis (also known as site-directed mutagenesis, site-specific mutagenesis or oligonucleotide-directed mutagenesis) could be used to create the useful mutations of the present invention in one or more SBEII loci of wheat (see for example Zhang et al., *PNAS* 107(26):12028-12033, 2010; Saika et al., *Plant Physiology* 156:1269-1277, 2011). All publications, patents, and patent applications cited herein are hereby incorporated by reference.

What is claimed is:

1. A process for producing a milled product, comprising:
   (i) providing wheat grain (*Triticum aestivum*) comprising an embryo and starch, wherein the embryo comprises three starch branching enzyme IIa (SBEIIa) genes, wherein both alleles of the SBEIIa-A gene are identical, both alleles of the SBEIIa-B gene are identical, and both alleles of the SBEIIa-D gene are identical, and wherein
      (a) the SBEIIa-A gene has a severe mutation that is a short deletion, the SBEIIa-B gene has a severe mutation that is a short deletion, and the SBEIIa-D gene has a severe mutation that is a short deletion;
      (b) SBEIIa enzyme activity is reduced or eliminated in the wheat grain;
      (c) the wheat grain has an increased amylose content compared to the amylose content of wild type wheat grain; and
      (d) the wheat grain is capable of germinating, and
   (ii) milling the grain to produce a milled grain product.

2. The process of claim 1, wherein the wheat grain is non-transgenic.

3. The process of claim 1, wherein the severe mutation that is a short deletion of the SBEIIa-A gene, the severe mutation that is a short deletion of the SBEIIa-B gene, and the severe mutation that is a short deletion of the SBEIIa-D gene prematurely truncate translation of the SBEIIa enzyme from messenger RNA.

4. The process of claim 1, wherein the starch of the grain comprises at least 12-15% (w/w) resistant starch.

5. The process of claim 1, in which the milled product is wheat flour or wholemeal.

6. The process of claim 1, wherein SBEIIa protein is undetectable in the wheat grain.

7. The process of claim 1, wherein the severe mutation that is a short deletion of the SBEIIa-A gene is 1 to 30 nucleotides.

8. The process of claim 1, wherein the severe mutation that is a short deletion of the SBEIIa-B gene is 1 to 30 nucleotides.

9. The process of claim 1, wherein the severe mutation that is a short deletion of the SBEIIa-D gene is 1 to 30 nucleotides.

10. The process of claim 1, wherein the severe mutation that is a short deletion of the SBEIIa-A gene is 1 to 30 nucleotides, the severe mutation that is a short deletion of the SBEIIa-B gene is 1 to 30 nucleotides, and the severe mutation that is a short deletion of the SBEIIa-D gene is 1 to 30 nucleotides.

* * * * *